US008367070B2

(12) United States Patent
Peak et al.

(10) Patent No.: US 8,367,070 B2
(45) Date of Patent: Feb. 5, 2013

(54) MODIFIED SURFACE ANTIGEN

(75) Inventors: Ian Richard Anselm Peak, Upper Coomera (AU); Michael Paul Jennings, St. Lucia (AU)

(73) Assignee: The University of Queensland, St. Lucia, Queensland (AU)

( * ) Notice: Subject to any disclaimer, the term of this patent is extended or adjusted under 35 U.S.C. 154(b) by 572 days.

(21) Appl. No.: 11/933,245

(22) Filed: Oct. 31, 2007

(65) Prior Publication Data

US 2009/0068216 A1    Mar. 12, 2009

Related U.S. Application Data

(63) Continuation of application No. 09/771,382, filed on Jan. 25, 2001, now Pat. No. 7,947,291.

(60) Provisional application No. 60/177,917, filed on Jan. 25, 2000.

(51) Int. Cl.

| A61K 39/00 | (2006.01) |
|---|---|
| A61K 39/38 | (2006.01) |
| A61K 39/02 | (2006.01) |
| A61K 39/095 | (2006.01) |
| A61K 31/00 | (2006.01) |
| A61K 45/00 | (2006.01) |
| A61K 47/00 | (2006.01) |
| C07K 1/00 | (2006.01) |
| C07K 14/00 | (2006.01) |
| C07K 17/00 | (2006.01) |

(52) U.S. Cl. ............... 424/190.1; 424/184.1; 424/250.1; 424/278.1; 514/1; 530/350

(58) Field of Classification Search ........................ None
See application file for complete search history.

(56) References Cited

U.S. PATENT DOCUMENTS

| 6,197,312 | B1 * | 3/2001 | Peak et al. ................. | 424/250.1 |
|---|---|---|---|---|
| 6,709,660 | B1 | 3/2004 | Scarlato et al. | |
| 8,029,807 | B2 | 10/2011 | Bos et al. .................... | 424/249.1 |
| 8,034,358 | B2 * | 10/2011 | Peak et al. ................. | 424/250.1 |
| 8,067,004 | B2 * | 11/2011 | Peak et al. ................. | 424/150.1 |
| 8,163,295 | B2 * | 4/2012 | Bos et al. .................... | 424/249.1 |
| 2002/0160016 | A1 | 10/2002 | Peak et al. | |
| 2012/0027800 | A1 * | 2/2012 | Berthet et al. .............. | 424/249.1 |
| 2012/0039942 | A1 * | 2/2012 | Bos et al. .................... | 424/249.1 |
| 2012/0064119 | A1 * | 3/2012 | Berthet et al. .............. | 424/250.1 |
| 2012/0064120 | A1 * | 3/2012 | Berthet et al. .............. | 424/250.1 |
| 2012/0123093 | A1 * | 5/2012 | Peak et al. ................... | 530/350 |

FOREIGN PATENT DOCUMENTS

| EP | 0 273 116 A2 | 7/1988 |
|---|---|---|
| WO | 90/06696 A2 | 6/1990 |
| WO | 97/46582 A1 | 12/1997 |
| WO | 99/31132 | 6/1999 |
| WO | 99/31132 A1 | 6/1999 |
| WO | WO 99/31132 * | 6/1999 |
| WO | 99/36544 | 7/1999 |
| WO | 99/36544 A2 | 7/1999 |
| WO | 99/58683 A2 | 11/1999 |
| WO | 00/61165 A1 | 10/2000 |
| WO | 00/66741 A2 | 11/2000 |
| WO | 00/66791 A1 | 11/2000 |
| WO | 01/04316 A2 | 1/2001 |

OTHER PUBLICATIONS

Ellis (Vaccines, W.B. Saunders Company, 1988, Chapter 29).*
Boslego et al (Vaccines and Immunotherapy, Pergaman Press, 1991, Chapter 17).*
Greenspan et al. (Nature Biotechnology 7: 936-937, 1999).*
Bowie et al (Science, 1990, 257:1306-1310).*
Greenspan et al., "Defining Epitopes: It's not as Easy as it Seems", Nature Biotechnology, 1999, 936-937, vol. 17.
Bowie et al., "Deciphering the Message in Protein Sequences: Tolerance to Amino Acid Substitutions", Science, 1990, 1306-1310, vol. 257.
Thomas E. Creighton, in his book, "Proteins: Structures and Molecular Properties", 1984, 314-315, W.H. Freeman Company.
Thomas E. Creighton, in his book, "Protein Structure: A Practical Approach", May 1989, 184-186, Oxford University Press.
Nosoh, Y. et al. in "Protein Stability and Stabilization through Protein Engineering", 1991, 197, NY: Ellis Horwood.
Annika A. Pettersson et al., "Sequence variability of the meningococcal lactoferrin-binding protein LbpB", Gene, Feb. 24, 1999, 105-110, vol. 231.
John E. Heckels et al., "Vaccination against gonorrhoea: the potential protective effect of immunization with a synthetic peptide containing a conserved epitope of gonococcal outer membrane protein IB", Vaccine, Jun. 1990, 225-230, vol. 8, Butterworth-Heinemann, London G.B.
Mariagrazia Pizza et al., (XP-000914964) "Identification of Vaccine Candidates Against Serogroup B *Meningococcus* by Whole-Genome Sequencing", Science, Mar. 10, 2000, 1816-1820, vol. 287, with XP002312283—EBI accession No. UNIPROT:Q9JR18—Database accession No. Q9JR18.
Ian R. A. Peak et al., "Identification and characterisation of a novel conserved outer membrane protein from *Neisseria meningitidis*", FEMS Immunology and Medical Microbiology, May 9, 2000, 329-334, vol. 28.
J. Parkhill et al., (XP-000918875) "Complete DNA sequence of a serogroup A strain of *Neisseria meningitidis* Z2491", Nature, Mar. 30, 2000, 502-505, vol. 404.

(Continued)

*Primary Examiner* — Nita M Minnifield
(74) *Attorney, Agent, or Firm* — Panitch Schwarze Belisario & Nadel LLP

(57) ABSTRACT

Novel proteins that constitute modified forms of a *Neisseria meningitidis* surface antigen and encoding nucleic acids are provided. The modified surface proteins are characterized by having deletions of non-conserved amino acids, and thereby being capable of eliciting cross-protective immune responses against *Neisseria meningitidis*. The invention extends to the use of the modified surface antigens in diagnostics, in therapeutic and prophylactic vaccines and in the design and/or screening of medicaments. The modified surface antigens are particularly useful in vaccines which effectively immunize against a broader spectrum of *N. meningitidis* strains than would be expected from a corresponding wild-type surface antigen.

16 Claims, 31 Drawing Sheets

OTHER PUBLICATIONS

Figure 3A:
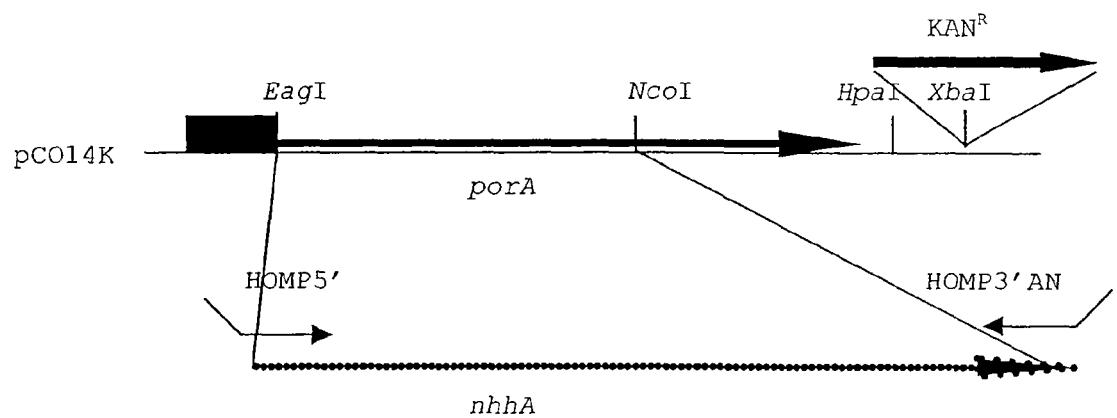

Herve Tettelin et al., (XP-000914963) "Complete Genome Sequence of *Neisseria meningitidis* Serogroup B Strain MC58", Science, Mar. 10, 2000, 1809-1815, vol. 287.
Thomas P. Hopp, et al. "A Computer Program for Predicting Protein Antigenic Determinants", Molecular Immunology, 1983, 483-489, vol. 20, No. 4.
A.S. Kolaskar et al. "A semi-empirical method for prediction of antigenic determinants on protein antigens", FEBS, Dec. 1990, 172-174, vol. 276, No. 1, 2.
Gjalt W. Welling et al., "Prediction of sequential antigenic regions in proteins", FEBS, Sep. 1985, 215-218, vol. 188.
Barenkamp et al., GenPept Database Accession No. AAC43721 (Mar. 21, 1996).
St Geme et al., GenPept Database Accession No. AAC44560 (Oct. 27, 1999).
Fleishmann et al., PIR Database Accession No. I64138 (Oct. 24, 1997).
Gilmore et al., "Mol Microbiology," Nov. 1989, 3(11):1579-1586. Abstract Only.
Zhao et al., "Mol Gen Genet", Aug. 1990, 223(1):163-166. (Abstract Only).
Office Action for U.S. Appl. No. 09/771,382, dated May 6, 2009.
Office Action for U.S. Appl. No. 09/771,382, dated Nov. 26, 2008.
Office Action for U.S. Appl. No. 09/771,382, dated Feb. 8, 2008.
Office Action for U.S. Appl. No. 09/771,382, dated Sep. 21, 2007.
Office Action for U.S. Appl. No. 09/771,382, dated Mar. 8, 2007.
Office Action for U.S. Appl. No. 09/771,382, dated Jan. 10, 2006.
Office Action for U.S. Appl. No. 09/771,382, dated Apr. 4, 2005.
Office Action for U.S. Appl. No. 09/771,382, dated Jul. 21, 2004.
Office Action for U.S. Appl. No. 09/771,382, dated Oct. 30, 2003.
Office Action for U.S. Appl. No. 09/771,382, dated Jan. 17, 2003.
Office Action for U.S. Appl. No. 09/771,382, dated Jul. 12, 2002.
Office Action for U.S. Appl. No. 09/771,382, dated Apr. 1, 2010.
Supplementary Partial Search Report Issued in EP Application No. EP01946868, 2005.
Communication from Australian Patent Office in AU Application No. PCT/AU01/00069, 2001.
Office Action Issued Apr. 16, 2010 in U.S. Appl. No. 11/933,411.
Office Action Issued Feb. 27, 2009 in U.S. Appl. No. 09/771,382.
Office Action Issued Mar. 22, 2002 in U.S. Appl. No. 09/771,382.
Hoppner (Horm Re. 2002, 58 Suppl. 3:7-15 (Abstract Only).
Kleppe et al (Tidsskr Nor Laegeforen, Sep. 30, 2001; 121(23):2717-20 (Abstract Only).
Office Action issued Oct. 12, 2010 in U.S. Appl. No. 11/933,411.
Summons to Oral Proceedings dated Nov. 8, 2010 in EP Application No. 01946868.5.
Reexamination Report dated Sep. 15, 2010 in CN Application No. 01807183.
Office Action issued Sep. 14, 2010 in JP Application No. 2001561034.
Extended EP Search Report issued Feb. 22, 2012 in EP Application No. 10184045.2.

* cited by examiner

```
            1                                                     50
   EG327    MNKIYRIIWN  SALNAWVAVS  ELTRNHTKRA  SATVATAVLA  TLLFATVQAS
   BZ198    MNKIYRIIWN  SALNAWVVVS  ELTRNHTKRA  SATVATAVLA  TLLFATVQAN
    BZ10    MNKISRIIWN  SALNAWVVVS  ELTRNHTKRA  SATVATAVLA  TLLFATVQAN
     H15    MNKIYRIIWN  SALNAWVVVS  ELTRNHTKRA  SATVATAVLA  TLLFATVQAN
   EG329    MNEILRIIWN  SALNAWVVVS  ELTRNHTKRA  SATVKTAVLA  TLLFATVQAS
   PMC21    MNKIYRIIWN  SALNAWVVVS  ELTRNHTKRA  SATVKTAVLA  TLLFATVQAS
     H38    MNKIYRIIWN  SALNAWVAVS  ELTRNHTKRA  SATVKTAVLA  TLLFATVQAN
     P20    MNKIYRIIWN  SALNAWVVVS  ELTRNHTKRA  SATVATAVLA  TLLSATVQAN
   Z2491    MNKIYRIIWN  SALNAWVAVS  ELTRNHTKRA  SATVKTAVLA  TLLFATVQAN
     H41    MNKIYRIIWN  SALNAWVAVS  ELTRNHTKRA  SATVKTAVLA  TLLFATVQAN
Consensus   MN-I-RIIWN  SALNAWV-VS  ELTRNHTKRA  SATV-TAVLA  TLL-ATVQA-
                                        C1

51                                                    100
   EG327    TTDDD...DL  YLEPVQRTAV  VLSFRSDKEG  TGEKE.VTED  SNWGVYFDKK
   BZ198    ATDDD...DL  YLEPVQRTAV  VLSFRSDKEG  TGEKE.GTED  SNWAVYFDEK
    BZ10    ATDDD...DL  YLEPVQRTAV  VLSFRSDKEG  TGEKE.GTED  SNWAVYFDEK
     H15    ATDDD...DL  YLEPVQRTAV  VLSFRSDKEG  TGEKE.GTED  SNWAVYFDEK
   EG329    ANNEEQEEDL  YLDPVLRTVA  VLIVNSDKEG  TGEKEKVEEN  SDWAVYFNEK
   PMC21    ANNEEQEEDL  YLDPVQRTVA  VLIVNSDKEG  TGEKEKVEEN  SDWAVYFNEK
     H38    ATDED..EEE  ELEPVVRSAL  VLQFMIDKEG  NGENE.STGN  IGWSIYYDNH
     P20    ATDTD..EDE  ELESVARSAL  VLQFMIDKEG  NGEIESTGDI  GWSIYYDDHN
   Z2491    ATDED..EEE  ELESVQR.SV  VGSIQASMEG  SGELET...I  SLSMTNDSKE
     H41    ATDED..EEE  ELESVQR.SV  VGSIQASMEG  SVELET...I  SLSMTNDSKE
Consensus   ----------  -L--V-R---  V-------EG  --E-E-----  ----------
                                        V1

101                                                   150
   EG327    GVLTAGTITL  KAGDNLKIKQ  NTNENTNASS  ....FTYSLK  KDLTDLTSVG
   BZ198    RVLKAGAITL  KAGDNLKIKQ  NTNENTNDSS  ...FTYSLK   KDLTDLTSVE
    BZ10    RVLKAGAITL  KAGDNLKIKQ  NTNENTNENT  NDSSFTYSLK  KDLTDLTSVE
     H15    RVLKAGAITL  KAGDNLKIKQ  NTNENTNENT  NDSSFTYSLK  KDLTDLTSVE
   EG329    GVLTAREITL  KAGDNLKIKQ  NG...TN...  ....FTYSLK  KDLTDLTSVG
   PMC21    GVLTAREITL  KAGDNLKIKQ  NG...TN...  ....FTYSLK  KDLTDLTSVG
     H38    NTLHGATVTL  KAGDNLKIKQ  NTNKNTNENT  NDSSFTYSLK  KDLTDLTSVE
     P20    TLHG.ATVTL  KAGDNLKIKQ  SGKD......  ....FTYSLK  KELKDLTSVE
   Z2491    FVDPYIVVTL  KAGDNLKIKQ  NTNENTNASS  ....FTYSLK  KDLTGLINVE
     H41    FVDPYIVVTL  KAGDNLKIKQ  NTNENTNASS  ....FTYSLK  KDLTGLINVE
Consensus   --------TL  KAGDNLKIKQ  ----------  ----FTYSLK  K-L--L--V-
                V1          C2          V2                     C3
```

FIG. 1A

```
              151                                                              200
    EG327     TEKLSFSANS  NKVNITSDTK  GLNFAKKTAE  TNGDTTVHLN  GIGSTLTDTL
    BZ198     TEKLSFGANG  NKVNITSDTK  GLNFAKETAG  TNGDPTVHLN  GIGSTLTDTL
    BZ10      TEKLSFGANG  NKVNITSDTK  GLNFAKETAG  TNGDPTVHLN  GIGSTLTDTL
    H15       TEKLSFGANG  NKVNITSDTK  GLNFAKETAG  TNGDPTVHLN  GIGSTLTDTL
    EG329     TEKLSFSANS  NKVNITSDTK  GLNFAKETAG  TNGDTTVHLN  GIGSTLTDTL
    PMC21     TEKLSFSANS  NKVNITSDTK  GLNFAKETAG  TNGDTTVHLN  GIGSTLTDTL
    H38       TEKLSFGANG  NKVNITSDTK  GLNFAKETAG  TNGDTTVHLN  GIGSTLTDTL
    P20       TEKLSFGANG  NKVNITSDTK  GLNFAKETAG  TNGDPTVHLN  GIGSTLTDTL
    Z2491     TEKLSFGANG  KKVNIISDTK  GLNFAKETAG  TNGDTTVHLN  GIGSTLTDTL
    H41       TEKLSFGANG  KKVNIISDTK  GLNFAKETAG  TNGDTTVHLN  GIGSTLTDML
Consensus     TEKLSF-AN-  -KVNI-SDTK  GLNFAK-TA-  TNGD-TVHLN  GIGSTLTD-L
                                           C3

201                                                              250
    EG327     LNTGATTNVT  NDNVTDDEKK  RAASVKDVLN  AGWNIKGVKP  GTTAS..DNV
    BZ198     LNTGATTNVT  NDNVTDDEKK  RAASVKDVLN  AGWNIKGVKP  GTTAS..DNV
    BZ10      LNTGATTNVT  NDNVTDDEKK  RAASVKDVLN  AGWNIKGVKP  GTTAS..DNV
    H15       LNTGATTNVT  NDNVTDDEKK  RAASVKDVLN  AGWNIKGVKP  GTTAS..DNV
    EG329     LNTGATTNVT  NDNVTDDEKK  RAASVKDVLN  AGWNIKGVKP  GTTAS..DNV
    PMC21     LNTGATTNVT  NDNVTDDEKK  RAASVKDVLN  AGWNIKGVKP  GTTAS..DNV
    H38       LNTGATTNVT  NDNVTDDKKK  RAASVKDVLN  AGWNIKGVKP  GTTAS..DNV
    P20       AGSSASHVDA  GNQST..HYT  RAASIKDVLN  AGWNIKGVKT  GSTTGQSENV
    Z2491     AGSSASHVDA  GNQST..HYT  RAASIKDVLN  AGWNIKGVKT  GSTTGQSENV
    H41       LNTGATTNVT  NDNVTDDEKK  RAASVKDVLN  AGWNIKGVKP  GTTAS..DNV
Consensus     ----A-----  ----T-----  RAAS-KDVLN  AGWNIKGVK-  G-T-----NV
                  V3                         C4                    V4

251                                                              300
    EG327     DFVRTYDTVE  FLSADTKTTT  VNVESKDNGK  RTEVKIGAKT  SVIKEKDGKL
    BZ198     DFVRTYDTVE  FLSADTKTTT  VNVESKDNGK  KTEVKIGAKT  SVIKEKDGKL
    BZ10      DFVRTYDTVE  FLSADTKTTT  VNVESKDNGK  KTEVKIGAKT  SVIKEKDGKL
    H15       DFVRTYDTVE  FLSADTKTTT  VNVESKDNGK  KTEVKIGAKT  SVIKEKDGKL
    EG329     DFVRTYDTVE  FLSADTKTTT  VNVESKDNGK  KTEVKIGAKT  SVIKEKDGKL
    PMC21     DFVRTYDTVE  FLSADTKTTT  VNVESKDNGK  KTEVKIGAKT  SVIKEKDGKL
    H38       DFVHTYDTVE  FLSADTKTTT  VNVESKDNGK  RTEVKIGAKT  SVIKEKDGKL
    P20       DFVRTYDTVE  FLSADTKTTT  VNVESKDNGK  RTEVKIGAKT  SVIKEKDGKL
    Z2491     DFVRTYDTVE  FLSADTKTTT  VNVESKDNGK  RTEVKIGAKT  SVIKEKDGKL
    H41       DFVRTYDTVE  FLSADTKTTT  VNVESKDNGK  KTEVKIGAKT  SVIKEKDGKL
Consensus     DFV-TYDTVE  FLSADTKTTT  VNVESKDNGK  -TEVKIGAKT  SVIKEKDGKL
                                           C5
```

FIG. 1B

```
              301                                                        350
     EG327   VTGKDKGEND  SSTDKGEGLV  TAKEVIDAVN  KAGWRMKTTT  ANGQTGQADK
     BZ198   VTGKGKDENG  SSTDEGEGLV  TAKEVIDAVN  KAGWRMKTTT  ANGQTGQADK
      BZ10   VTGKGKGENG  SSTDEGEGLV  TAKEVIDAVN  KAGWRMKTTT  ANGQTGQADK
       H15   VTGKGKDENG  SSTDEGEGLV  TAKEVIDAVN  KAGWRMKTTT  ANGQTGQADK
     EG329   VTGKDKGENG  SSTDEGEGLV  TAKEVIDAVN  KAGWRMKTTT  ANGQTGQADK
     PMC21   VTGKDKGENG  SSTDEGEGLV  TAKEVIDAVN  KAGWRMKTTT  ANGQTGQADK
       H38   VTGKGKGENG  SSTDEGEGLV  TAKEVIDAVN  KAGWRMKTTT  ANGQTGQADK
       P20   VTGKGKGENG  SSTDEGEGLV  TAKEVIDAVN  KAGWRMKTTT  ANGQTGQADK
     Z2491   VTGKGKGENG  SSTDEGEGLV  TAKEVIDAVN  KAGWRMKTTT  ANGQTGQADK
       H41   VTGKGKGENG  SSTDEGEGLV  TAKEVIDAVN  KAGWRMKTTT  ANGQTGQADK
 Consensus   VTGK-K-EN-  SSTD-GEGLV  TAKEVIDAVN  KAGWRMKTTT  ANGQTGQADK
                                          C5

351                                                        400
     EG327   FETVTSGTNV  TFASGKGTTA  TVSKDDQGNI  TVMYDVNVGD  ALNVNQLQNS
     BZ198   FETVTSGTNV  TFASGKGTTA  TVSKDDQGNI  TVKYDVNVGD  ALNVNQLQNS
      BZ10   FETVTSGTKV  TFASGNGTTA  TVSKDDQGNI  TVKYDVNVGD  ALNVNQLQNS
       H15   FETVTSGTKV  TFASGNGTTA  TVSKDDQGNI  TVKYDVNVGD  ALNVNQLQNS
     EG329   FETVTSGTNV  TFASGKGTTA  TVSKDDQGNI  TVMYDVNVGD  ALNVNQLQNS
     PMC21   FETVTSGTNV  TFASGKGTTA  TVSKDDQGNI  TVMYDVNVGD  ALNVNQLQNS
       H38   FETVTSGTNV  TFASGKGTTA  TVSKDDQGNI  TVKYDVNVGD  ALNVNQLQNS
       P20   FETVTSGTKV  TFASGNGTTA  TVSKDDQGNI  TVKYDVNVGD  ALNVNQLQNS
     Z2491   FETVTSGTNV  TFASGKGTTA  TVSKDDQGNI  TVMYDVNVGD  ALNVNQLQNS
       H41   FETVTSGTKV  TFASGNGTTA  TVSKDDQGNI  TVKYDVNVGD  ALNVNQLQNS
 Consensus   FETVTSGT-V  TFASG-GTTA  TVSKDDQGNI  TV-YDVNVGD  ALNVNQLQNS
                                          C5

401                                                        450
     EG327   GWNLDSKAVA  GSSGKVISGN  VSPSKGKMDE  TVNINAGNNI  EITRNGKNID
     BZ198   GWNLDSKAVA  GSSGKVISGN  VSPSKGKMDE  TVNINAGNNI  EITRNGKNID
      BZ10   GWNLDSKAVA  GSSGKVISGN  VSPSKGKMDE  TVNINAGNNI  EITRNGKNID
       H15   GWNLDSKAVA  GSSGKVISGN  VSPSKGKMDE  TVNINAGNNI  EITRNGKNID
     EG329   GWNLDSKAVA  GSSGKVISGN  VSPSKGKMDE  TVNINAGNNI  EITRNGKNID
     PMC21   GWNLDSKAVA  GSSGKVISGN  VSPSKGKMDE  TVNINAGNNI  EITRNGKNID
       H38   GWNLDSKAVA  GSSGKVISGN  VSPSKGKMDE  TVNINAGNNI  EITRNGKNID
       P20   GWNLDSKAVA  GSSGKVISGN  VSPSKGKMDE  TVNINAGNNI  EITRNGKNID
     Z2491   GWNLDSKAVA  GSSGKVISGN  VSPSKGKMDE  TVNINAGNNI  EISRNGKNID
       H41   GWNLDSKAVA  GSSGKVISGN  VSPSKGKMDE  TVNINAGNNI  EITRNGKNID
 Consensus   GWNLDSKAVA  GSSGKVISGN  VSPSKGKMDE  TVNINAGNNI  EI-RNGKNID
                                          C5
```

FIG. 1C

```
              451                                                500
      EG327   IATSMTPQFS  SVSLGAGADA  PTLSVDDEGA  LNVGSKDANK  PVRITNVAPG
      BZ198   IATSMAPQFS  SVSLGAGADA  PTLSVDDEGA  LNVGSKDTNK  PVRITNVAPG
       BZ10   IATSMTPQFS  SVSLGAGADA  PTLSVDDEGA  LNVGSKDANK  PVRITNVAPG
        H15   IATSMTPQFS  SVSLGAGADA  PTLSVDDEGA  LNVGSKDANK  PVRITNVAPG
      EG329   IATSMTPQFS  SVSLGAGADA  PTLSVDG.DA  LNVGSKKDNK  PVRITNVAPG
      PMC21   IATSMTPQFS  SVSLGAGADA  PTLSVDG.DA  LNVGSKKDNK  PVRITNVAPG
        H38   IATSMTPQFS  SVSLGAGADA  PTLSVDDKGA  LNVGSKDANK  PVRITNVAPG
        P20   IATSMTPQFS  SVSLGAGADA  PTLSVDDEGA  LNVGSKDANK  PVRITNVAPG
      Z2491   IATSMAPQFS  SVSLGAGADA  PTLSVDDEGA  LNVGSKDANK  PVRITNVAPG
        H41   IATSMTPQFS  SVSLGAGADA  PTLSVDDEGA  LNVGSKDANK  PVRITNVAPG
  Consensus   IATSM-PQFS  SVSLGAGADA  PTLSVD---A  LNVGSK--NK  PVRITNVAPG
                                          C5

501                                                550
      EG327   VKEGDVTNVA  QLKGVAQNLN  NHIDNVDGNA  RAGIAQAIAT  AGLVQAYLPG
      BZ198   VKEGDVTNVA  QLKGVAQNLN  NRIDNVDGNA  RAGIAQAIAT  AGLVQAYLPG
       BZ10   VKEGDVTNVA  QLKGVAQNLN  NRIDNVDGNA  RAGIAQAIAT  AGLAQAYLPG
        H15   VKEGDVTNVA  QLKGVAQNLN  NRIDNVDGNA  RAGIAQAIAT  AGLAQAYLPG
      EG329   VKEGDVTNVA  QLKGVAQNLN  NRIDNVDGNA  RAGIAQAIAT  AGLVQAYLPG
      PMC21   VKEGDVTNVA  QLKGVAQNLN  NRIDNVDGNA  RAGIAQAIAT  AGLVQAYLPG
        H38   VKEGDVTNVA  QLKGVAQNLN  NRIDNVDGNA  RAGIAQAIAT  AGLVQAYLPG
        P20   VKEGDVTNVA  QLKGVAQNLN  NRIDNVNGNA  RAGIAQAIAT  AGLAQAYLPG
      Z2491   VKEGDVTNVA  QLKGVAQNLN  NRIDNVDGNA  RAGIAQAIAT  AGLVQAYLPG
        H41   VKEGDVTNVA  QLKGVAQNLN  NRIDNVNGNA  RAGIAQAIAT  AGLVQAYLPG
  Consensus   VKEGDVTNVA  QLKGVAQNLN  N-IDNV-GNA  RAGIAQAIAT  AGL-QAYLPG
                                          C5

551                                                600
      EG327   KSMMAIGGGT  YRGEAGYAIG  YSSISDGGNW  IIKGTASGNS  RGHFGASASV
      BZ198   KSMMAIGGDT  YRGEAGYAIG  YSSISDGGNW  IIKGTASGNS  RGHFGASASV
       BZ10   KSMMAIGGGT  YRGEAGYAIG  YSSISDTGNW  VIKGTASGNS  RGHFGTSASV
        H15   KSMMAIGGGT  YRGEAGYAIG  YSSISDTGNW  VIKGTASGNS  RGHFGASASV
      EG329   KSMMAIGGGT  YRGEAGYAIG  YSSISDGGNW  IIKGTASGNS  RGHFGASASV
      PMC21   KSMMAIGGGT  YRGEAGYAIG  YSSISDGGNW  IIKGTASGNS  RGHFGASASV
        H38   KSMMAIGGGT  YRGEAGYAIG  YSSISDTGNW  VIKGTASGNS  RGHFGTSASV
        P20   KSMMAIGGGT  YLGEAGYAIG  YSSISDGGNW  IIKGTASGNS  RGHFGASASV
      Z2491   KSMMAIGGGT  YRGEAGYAIG  YSSISDGGNW  IIKGTASGNS  RGHFGASASV
        H41   KSMMAIGGGT  YLGEAGYAIG  YSSISAGGNW  IIKGTASGNS  RGHFGASASV
  Consensus   KSMMAIGG-T  Y-GEAGYAIG  YSSIS--GNW  -IKGTASGNS  RGHFG-SASV
                                          C5
```

FIG. 1D

```
              601
    EG327     GYQW.
    BZ198     GYQW.
     BZ10     GYQW.
      H15     GYQW.
    EG329     GYQW.
    PMC21     GYQW.
      H38     GYQW.
      P20     GYQW.
    Z2491     GYQW.
      H41     GYQW.
Consensus     GYQW.
               C5
```

FIG. 1E

```
            1                                                                        70
    H15   ATGAACAAAA TATACCGCAT CATTTGGAAT AGTGCCCTCA ATGCCTGGGT CGTCGTATCC GAGCTCACAC
    BZ10  ATGAACAAAA TATCCCGCAT CATTTGGAAT AGTGCCCTCA ATGCCTGGGT CGTCGTATCC GAGCTCACAC
    BZ198 ATGAACAAAA TATACCGCAT CATTTGGAAT AGTGCCCTCA ATGCCTGGGT CGTCGTATCC GAGCTCACAC
    P20   ATGAACAAAA TATACCGCAT CATTTGGAAT AGTGCCCTCA ATGCCTGGGT AGTCGTATCC GAGCTCACAC
    H38   ATGAACAAAA TATACCGCAT CATTTGGAAT AGTGCCCTCA ATGCCTGGGT CGCCGTATCC GAGCTCACAC
    Z2491 ATGAACAAAA TATACCGCAT CATTTGGAAT AGTGCCCTCA ATGCCTGGGT CGCCGTATCC GAGCTCACAC
    H41   ATGAACGAAA TATACCGCAT CATTTGGAAT AGTGCCCTCA ATGCCTGGGT CGCCGTATCC GAGCTCACAC
    EG329 ATGAACGAAA TATTGCGCAT CATTTGGAAT AGCGCCCTCA ATGCCTGGGT CGTTGTATCC GAGCTCACAC
    PMC21 ATGAACAAAA TATACCGCAT CATTTGGAAT AGTGCCCTCA ATGCATGGGT CGTCGTATCC GAGCTCACAC
    EG327 ATGAACAAAA TATACCGCAT CATTTGGAAT AGTGCCCTCA ATGCCTGGGT CGCCGTATCC GAGCTCACAC
Consensus ATGAAC-AAA TAT--CGCAT CATTTGGAAT AG-GCCCTCA ATGC-TGGGT -G--GTATCC GAGCTCACAC
                                                C1

71                                                                       140
    H15   GCAACCACAC CAAACGCGCC TCCGCAACCG TGGCGACCGC CGTATTGGCG ACACTGTTGT TTGCAACGGT
    BZ10  GCAACCACAC CAAACGCGCC TCCGCAACCG TGGCGACCGC CGTATTGGCG ACACTGTTGT TTGCAACGGT
    BZ198 GCAACCACAC CAAACGCGCC TCCGCAACCG TGGCGACCGC CGTATTGGCG ACACTGTTGT TTGCAACGGT
    P20   GCAACCACAC CAAACGCGCC TCCGCAACCG TGGCGACCGC CGTATTGGCG ACACTGCTGT CCGCAACGGT
    H38   GCAACCACAC CAAACGCGCC TCCGCAACCG TGAAGACCGC CGTATTGGCG ACGCTGTTGT TTGCAACGGT
    Z2491 GCAACCACAC CAAACGCGCC TCCGCAACCG TGAAGACCGC CGTATTGGCG ACACTGTTGT TTGCAACGGT
    H41   GCAACCACAC CAAACGCGCC TCCGCAACCG TGAAGACCGC CGTATTGGCG ACACTGTTGT TTGCAACGGT
    EG329 GCAACCACAC CAAACGCGCC TCCGCAACCG TGAAGACCGC CGTATTGGCG ACTCTGTTGT TTGCAACGGT
    PMC21 GCAACCACAC CAAACGCGCC TCCGCAACCG TGAAGACCGC CGTATTGGCG ACTCTGTTGT TTGCAACGGT
    EG327 GCAACCACAC CAAACGCGCC TCCGCAACCG TGGCGACCGC CGTATTGGCG ACACTGTTGT TTGCAACGGT
Consensus GCAACCACAC CAAACGCGCC TCCGCAACCG TG--GACCGC CGTATTGGCG AC-CTG-TGT --GCAACGGT
                                                C1

141                                                                      210
    H15   TCAGGCGAAT GCTACCGATG ACGAC..... ....GATTTA TATTTAGAAC CCGTACAACG CACTGCTGTC
    BZ10  TCAGGCGAAT GCTACCGATG ACGAC..... ....GATTTA TATTTAGAAC CCGTACAACG CACTGCTGTC
    BZ198 TCAGGCGAAT GCTACCGATG ACGAC..... ....GATTTA TATTTAGAAC CCGTACAACG CACTGCTGTC
    P20   TCAGGCGAAT GCTACCGATA CCGAT..... .GAAGATGAA GAGTTAGAAT CCGTAGCACG CTCTGCTCTG
    H38   TCAGGCGAAT GCTACCGATG AAGAT..... .GAAGAAGAA GAGTTAGAAC CCGTAGTACG CTCTGCTCTG
    Z2491 TCAGGCGAAT GCTACCGATG AAGAT..... .GAAGAAGAA GAGTTAGAAT CCGTACAACG CTCTGTCGTA
    H41   TCAGGCGAAT GCTACCGATG AAGAT..... .GAAGAAGAA GAGTTAGAAT CCGTACAACG CTCTG...TC
    EG329 TCAGGCAAGT GCTAACAATG AAGAGCAAGA AGAAGATTTA TATTTAGACC CCGTGCTACG CACTGTTGCC
    PMC21 TCAGGCAAGT GCTAACAATG AAGAGCAAGA AGAAGATTTA TATTTAGACC CCGTACAACG CACTGTTGCC
    EG327 TCAGGCGAGT ACTACCGATG ACGAC..... ....GATTTA TATTTAGAAC CCGTACAACG CACTGCTGTC
Consensus TCAGGC-A-T -CTA-C-AT- --GA------ ----GA---A -A-TTAGA-- CCGT---ACG C-CTG-----
           C1                                         V1
```

FIG. 2A

```
              211                                                                            280
       H15   GTGTTGAGCT  TCCGTTCCGA  TAAAGAAGGC  ACGGGAGAAA  AAGAAGGTAC  AGAAGA...T  TCAAATTGGG
      BZ10   GTGTTGAGCT  TCCGTTCCGA  TAAAGAAGGC  ACGGGAGAAA  AAGAAGGTAC  AGAAGA...T  TCAAATTGGG
     BZ198   GTGTTGAGCT  TCCGTTCCGA  TAAAGAAGGC  ACGGGAGAAA  AAGAAGGTAC  AGAAGA...T  TCAAATTGGG
       P20   GTGTTGCAAT  TCATGATCGA  TAAAGAAGGC  AATGGAGAAA  TCGAATCTAC  AGGAGA...T  ATAGGTTGGA
       H38   GTGTTGCAAT  TCATGATCGA  TAAAGAAGGC  AATGGAGAAA  ACGAATCTAC  AGGAAA...T  ATAGGTTGGA
     Z2491   GGG..AGCAT  TCAAG.CCAG  TATGGAAGGC  AGCGGCGAAT  TGGAAACGAT  ATCAT....T  ATCAATGACT
       H41   GTAGGGAGCA  TTCAAGCCAG  TATGGAAGGC  AGCGTCGAAT  TGGAAACGAT  A.........  TCATTATCAA
     EG329   GTGTTGATAG  TCAATTCCGA  TAAAGAAGGC  ACGGGAGAAA  AAGAAAAAGT  AGAAGAAAAT  TCAGATTGGG
     PMC21   GTGTTGATAG  TCAATTCCGA  TAAAGAAGGC  ACGGGAGAAA  AAGAAAAAGT  AGAAGAAAAT  TCAGATTGGG
     EG327   GTGTTGAGCT  TCCGTTCCGA  TAAAGAAGGC  ACGGGAGAAA  AAGAAGTTAC  AGAAGA...T  TCAAATTGGG
 Consensus   G---------  T------C--  TA--GAAGGC  A--G--GAA-  --GAA-----  A---------  ----------
                                                 V1

281                                                                            350
       H15   CAGTATATTT  CGACGAGAAA  AGAGTACTAA  AAGCCGGAGC  AATCACCCTC  AAAGCCGGCG  ACAACCTGAA
      BZ10   CAGTATATTT  CGACGAGAAA  AGAGTACTAA  AAGCCGGAGC  AATCACCCTC  AAAGCCGGCG  ACAACCTGAA
     BZ198   CAGTATATTT  CGACGAGAAA  AGAGTACTAA  AAGCCGGAGC  AATCACCCTC  AAAGCCGGCG  ACAACCTGAA
       P20   GTATATATTA  CGACGATCAC  AACACTCTAC  ACGGCGCAAC  CGTTACCCTC  AAAGCCGGCG  ACAACCTGAA
       H38   GTATATATTA  CGACAATCAC  AACACTCTAC  ACGGCGCAAC  CGTTACCCTC  AAAGCCGGCG  ACAACCTGAA
     Z2491   AACGACAGCA  AGGAATTTGT  AGACCCATAC  ATAGTA....  .GTTACCCTC  AAAGCCGGCG  ACAACCTGAA
       H41   TGACTAACGA  CAGCAAGGAA  TTTGTAGACC  CATACATAGT  AGTTACCCTC  AAAGCCGGCG  ACAACCTGAA
     EG329   CAGTATATTT  CAACGAGAAA  GGAGTACTAA  CAGCCAGAGA  AATCACCCTC  AAAGCCGGCG  ACAACCTGAA
     PMC21   CAGTATATTT  CAACGAGAAA  GGAGTACTAA  CAGCCAGAGA  AATCACCCTC  AAAGCCGGCG  ACAACCTGAA
     EG327   GAGTATATTT  CGACAAGAAA  GGAGTACTAA  CAGCCGGAAC  AATCACCCTC  AAAGCCGGCG  ACAACCTGAA
 Consensus   ------A---  ----------  ----------  ----------  --T-ACCCTC  AAAGCCGGCG  ACAACCTGAA
                                    V1                                C2

351                                                                            420
       H15   AATCAAACAA  AACACCAATG  AAAACACCAA  TGAAAACACC  AATGACAGTA  GCTTCACCTA  CTCCCTGAAA
      BZ10   AATCAAACAA  AACACCAATG  AAAACACCAA  TGAAAACACC  AATGACAGTA  GCTTCACCTA  CTCCCTGAAA
     BZ198   AATCAAACAA  AACACCAATG  AAAACACC..  ..........  AATGACAGTA  GCTTCACCTA  CTCCCTGAAA
       P20   AATCAAACAA  AGCGGCAAAG  A.........  ..........  ..........  .CTTCACCTA  CTCGCTGAAA
       H38   AATCAAACAA  AACACCAATA  AAAACACCAA  TGAAAACACC  AATGACAGTA  GCTTCACCTA  CTCGCTGAAA
     Z2491   AATCAAACAA  AACACCAATG  AAAACACC..  ..........  AATGCCAGTA  GCTTCACCTA  CTCGCTGAAA
       H41   AATCAAACAA  AACACCAATG  AAAACACC..  ..........  AATGCCAGTA  GCTTCACCTA  CTCGCTGAAA
     EG329   AATCAAACAA  AAC.......  ........G.  ..........  ....GCACAA  ACTTCACCTA  CTCGCTGAAA
     PMC21   AATCAAACAA  AAC.......  ........G.  ..........  ....GCACAA  ACTTCACCTA  CTCGCTGAAA
     EG327   AATCAAACAA  AACACCAATG  AAAACACC..  ..........  AATGCCAGTA  GCTTCACCTA  CTCGCTGAAA
 Consensus   AATCAAACAA  A-C-------  ----------  ----------  ----------  -CTTCACCTA  CTC-CTGAAA
                 C2                              V2                               C3
```

FIG. 2B

```
         421                                                                      490
   H15   AAAGACCTCA CAGATCTGAC CAGTGTTGAA ACTGAAAAAT TATCGTTTGG CGCAAACGGT AATAAAGTCA
   BZ10  AAAGACCTCA CAGATCTGAC CAGTGTTGAA ACTGAAAAAT TATCGTTTGG CGCAAACGGT AATAAAGTCA
   BZ198 AAAGACCTCA CAGATCTGAC CAGTGTTGAA ACTGAAAAAT TATCGTTTGG CGCAAACGGT AATAAAGTCA
   P20   AAAGAGCTGA AAGACCTGAC CAGTGTTGAA ACTGAAAAAT TATCGTTTGG CGCAAACGGT AATAAAGTCA
   H38   AAAGACCTCA CAGATCTGAC CAGTGTTGAA ACTGAAAAAT TATCGTTTGG CGCAAACGGC AATAAAGTCA
   Z2491 AAAGACCTCA CAGGCCTGAT CAATGTTGAA ACTGAAAAAT TATCGTTTGG CGCAAACGGC AAGAAAGTCA
   H41   AAAGACCTCA CAGGCCTGAT CAATGTTGAA ACTGAAAAAT TATCGTTTGG CGCAAACGGC AAGAAAGTCA
   EG329 AAAGACCTCA CAGATCTGAC CAGTGTTGGA ACTGAAAAAT TATCGTTTAG CGCAAACGGC AATAAAGTCA
   PMC21 AAAGACCTCA CAGATCTGAC CAGTGTTGGA ACTGAAAAAT TATCGTTTAG CGCAAACGGC AATAAAGTCA
   EG327 AAAGACCTCA CAGATCTGAC CAGTGTTGGA ACTGAAAAAT TATCGTTTAG CGCAAACAGC AATAAAGTCA
Consensus AAAGA-CT-A -AG--CTGA- CA-TGTTG-A ACTGAAAAAT TATCGTTT-G CGCAAAC-G- AA-AAAGTCA
                                              C3

491                                                                      560
   H15   ACATCACAAG CGACACCAAA GGCTTGAATT TTGCGAAAGA AACGGCTGGG ACGAACGGCG ACCCCACGGT
   BZ10  ACATCACAAG CGACACCAAA GGCTTGAATT TTGCGAAAGA AACGGCTGGG ACGAACGGCG ACCCCACGGT
   BZ198 ACATCACAAG CGACACCAAA GGCTTGAATT TTGCGAAAGA AACGGCTGGG ACGAACGGCG ACCCCACGGT
   P20   ACATCACAAG CGACACCAAA GGCTTGAATT TTGCGAAAGA AACGGCTGGG ACGAACGGCG ACCCCACGGT
   H38   ACATCACAAG CGACACCAAA GGCTTGAATT TCGCGAAAGA AACGGCTGGG ACGAACGGCG ACACCACGGT
   Z2491 ACATCATAAG CGACACCAAA GGCTTGAATT TCGCGAAAGA AACGGCTGGG ACGAACGGCG ACACCACGGT
   H41   ACATCATAAG CGACACCAAA GGCTTGAATT TCGCGAAAGA AACGGCTGGG ACGAACGGCG ACACCACGGT
   EG329 ACATCACAAG CGACACCAAA GGCTTGAATT TTGCGAAAGA AACGGCTGGG ACGAACGGCG ACACCACGGT
   PMC21 ACATCACAAG CGACACCAAA GGCTTGAATT TTGCGAAAGA AACGGCTGGG ACGAACGGCG ACACCACGGT
   EG327 ACATCACAAG CGACACCAAA GGCTTGAATT TCGCGAAAAA AACGGCTGAG ACCAACGGCG ACACCACGGT
Consensus ACATCA-AAG CGACACCAAA GGCTTGAATT T-GCGAAA-A AACGGCTG-G AC-AACGGCG AC-CCACGGT
                                              C3

561                                                                      630
   H15   TCATCTGAAC GGTATCGGTT CGACTTTGAC CGATACGCTG CTGAATACCG GAGCGACCAC AAACGTAACC
   BZ10  TCATCTGAAC GGTATCGGTT CGACTTTGAC CGATACGCTG CTGAATACCG GAGCGACCAC AAACGTAACC
   BZ198 TCATCTGAAC GGTATCGGTT CGACTTTGAC CGATACGCTG CTGAATACCG GAGCGACCAC AAACGTAACC
   P20   TCATCTGAAC GGTATCGGTT CGACTTTGAC CGATACGCTT GCGGGTTCTT CTGCTTCTCA CGTTGATGCG
   H38   TCATCTGAAC GGTATTGGTT CGACTTTGAC CGATACGCTG CTGAATACCG GAGCGACCAC AAACGTAACC
   Z2491 TCATCTGAAC GGTATCGGTT CGACTTTGAC CGATACGCTT GCGGGTTCTT CTGCTTCTCA CGTTGATGCG
   H41   TCATCTGAAC GGTATCGGTT CGACTTTGAC CGATATGCTG CTGAATACCG GAGCGACCAC AAACGTAACC
   EG329 TCATCTGAAC GGTATTGGTT CGACTTTGAC CGATACGCTG CTGAATACCG GAGCGACCAC AAACGTAACC
   PMC21 TCATCTGAAC GGTATTGGTT CGACTTTGAC CGATACGCTG CTGAATACCG GAGCGACCAC AAACGTAACC
   EG327 TCATCTGAAC GGTATCGGTT CGACTTTGAC CGATACGCTG CTGAATACCG GAGCGACCAC AAACGTAACC
Consensus TCATCTGAAC GGTAT-GGTT CGACTTTGAC CGATA-GCT- --G--T-C-- --GC--C--- ----G---C-
                      C3                                        V3
```

*FIG. 2C*

```
              631                                                              700
       H15  AACGACAACG TTACCGATGA CGAGAAAAAA CGTGCGGCAA GCGTTAAAGA CGTATTAAAC GCAGGCTGGA
      BZ10  AACGACAACG TTACCGATGA CGAGAAAAAA CGTGCGGCAA GCGTTAAAGA CGTATTAAAC GCAGGCTGGA
     BZ198  AACGACAACG TTACCGATGA CGAGAAAAAA CGTGCGGCAA GCGTTAAAGA CGTATTAAAC GCAGGCTGGA
       P20  GGTAACCAAA GTACACATTA C......ACT CGTGCAGCAA GTATTAAGGA TGTGTTGAAT GCGGGTTGGA
       H38  AACGACAACG TTACCGATGA CAAGAAAAAA CGTGCGGCAA GCGTTAAAGA CGTATTAAAC GCAGGCTGGA
     Z2491  GGTAACCAAA GTACACATTA C......ACT CGTGCAGCAA GTATTAAGGA TGTGTTGAAT GCGGGTTGGA
       H41  AACGACAACG TTACCGATGA CGAGAAAAAA CGTGCGGCAA GCGTTAAAGA CGTATTAAAC GCAGGCTGGA
     EG329  AACGACAACG TTACCGATGA CGAGAAAAAA CGTGCGGCAA GCGTTAAAGA CGTATTAAAC GCTGGCTGGA
     PMC21  AACGACAACG TTACCGATGA CGAGAAAAAA CGTGCGGCAA GCGTTAAAGA CGTATTAAAC GCTGGCTGGA
     EG327  AACGACAACG TTACCGATGA CGAGAAAAAA CGTGCGGCAA GCGTTAAAGA CGTATTAAAC GCAGGCTGGA
 Consensus  ----AC-A-- -TAC--AT-A C------A-- CGTGC-GCAA G--TTAA-GA -GT-TT-AA- GC-GG-TGGA
                 V3                                              C4

701                                                              770
       H15  ACATTAAAGG CGTTAAACCC GGTACAACAG CT......TC CGATAACGTT GATTTCGTCC GCACTTACGA
      BZ10  ACATTAAAGG CGTTAAACCC GGTACAACAG CT......TC CGATAACGTT GATTTCGTCC GCACTTACGA
     BZ198  ACATTAAAGG CGTTAAACCC GGTACAACAG CT......TC CGATAACGTT GATTTCGTCC GCACTTACGA
       P20  ATATTAAGGG TGTTAAAACT GGCTCAACAA CTGGTCAATC AGAAAATGTC GATTTCGTCC GCACTTACGA
       H38  ACATTAAAGG CGTTAAACCC GGTACAACAG CT......TC CGATAACGTT GATTTCGTCC ACACTTACGA
     Z2491  ATATTAAGGG TGTTAAAACT GGCTCAACAA CTGGTCAATC AGAAAATGTC GATTTCGTCC GCACTTACGA
       H41  ACATTAAAGG CGTTAAACCC GGTACAACAG CT......TC CGATAACGTT GATTTCGTCC GCACTTACGA
     EG329  ACATTAAAGG CGTTAAACCC GGTACAACAG CT......TC CGATAACGTT GATTTCGTCC GCACTTACGA
     PMC21  ACATTAAAGG CGTTAAACCC GGTACAACAG CT......TC CGATAACGTT GATTTCGTCC GCACTTACGA
     EG327  ACATTAAAGG CGTTAAACCC GGTACAACAG CT......TC CGATAACGTT GATTTCGTCC GCACTTACGA
 Consensus  A-ATTAA-GG -GTTAAA-C- GG--CAACA- CT------TC -GA-AA-GT- GATTTCGTCC -CACTTACGA
                 C4                       V4                              C5

771                                                              840
       H15  CACAGTCGAG TTCTTGAGCG CAGATACGAA AACAACGACT GTTAATGTGG AAAGCAAAGA CAACGGCAAG
      BZ10  CACAGTCGAG TTCTTGAGCG CAGATACGAA AACAACGACT GTTAATGTGG AAAGCAAAGA CAACGGCAAG
     BZ198  CACAGTCGAG TTCTTGAGCG CAGATACGAA AACAACGACT GTTAATGTGG AAAGCAAAGA CAACGGCAAG
       P20  CACAGTCGAG TTCTTGAGCG CAGATACGAA AACAACGACT GTTAATGTGG AAAGCAAAGA CAACGGCAAG
       H38  CACAGTCGAG TTCTTGAGCG CAGATACGAA AACAACGACT GTTAATGTGG AAAGCAAAGA CAACGGCAAG
     Z2491  CACAGTCGAG TTCTTGAGCG CAGATACGAA AACAACGACT GTTAATGTGG AAAGCAAAGA CAACGGCAAG
       H41  CACAGTCGAG TTCTTGAGCG CAGATACGAA AACAACGACT GTTAATGTGG AAAGCAAAGA CAACGGCAAG
     EG329  CACAGTCGAG TTCTTGAGCG CAGATACGAA AACAACGACT GTTAATGTGG AAAGCAAAGA CAACGGCAAG
     PMC21  CACAGTCGAG TTCTTGAGCG CAGATACGAA AACAACGACT GTTAATGTGG AAAGCAAAGA CAACGGCAAG
     EG327  CACAGTCGAG TTCTTGAGCG CAGATACGAA AACAACGACT GTTAATGTGG AAAGCAAAGA CAACGGCAAG
 Consensus  CACAGTCGAG TTCTTGAGCG CAGATACGAA AACAACGACT GTTAATGTGG AAAGCAAAGA CAACGGCAAG
                                                C5

841                                                              910
       H15  AAAACCGAAG TTAAAATCGG TGCGAAGACT TCTGTTATTA AAGAAAAAGA CGGTAAGTTG GTTACTGGTA
      BZ10  AGAACCGAAG TTAAAATCGG TGCGAAGACT TCTGTTATTA AAGAAAAAGA CGGTAAGTTG GTTACTGGTA
     BZ198  AAAACCGAAG TTAAAATCGG TGCGAAGACT TCTGTTATTA AAGAAAAAGA CGGTAAGTTG GTTACTGGTA
       P20  AGAACCGAAG TTAAAATCGG TGCGAAGACT TCTGTTATTA AAGAAAAAGA CGGTAAGTTG GTTACTGGTA
       H38  AGAACCGAAG TTAAAATCGG TGCGAAGACT TCTGTTATTA AAGAAAAAGA CGGTAAGTTG GTTACTGGTA
     Z2491  AGAACCGAAG TTAAAATCGG TGCGAAGACT TCTGTTATTA AAGAAAAAGA CGGTAAGTTG GTTACTGGTA
       H41  AAAACCGAAG TTAAAATCGG TGCGAAGACT TCTGTTATTA AAGAAAAAGA CGGTAAGTTG GTTACTGGTA
     EG329  AAAACCGAAG TTAAAATCGG TGCGAAGACT TCTGTTATTA AAGAAAAAGA CGGTAAGTTG GTTACTGGTA
     PMC21  AAAACCGAAG TTAAAATCGG TGCGAAGACT TCTGTTATTA AAGAAAAAGA CGGTAAGTTG GTTACTGGTA
     EG327  AGAACCGAAG TTAAAATCGG TGCGAAGACT TCTGTTATCA AAGAAAAAGA CGGTAAGTTG GTTACTGGTA
 Consensus  A-AACCGAAG TTAAAATCGG TGCGAAGACT TCTGTTAT-A AAGAAAAAGA CGGTAAGTTG GTTACTGGTA
                                                C5
```

FIG. 2D

```
            911                                                                    980
      H15   AAGGCAAAGA CGAGAATGGT TCTTCTACAG ACGAAGGCGA AGGCTTAGTG ACTGCAAAAG AAGTGATTGA
     BZ10   AAGGCAAAGG CGAGAATGGT TCTTCTACAG ACGAAGGCGA AGGCTTAGTG ACTGCAAAAG AAGTGATTGA
    BZ198   AAGGCAAAGA CGAGAATGGT TCTTCTACAG ACGAAGGCGA AGGCTTAGTG ACTGCAAAAG AAGTGATTGA
      P20   AAGGCAAAGG CGAGAATGGT TCTTCTACAG ACGAAGGCGA AGGCTTAGTG ACTGCAAAAG AAGTGATTGA
      H38   AAGGCAAAGG CGAGAATGGT TCTTCTACAG ACGAAGGCGA AGGCTTAGTG ACTGCAAAAG AAGTGATTGA
    Z2491   AAGGCAAAGG CGAGAATGGT TCTTCTACAG ACGAAGGCGA AGGCTTAGTG ACTGCAAAAG AAGTGATTGA
      H41   AAGGCAAAGG CGAGAATGGT TCTTCTACAG ACGAAGGCGA AGGCTTAGTG ACTGCAAAAG AAGTGATTGA
    EG329   AAGACAAAGG CGAGAATGGT TCTTCTACAG ACGAAGGCGA AGGCTTAGTG ACTGCAAAAG AAGTGATTGA
    PMC21   AAGACAAAGG CGAGAATGGT TCTTCTACAG ACGAAGGCGA AGGCTTAGTG ACTGCAAAAG AAGTGATTGA
    EG327   AAGACAAAGG CGAGAATGAT TCTTCTACAG ACAAAGGCGA AGGCTTAGTG ACTGCAAAAG AAGTGATTGA
Consensus   AAG-CAAAG- CGAGAATG-T TCTTCTACAG AC-AAGGCGA AGGCTTAGTG ACTGCAAAAG AAGTGATTGA
                                                   C5

981                                                                   1050
      H15   TGCAGTAAAC AAGGCTGGTT GGAGAATGAA AACAACAACC GCTAATGGTC AAACAGGTCA AGCTGACAAG
     BZ10   TGCAGTAAAC AAGGCTGGTT GGAGAATGAA AACAACAACC GCTAATGGTC AAACAGGTCA AGCTGACAAG
    BZ198   TGCAGTAAAC AAGGCTGGTT GGAGAATGAA AACAACAACC GCTAATGGTC AAACAGGTCA AGCTGACAAG
      P20   TGCAGTAAAC AAGGCTGGTT GGAGAATGAA AACAACAACC GCTAATGGTC AAACAGGTCA AGCTGACAAG
      H38   TGCAGTAAAC AAGGCTGGTT GGAGAATGAA AACAACAACC GCTAATGGTC AAACAGGTCA AGCTGACAAG
    Z2491   TGCAGTAAAC AAGGCTGGTT GGAGAATGAA AACAACAACC GCTAATGGTC AAACAGGTCA AGCTGACAAG
      H41   TGCAGTAAAC AAGGCTGGTT GGAGAATGAA AACAACAACC GCTAATGGTC AAACAGGTCA AGCTGACAAG
    EG329   TGCAGTAAAC AAGGCTGGTT GGAGAATGAA AACAACAACC GCTAATGGTC AAACAGGTCA AGCTGACAAG
    PMC21   TGCAGTAAAC AAGGCTGGTT GGAGAATGAA AACAACAACC GCTAATGGTC AAACAGGTCA AGCTGACAAG
    EG327   TGCAGTAAAC AAGGCTGGTT GGAGAATGAA AACAACAACC GCTAATGGTC AAACAGGTCA AGCTGACAAG
Consensus   TGCAGTAAAC AAGGCTGGTT GGAGAATGAA AACAACAACC GCTAATGGTC AAACAGGTCA AGCTGACAAG
                                                   C5

1051                                                                  1120
      H15   TTTGAAACCG TTACATCAGG CACAAAAGTA ACCTTTGCTA GTGGTAATGG TACAACTGCG ACTGTAAGTA
     BZ10   TTTGAAACCG TTACATCAGG CACAAAAGTA ACCTTTGCTA GTGGTAATGG TACAACTGCG ACTGTAAGTA
    BZ198   TTTGAAACCG TTACATCAGG CACAAATGTA ACCTTTGCTA GTGGTAAAGG TACAACTGCG ACTGTAAGTA
      P20   TTTGAAACCG TTACATCAGG CACAAAAGTA ACCTTTGCTA GTGGTAATGG TACAACTGCG ACTGTAAGTA
      H38   TTTGAAACCG TTACATCAGG CACAAATGTA ACCTTTGCTA GTGGTAAAGG TACAACTGCG ACTGTAAGTA
    Z2491   TTTGAAACCG TTACATCAGG CACAAATGTA ACCTTTGCTA GTGGTAAAGG TACAACTGCG ACTGTAAGTA
      H41   TTTGAAACCG TTACATCAGG CACAAAAGTA ACCTTTGCTA GTGGTAATGG TACAACTGCG ACTGTAAGTA
    EG329   TTTGAAACCG TTACATCAGG CACAAATGTA ACCTTTGCTA GTGGTAAAGG TACAACTGCG ACTGTAAGTA
    PMC21   TTTGAAACCG TTACATCAGG CACAAATGTA ACCTTTGCTA GTGGTAAAGG TACAACTGCG ACTGTAAGTA
    EG327   TTTGAAACCG TTACATCAGG CACAAATGTA ACCTTTGCTA GTGGTAAAGG TACAACTGCG ACTGTAAGTA
Consensus   TTTGAAACCG TTACATCAGG CACAAA-GTA ACCTTTGCTA GTGGTAA-GG TACAACTGCG ACTGTAAGTA
                                                   C5

1121                                                                  1190
      H15   AAGATGATCA AGGCAACATC ACTGTTAAGT ATGATGTAAA TGTCGGCGAT GCCCTAAACG TCAATCAGCT
     BZ10   AAGATGATCA AGGCAACATC ACTGTTAAGT ATGATGTAAA TGTCGGCGAT GCCCTAAACG TCAATCAGCT
    BZ198   AAGATGATCA AGGCAACATC ACTGTTAAGT ATGATGTAAA TGTCGGCGAT GCCCTAAACG TCAATCAGCT
      P20   AAGATGATCA AGGCAACATC ACTGTTAAGT ATGATGTAAA TGTCGGCGAT GCCCTAAACG TCAATCAGCT
      H38   AAGATGATCA AGGCAACATC ACTGTTAAGT ATGATGTAAA TGTCGGCGAT GCCCTAAACG TCAATCAGCT
    Z2491   AAGATGATCA AGGCAACATC ACTGTTATGT ATGATGTAAA TGTCGGCGAT GCCCTAAACG TCAATCAGCT
      H41   AAGATGATCA AGGCAACATC ACTGTTAAGT ATGATGTAAA TGTCGGCGAT GCCCTAAACG TCAATCAGCT
    EG329   AAGATGATCA AGGCAACATC ACTGTTATGT ATGATGTAAA TGTCGGCGAT GCCCTAAACG TCAATCAGCT
    PMC21   AAGATGATCA AGGCAACATC ACTGTTATGT ATGATGTAAA TGTCGGCGAT GCCCTAAACG TCAATCAGCT
    EG327   AAGATGATCA AGGCAACATC ACTGTTATGT ATGATGTAAA TGTCGGCGAT GCCCTAAACG TCAATCAGCT
Consensus   AAGATGATCA AGGCAACATC ACTGTTA-GT ATGATGTAAA TGTCGGCGAT GCCCTAAACG TCAATCAGCT
                                                   C5
```

*FIG. 2E*

```
              1191                                                                    1260
       H15   GCAAAACAGC GGTTGGAATT TGGATTCCAA AGCGGTTGCA GGTTCTTCGG GCAAAGTCAT CAGCGGCAAT
       BZ10  GCAAAACAGC GGTTGGAATT TGGATTCCAA AGCGGTTGCA GGTTCTTCGG GCAAAGTCAT CAGCGGCAAT
       BZ198 GCAAAACAGC GGTTGGAATT TGGATTCCAA AGCGGTTGCA GGTTCTTCGG GCAAAGTCAT CAGCGGCAAT
       P20   GCAAAACAGC GGTTGGAATT TGGATTCCAA AGCGGTTGCA GGTTCTTCGG GCAAAGTCAT CAGCGGCAAT
       H38   GCAAAACAGC GGTTGGAATT TGGATTCCAA AGCGGTTGCA GGTTCTTCGG GCAAAGTCAT CAGCGGCAAT
       Z2491 GCAAAACAGC GGTTGGAATT TGGATTCCAA AGCGGTTGCA GGTTCTTCGG GCAAAGTCAT CAGCGGCAAT
       H41   GCAAAACAGC GGTTGGAATT TGGATTCCAA AGCGGTTGCA GGTTCTTCGG GCAAAGTCAT CAGCGGCAAT
       EG329 GCAAAACAGC GGTTGGAATT TGGATTCCAA AGCGGTTGCA GGTTCTTCGG GCAAAGTCAT CAGCGGCAAT
       PMC21 GCAAAACAGC GGTTGGAATT TGGATTCCAA AGCGGTTGCA GGTTCTTCGG GCAAAGTCAT CAGCGGCAAT
       EG327 GCAAAACAGC GGTTGGAATT TGGATTCCAA AGCGGTTGCA GGTTCTTCGG GCAAAGTCAT CAGCGGCAAT
   Consensus GCAAAACAGC GGTTGGAATT TGGATTCCAA AGCGGTTGCA GGTTCTTCGG GCAAAGTCAT CAGCGGCAAT
                                                C5

1261                                                                    1330
       H15   GTTTCGCCGA GCAAGGGAAA GATGGATGAA ACCGTCAACA TTAATGCCGG CAACAACATC GAGATTACCC
       BZ10  GTTTCGCCGA GCAAGGGAAA GATGGATGAA ACCGTCAACA TTAATGCCGG CAACAACATC GAGATTACCC
       BZ198 GTTTCGCCGA GCAAGGGAAA GATGGATGAA ACCGTCAACA TTAATGCCGG CAACAACATC GAGATTACCC
       P20   GTTTCGCCGA GCAAGGGAAA GATGGATGAA ACCGTCAACA TTAATGCCGG CAACAACATC GAGATTACCC
       H38   GTTTCGCCGA GCAAGGGAAA GATGGATGAA ACCGTCAACA TTAATGCCGG CAACAACATC GAGATTACCC
       Z2491 GTTTCGCCGA GCAAGGGAAA GATGGATGAA ACCGTCAACA TTAATGCCGG CAACAACATC GAGATTAGCC
       H41   GTTTCGCCGA GCAAGGGAAA GATGGATGAA ACCGTCAACA TTAATGCCGG CAACAACATC GAGATTACCC
       EG329 GTTTCGCCGA GCAAGGGAAA GATGGATGAA ACCGTCAACA TTAATGCCGG CAACAACATC GAGATTACCC
       PMC21 GTTTCGCCGA GCAAGGGAAA GATGGATGAA ACCGTCAACA TTAATGCCGG CAACAACATC GAGATTACCC
       EG327 GTTTCGCCGA GCAAGGGAAA GATGGATGAA ACCGTCAACA TTAATGCCGG CAACAACATC GAGATTACCC
   Consensus GTTTCGCCGA GCAAGGGAAA GATGGATGAA ACCGTCAACA TTAATGCCGG CAACAACATC GAGATTA-CC
                                                C5

1331                                                                    1400
       H15   GCAACGGCAA AAATATCGAC ATCGCCACTT CGATGACCCC GCAATTTTCC AGCGTTTCGC TCGGCGCGGG
       BZ10  GCAACGGCAA AAATATCGAC ATCGCCACTT CGATGACCCC GCAATTTTCC AGCGTTTCGC TCGGCGCGGG
       BZ198 GCAACGGTAA AAATATCGAC ATCGCCACTT CGATGGCGCC GCAGTTTTCC AGCGTTTCGC TCGGTGCGGG
       P20   GCAACGGCAA AAATATCGAC ATCGCCACTT CGATGACCCC GCAATTTTCC AGCGTTTCGC TCGGCGCGGG
       H38   GCAACGGTAA AAATATCGAC ATCGCCACTT CGATGACCCC GCAGTTTTCC AGCGTTTCGC TCGGCGCGGG
       Z2491 GCAACGGTAA AAATATCGAC ATCGCCACTT CGATGGCGCC GCAGTTTTCC AGCGTTTCGC TCGGCGCGGG
       H41   GCAACGGCAA AAATATCGAC ATCGCCACTT CGATGACCCC GCAATTTTCC AGCGTTTCGC TCGGCGCGGG
       EG329 GCAACGGTAA AAATATCGAC ATCGCCACTT CGATGACCCC GCAGTTTTCC AGCGTTTCGC TCGGCGCGGG
       PMC21 GCAACGGTAA AAATATCGAC ATCGCCACTT CGATGACCCC GCAGTTTTCC AGCGTTTCGC TCGGCGCGGG
       EG327 GCAACGGCAA AAATATCGAC ATCGCCACTT CGATGACCCC GCAATTTTCC AGCGTTTCGC TCGGCGCGGG
   Consensus GCAACGG-AA AAATATCGAC ATCGCCACTT CGATG-C-CC GCA-TTTTCC AGCGTTTCGC TCGG-GCGGG
                                                C5

1401                                                                    1470
       H15   GGCGGATGCG CCCACTTTAA GCGTGGATGA CGAGGGCGCG TTGAATGTCG GCAGCAAGGA TGCCAACAAA
       BZ10  GGCGGATGCG CCCACTTTAA GCGTGGATGA CGAGGGCGCG TTGAATGTCG GCAGCAAGGA TGCCAACAAA
       BZ198 GGCGGATGCG CCCACTTTGA GCGTGGATGA CGAGGGCGCG TTGAATGTCG GCAGCAAGGA TACCAACAAA
       P20   GGCGGATGCG CCCACTTTAA GCGTGGATGA CGAGGGCGCG TTGAATGTCG GCAGCAAGGA TGCCAACAAA
       H38   GGCGGATGCG CCCACTTTGA GCGTGGATGA CGAGGGCGCG TTGAATGTCG GCAGCAAGGA TGCCAACAAA
       Z2491 GGCAGATGCG CCCACTTTAA GCGTGGATGA CAAGGGCGCG TTGAATGTCG GCAGCAAGGA TGCCAACAAA
       H41   GGCGGATGCG CCCACTTTAA GCGTGGATGA CGAGGGCGCG TTGAATGTCG GCAGCAAGGA TGCCAACAAA
       EG329 GGCGGATGCG CCCACTTTGA GCGTGGAT.. .GGGGACGCA TTGAATGTCG GCAGCAAGAA GGACAACAAA
       PMC21 GGCGGATGCG CCCACTTTGA GCGTGGAT.. .GGGGACGCA TTGAATGTCG GCAGCAAGAA GGACAACAAA
       EG327 GGCGGATGCG CCCACTTTAA GCGTGGATGA CGAGGGCGCG TTGAATGTCG GCAGCAAGGA TGCCAACAAA
   Consensus GGC-GATGCG CCCACTTT-A GCGTGGAT-- ---GG-CGC- TTGAATGTCG GCAGCAAG-A ---CAACAAA
                                                C5
```

FIG. 2F

```
              1471                                                                   1540
       H15 CCCGTCCGCA TTACCAATGT CGCCCCGGGC GTTAAAGAGG GGGATGTTAC AAACGTCGCA CAACTTAAAG
      BZ10 CCCGTCCGCA TTACCAATGT CGCCCCGGGC GTTAAAGAGG GGGATGTTAC AAACGTCGCA CAACTTAAAG
     BZ198 CCCGTCCGCA TTACCAATGT CGCCCCGGGC GTTAAAGAGG GGGATGTTAC AAACGTCGCA CAACTTAAAG
       P20 CCCGTCCGCA TTACCAATGT CGCCCCGGGC GTTAAAGAGG GGGATGTTAC AAACGTCGCA CAACTTAAAG
       H38 CCCGTCCGCA TTACCAATGT CGCCCCGGGC GTTAAAGAGG GGGATGTTAC AAACGTCGCA CAACTTAAAG
     Z2491 CCCGTCCGCA TTACCAATGT CGCCCCGGGC GTTAAAGAGG GGGATGTTAC AAACGTCGCA CAACTTAAAG
       H41 CCCGTCCGCA TTACCAATGT CGCCCCGGGC GTTAAAGAGG GGGATGTTAC AAACGTCGCG CAACTTAAAG
     EG329 CCCGTCCGCA TTACCAATGT CGCCCCGGGC GTTAAAGAGG GGGATGTTAC AAACGTCGCA CAACTTAAAG
     PMC21 CCCGTCCGCA TTACCAATGT CGCCCCGGGC GTTAAAGAGG GGGATGTTAC AAACGTCGCA CAACTTAAAG
     EG327 CCCGTCCGCA TTACCAATGT CGCCCCGGGC GTTAAAGAGG GGGATGTTAC AAACGTCGCA CAACTTAAAG
 Consensus CCCGTCCGCA TTACCAATGT CGCCCCGGGC GTTAAAGAGG GGGATGTTAC AAACGTCGC- CAACTTAAAG
                                              C5

1541                                                                   1610
       H15 GTGTGGCGCA AAACTTGAAC AACCGCATCG ACAATGTGGA CGGCAACGCG CGCGCGGGTA TCGCCCAAGC
      BZ10 GTGTGGCGCA AAACTTGAAC AACCGCATCG ACAATGTGGA CGGCAACGCG CGCGCGGGTA TCGCCCAAGC
     BZ198 GCGTGGCGCA AAACTTGAAC AACCGCATCG ACAATGTGGA CGGCAACGCG CGTGCGGGCA TCGCCCAAGC
       P20 GTGTGGCGCA AAACTTGAAC AACCGCATCG ACAATGTGAA CGGCAACGCG CGCGCGGGTA TCGCCCAAGC
       H38 GCGTGGCGCA AAACTTGAAC AACCGCATCG ACAATGTGGA CGGCAACGCG CGTGCGGGCA TCGCCCAAGC
     Z2491 GCGTGGCGCA AAACTTGAAC AACCGCATCG ACAATGTGGA CGGCAACGCG CGTGCGGGCA TCGCCCAAGC
       H41 GTGTGGCGCA AAACTTGAAC AACCGCATCG ACAATGTGAA CGGCAACGCG CGTGCGGGCA TCGCCCAAGC
     EG329 GCGTGGCGCA AAACTTGAAC AACCGCATCG ACAATGTGGA CGGCAACGCG CGTGCGGGCA TCGCCCAAGC
     PMC21 GCGTGGCGCA AAACTTGAAC AACCGCATCG ACAATGTGGA CGGCAACGCG CGTGCGGGCA TCGCCCAAGC
     EG327 GCGTGGCGCA AAACTTGAAC AACCACATCG ACAATGTGGA CGGCAACGCG CGTGCGGGCA TCGCCCAAGC
 Consensus G-GTGGCGCA AAACTTGAAC AACC-CATCG ACAATGTG-A CGGCAACGCG CG-GCGGG-A TCGCCCAAGC
                                              C5

1611                                                                   1680
       H15 GATTGCAACC GCAGGTTTGG CTCAGGCGTA TTTGCCCGGC AAGAGTATGA TGGCGATCGG CGGCGGTACT
      BZ10 GATTGCAACC GCAGGTTTGG CTCAGGCCTA TTTGCCCGGC AAGAGTATGA TGGCGATCGG CGGCGGTACT
     BZ198 GATTGCAACC GCAGGTCTAG TTCAGGCGTA TCTGCCCGGC AAGAGTATGA TGGCGATCGG CGGCGACACT
       P20 GATTGCAACC GCAGGTTTGG CTCAGGCCTA TTTGCCCGGC AAGAGTATGA TGGCGATCGG CGGCGGTACT
       H38 GATTGCAACC GCAGGTCTGG TTCAGGCGTA TCTGCCCGGC AAGAGTATGA TGGCGATCGG CGGCGGCACT
     Z2491 GATTGCAACC GCAGGTCTGG TTCAGGCGTA TCTGCCCGGC AAGAGTATGA TGGCGATCGG CGGCGGCACT
       H41 GATTGCAACC GCAGGTCTGG TTCAGGCGTA TCTGCCCGGC AAGAGTATGA TGGCGATCGG CGGCGGCACT
     EG329 GATTGCAACC GCAGGTCTGG TTCAGGCGTA TTTGCCCGGC AAGAGTATGA TGGCGATCGG CGGCGGCACT
     PMC21 GATTGCAACC GCAGGTCTGG TTCAGGCGTA TTTGCCCGGC AAGAGTATGA TGGCGATCGG CGGCGGCACT
     EG327 GATTGCAACC GCAGGTCTGG TTCAGGCGTA TCTGCCCGGC AAGAGTATGA TGGCGATCGG CGGCGGCACT
 Consensus GATTGCAACC GCAGGT-T-G -TCAGGC-TA T-TGCCCGGC AAGAGTATGA TGGCGATCGG CGGCG--ACT
                                              C5
```

FIG. 2G

```
           1681                                                                                 1750
H15        TATCGCGGGCG AAGCCGGTTA CGCCATCGGC TACTCGAGCA TTTCTGACAC TGGGAATTGG GTTATCAAGG
BZ10       TATCGCGGGCG AAGCCGGTTA CGCCATCGGC TACTCGAGCA TTTCTGACAC TGGGAATTGG GTTATCAAGG
BZ198      TATCGCGGGCG AAGCCGGTTA CGCCATCGGC TACTCAAGTA TTTCCGACGG CGGAAATTGG ATTATCAAAG
P20        TATCTCGGGCG AAGCCGGTTA CGCCATCGGC TACTCGAGCA TTTCTGACAC TGGGAATTGG GTTATCAAGG
H38        TATCGCGGGCG AAGCCGGTTA CGCCATCGGC TACTCCAGTA TTTCCGACGG CGGAAATTGG ATTATCAAAG
Z2491      TATCGCGGGCG AAGCCGGTTA CGCCATCGGC TACTCCAGTA TTTCCGACGG CGGAAATTGG ATTATCAAAG
H41        TATCTCGGGCG AAGCCGGTTA TGCCATCGGC TACTCCAGTA TTTCCGCCGG CGGAAATTGG ATTATCAAAG
EG329      TATCGCGGGCG AAGCCGGTTA CGCCATCGGC TACTCCAGTA TTTCCGACGG CGGAAATTGG ATTATCAAAG
PMC21      TATCGCGGGCG AAGCCGGTTA CGCCATCGGC TACTCAAGTA TTTCCGACGG CGGAAATTGG ATTATCAAAG
EG327      TATCGCGGGCG AAGCCGGTTA TGCCATCGGC TACTCAAGCA TTTCCGACGG CGGAAATTGG ATTATCAAAG
Consensus  TATC-CGGGCG AAGCCGGTTA -GCCATCGGC TACTC-AG-A TTTC-G-C-- -GG-AATTGG -TTATCAA-G
                                            C5

1751                                                                      1815
H15        GCACGGCTTC CGGCAATTCG CGCGGCCCATT TCGGTGCTTC CGCATCTGTC GGTTATCAGT GGTAA
BZ10       GCACGGCTTC CGGCAATTCG CGCGGCCCATT TCGGTGCTTC CGCATCTGTC GGTTATCAGT GGTAA
BZ198      GCACGGCTTC CGGCAATTCG CGCGGCCCATT TCGGTGCTTC CGCATCTGTC GGTTATCAAT GGTAA
P20        GCACGGCTTC CGGCAATTCG CGCGGCCCATT TCGGTACTTC CGCATCTGTC GGTTATCAGT GGTAA
H38        GCACGGCTTC CGGCAATTCG CGCGGCCCATT TCGGTGCTTC CGCATCTGTC GGTTATCAGT GGTAA
Z2491      GCACGGCTTC CGGCAATTCG CGCGGCCCATT TCGGTGCTTC CGCATCTGTC GGTTATCAGT GGTAA
H41        GCACGGCTTC CGGCAATTCG CGCGGCCCATT TCGGTGCTTC CGCATCTGTC GGTTATCAGT GGTAA
EG329      GCACGGCTTC CGGCAATTCG CGCGGCCCATT TCGGTGCTTC CGCATCTGTC GGTTATCAGT GGTAA
PMC21      GCACGGCTTC CGGCAATTCG CGCGGCCCATT TCGGTGCTTC CGCATCTGTC GGTTATCAGT GGTAA
EG327      GCACGGCTTC CGGCAATTCG CGCGG-CATT TCGGT-CTTC CGCATCTGTC GGTTATCAGT GGTAA
Consensus  GCACGGCTTC CGGCAATTCG CGCGG-CATT TCGGT-CTTC CGCATCTGTC GGTTATCA-T GGTAA-G
                                            C5
```

*FIG. 2H*

```
  1  MNKIYRIIWN  SALNAWVVVS  ELTRNHTKRA  SATVKTAVLA  TLLFATVQAS
 51  ANNETDLTSV  GTEKLSFSAN  GNKVNITSDT  KGLNFAKETA  GTNGDTTVHL
101  NGIGSTLTDT  LLNTGATTNV  TNDNVTDDEK  KRAASVKDVL  NAGWNIKGVK
151  PGTTASDNVD  FVRTYDTVEF  LSADTKTTTV  NVESKDNGKK  TEVKIGAKTS
201  VIKEKDGKLV  TGKDKGENGS  STDEGEGLVT  AKEVIDAVNK  AGWRMKTTTA
251  NGQTGQADKF  ETVTSGTNVT  FASGKGTTAT  VSKDDQGNIT  VMYDVNVGDA
301  LNVNQLQNSG  WNLDSKAVAG  SSGKVISGNV  SPSKGKMDET  VNINAGNNIE
351  ITRNGKNIDI  ATSMTPQFSS  VSLGAGADAP  TLSVDGDALN  VGSKKDNKPV
401  RITNVAPGVK  EGDVTNVAQL  KGVAQNLNNR  IDNVDGNARA  GIAQAIATAG
451  LVQAYLPGKS  MMAIGGGTYR  GEAGYAIGYS  SISDGGNWII  KGTASGNSRG
501  HFGASASVGY  QW*
```

FIG. 5A

```
   1  ATGAACAAAA  TATACCGCAT  CATTTGGAAT  AGTGCCCTCA  ATGCATGGGT
  51  CGTCGTATCC  GAGCTCACAC  GCAACCACAC  CAAACGCGCC  TCCGCAACCG
 101  TGAAGACCGC  CGTATTGGCG  ACTCTGTTGT  TTGCAACGGT  TCAGGCAAGT
 151  GCTAACAATG  AAACAGATCT  GACCAGTGTT  GGAACTGAAA  AATTATCGTT
 201  TAGCGCAAAC  GGCAATAAAG  TCAACATCAC  AAGCGACACC  AAAGGCTTGA
 251  ATTTTGCGAA  AGAAACGGCT  GGGACGAACG  GCGACACCAC  GGTTCATCTG
 301  AACGGTATTG  GTTCGACTTT  GACCGATACG  CTGCTGAATA  CCGGAGCGAC
 351  CACAAACGTA  ACCAACGACA  ACGTTACCGA  TGACGAGAAA  AAACGTGCGG
 401  CAAGCGTTAA  AGACGTATTA  AACGCTGGCT  GGAACATTAA  AGGCGTTAAA
 451  CCCGGTACAA  CAGCTTCCGA  TAACGTTGAT  TTCGTCCGCA  CTTACGACAC
 501  AGTCGAGTTC  TTGAGCGCAG  ATACGAAAAC  AACGACTGTT  AATGTGGAAA
 551  GCAAAGACAA  CGGCAAGAAA  ACCGAAGTTA  AAATCGGTGC  GAAGACTTCT
 601  GTTATTAAAG  AAAAAGACGG  TAAGTTGGTT  ACTGGTAAAG  ACAAAGGCGA
 651  GAATGGTTCT  TCTACAGACG  AAGGCGAAGG  CTTAGTGACT  GCAAAAGAAG
 701  TGATTGATGC  AGTAAACAAG  GCTGGTTGGA  GAATGAAAAC  AACAACCGCT
 751  AATGGTCAAA  CAGGTCAAGC  TGACAAGTTT  GAAACCGTTA  CATCAGGCAC
 801  AAATGTAACC  TTTGCTAGTG  GTAAAGGTAC  AACTGCGACT  GTAAGTAAAG
 851  ATGATCAAGG  CAACATCACT  GTTATGTATG  ATGTAAATGT  CGGCGATGCC
 901  CTAAACGTCA  ATCAGCTGCA  AAACAGCGGT  TGGAATTTGG  ATTCCAAAGC
 951  GGTTGCAGGT  TCTTCGGGCA  AAGTCATCAG  CGGCAATGTT  TCGCCGAGCA
1001  AGGGAAAGAT  GGATGAAACC  GTCAACATTA  ATGCCGGCAA  CAACATCGAG
1051  ATTACCCGCA  ACGGTAAAAA  TATCGACATC  GCCACTTCGA  TGACCCCGCA
1101  GTTTTCCAGC  GTTTCGCTCG  GCGCGGGGGC  GGATGCGCCC  ACTTTGAGCG
1151  TGGATGGGGA  CGCATTGAAT  GTCGGCAGCA  AGAAGGACAA  CAAACCCGTC
1201  CGCATTACCA  ATGTCGCCCC  GGGCGTTAAA  GAGGGGGATG  TTACAAACGT
1251  CGCACAACTT  AAAGGCGTGG  CGCAAAACTT  GAACAACCGC  ATCGACAATG
1301  TGGACGGCAA  CGCGCGTGCG  GGCATCGCCC  AAGCGATTGC  AACCGCAGGT
1351  CTGGTTCAGG  CGTATTTGCC  CGGCAAGAGT  ATGATGGCGA  TCGGCGGCGG
1401  CACTTATCGC  GGCGAAGCCG  GTTACGCCAT  CGGCTACTCC  AGTATTTCCG
1451  ACGGCGGAAA  TTGGATTATC  AAAGGCACGG  CTTCCGGCAA  TTCGCGCGGC
1501  CATTTCGGTG  CTTCCGCATC  TGTCGGTTAT  CAGTGGTAA
```

FIG. 5B

```
  1  MNKIYRIIWN SALNAWVAVS ELTRNHTKRA SATVKTAVLA TLLFATVQAN
 51  ATDETGLINV ETEKLSFGAN GKKVNIISDT KGLNFAKETA GTNGDTTVHL
101  NGIGSTLTDM LLNTGATTNV TNDNVTDDEK KRAASVKDVL NAGWNIKGVK
151  PGTTASDNVD FVRTYDTVEF LSADTKTTTV NVESKDNGKK TEVKIGAKTS
201  VIKEKDGKLV TGKGKGENGS STDEGEGLVT AKEVIDAVNK AGWRMKTTTA
251  NGQTGQADKF ETVTSGTKVT FASGNGTTAT VSKDDQGNIT VKYDVNVGDA
301  LNVNQLQNSG WNLDSKAVAG SSGKVISGNV SPSKGKMDET VNINAGNNIE
351  ITRNGKNIDI ATSMTPQFSS VSLGAGADAP TLSVDDEGAL NVGSKDANKP
401  VRITNVAPGV KEGDVTNVAQ LKGVAQNLNN RIDNVNGNAR AGIAQAIATA
451  GLVQAYLPGK SMMAIGGGTY LGEAGYAIGY SSISAGGNWI IKGTASGNSR
501  GHFGASASVG YQW*
```

FIG. 6A

```
   1  ATGAACAAAA TATACCGCAT CATTTGGAAT AGTGCCCTCA ATGCCTGGGT
  51  CGCCGTATCC GAGCTCACAC GCAACCACAC CAAACGCGCC TCCGCAACCG
 101  TGAAGACCGC CGTATTGGCG ACACTGTTGT TTGCAACGGT TCAGGCGAAT
 151  GCTACCGATG AAACAGGCCT GATCAATGTT GAAACTGAAA AATTATCGTT
 201  TGGCGCAAAC GGCAAGAAAG TCAACATCAT AAGCGACACC AAAGGCTTGA
 251  ATTTCGCGAA AGAAACGGCT GGGACGAACG GCGACACCAC GGTTCATCTG
 301  AACGGTATCG GTTCGACTTT GACCGATATG CTGCTGAATA CCGGAGCGAC
 351  CACAAACGTA ACCAACGACA ACGTTACCGA TGACGAGAAA AAACGTGCGG
 401  CAAGCGTTAA AGACGTATTA AACGCAGGCT GGAACATTAA AGGCGTTAAA
 451  CCCGGTACAA CAGCTTCCGA TAACGTTGAT TTCGTCCGCA CTTACGACAC
 501  AGTCGAGTTC TTGAGCGCAG ATACGAAAAC AACGACTGTT AATGTGGAAA
 551  GCAAAGACAA CGGCAAGAAA ACCGAAGTTA AAATCGGTGC GAAGACTTCT
 601  GTTATTAAAG AAAAAGACGG TAAGTTGGTT ACTGGTAAAG GCAAAGGCGA
 651  GAATGGTTCT TCTACAGACG AAGGCGAAGG CTTAGTGACT GCAAAAGAAG
 701  TGATTGATGC AGTAAACAAG GCTGGTTGGA GAATGAAAAC AACAACCGCT
 751  AATGGTCAAA CAGGTCAAGC TGACAAGTTT GAAACCGTTA CATCAGGCAC
 801  AAAAGTAACC TTTGCTAGTG GTAATGGTAC AACTGCGACT GTAAGTAAAG
 851  ATGATCAAGG CAACATCACT GTTAAGTATG ATGTAAATGT CGGCGATGCC
 901  CTAAACGTCA ATCAGCTGCA AAACAGCGGT TGGAATTTGG ATTCCAAAGC
 951  GGTTGCAGGT TCTTCGGGCA AAGTCATCAG CGGCAATGTT TCGCCGAGCA
1001  AGGGAAAGAT GGATGAAACC GTCAACATTA ATGCCGGCAA CAACATCGAG
1051  ATTACCCGCA ACGGCAAAAA TATCGACATC GCCACTTCGA TGACCCCGCA
1101  ATTTTCCAGC GTTTCGCTCG GCGCGGGGGC GGATGCGCCC ACTTTAAGCG
1151  TGGATGACGA GGGCGCGTTG AATGTCGGCA GCAAGGATGC CAACAAACCC
1201  GTCCGCATTA CCAATGTCGC CCCGGGCGTT AAAGAGGGGG ATGTTACAAA
1251  CGTCGCGCAA CTTAAGGTG TGGCGCAAAA CTTGAACAAC CGCATCGACA
1301  ATGTGAACGG CAACGCGCGT GCGGGCATCG CCCAAGCGAT TGCAACCGCA
1351  GGTCTGGTTC AGGCGTATCT GCCCGGCAAG AGTATGATGG CGATCGGCGG
1401  CGGCACTTAT CTCGGCGAAG CCGGTTATGC CATCGGCTAC TCAAGCATTT
1451  CCGCCGGCGG AAATTGGATT ATCAAAGGCA CGGCTTCCGG CAATTCGCGC
1501  GGCCATTTCG GTGCTTCCGC ATCTGTCGGT TATCAGTGGT AA
```

FIG. 6B

```
  1  MNKIYRIIWN  SALNAWVVVS  ELTRNHTKRA  SATVKTAVLA  TLLFATVQAS
 51  ANNVDFVRTY  DTVEFLSADT  KTTTVNVESK  DNGKKTEVKI  GAKTSVIKEK
101  DGKLVTGKDK  GENGSSTDEG  EGLVTAKEVI  DAVNKAGWRM  KTTTANGQTG
151  QADKFETVTS  GTNVTFASGK  GTTATVSKDD  QGNITVMYDV  NVGDALNVNQ
201  LQNSGWNLDS  KAVAGSSGKV  ISGNVSPSKG  KMDETVNINA  GNNIEITRNG
251  KNIDIATSMT  PQFSSVSLGA  GADAPTLSVD  GDALNVGSKK  DNKPVRITNV
301  APGVKEGDVT  NVAQLKGVAQ  NLNNRIDNVD  GNARAGIAQA  IATAGLVQAY
351  LPGKSMMAIG  GGTYRGEAGY  AIGYSSISDG  GNWIIKGTAS  GNSRGHFGAS
401  ASVGYQW*
```

FIG. 7A

```
   1  ATGAACAAAA  TATACCGCAT  CATTTGGAAT  AGTGCCCTCA  ATGCATGGGT
  51  CGTCGTATCC  GAGCTCACAC  GCAACCACAC  CAAACGCGCC  TCCGCAACCG
 101  TGAAGACCGC  CGTATTGGCG  ACTCTGTTGT  TTGCAACGGT  TCAGGCAAGT
 151  GCTAACAACG  TTGATTTCGT  CCGCACTTAC  GACACAGTCG  AGTTCTTGAG
 201  CGCAGATACG  AAAACAACGA  CTGTTAATGT  GGAAAGCAAA  GACAACGGCA
 251  AGAAAACCGA  AGTTAAAATC  GGTGCAAGA  CTTCTGTTAT  TAAAGAAAAA
 301  GACGGTAAGT  TGGTTACTGG  TAAAGACAAA  GGCGAGAATG  GTTCTTCTAC
 351  AGACGAAGGC  GAAGGCTTAG  TGACTGCAAA  AGAAGTGATT  GATGCAGTAA
 401  ACAAGGCTGG  TTGGAGAATG  AAAACAACAA  CCGCTAATGG  TCAAACAGGT
 451  CAAGCTGACA  AGTTTGAAAC  CGTTACATCA  GGCACAAATG  TAACCTTTGC
 501  TAGTGGTAAA  GGTACAACTG  CGACTGTAAG  TAAAGATGAT  CAAGGCAACA
 551  TCACTGTTAT  GTATGATGTA  AATGTCGGCG  ATGCCCTAAA  CGTCAATCAG
 601  CTGCAAAACA  GCGGTTGGAA  TTTGGATTCC  AAAGCGGTTG  CAGGTTCTTC
 651  GGGCAAAGTC  ATCAGCGGCA  ATGTTTCGCC  GAGCAAGGGA  AAGATGGATG
 701  AAACCGTCAA  CATTAATGCC  GGCAACAACA  TCGAGATTAC  CCGCAACGGT
 751  AAAAATATCG  ACATCGCCAC  TTCGATGACC  CCGCAGTTTT  CCAGCGTTTC
 801  GCTCGGCGCG  GGGGCGGATG  CGCCCACTTT  GAGCGTGGAT  GGGGACGCAT
 851  TGAATGTCGG  CAGCAAGAAG  GACAACAAAC  CGTCCGCAT  TACCAATGTC
 901  GCCCCGGGCG  TTAAGAGGG  GGATGTTACA  AACGTCGCAC  AACTTAAAGG
 951  CGTGGCGCAA  AACTTGAACA  ACCGCATCGA  CAATGTGGAC  GGCAACGCGC
1001  GTGCGGGCAT  CGCCCAAGCG  ATTGCAACCG  CAGGTCTGGT  TCAGGCGTAT
1051  TTGCCCGGCA  AGAGTATGAT  GGCGATCGGC  GGCGGCACTT  ATCGCGGCGA
1101  AGCCGGTTAC  GCCATCGGCT  ACTCCAGTAT  TTCCGACGGC  GGAAATTGGA
1151  TTATCAAAGG  CACGGCTTCC  GGCAATTCGC  GCGGCCATTT  CGGTGCTTCC
1201  GCATCTGTCG  GTTATCAGTG  GTAA
```

FIG. 7B

```
  1  MNKIYRIIWN  SALNAWVVVS  ELTRNHTKRA  SATVKTAVLA  TLLFATVQAS
 51  ANRAASVKDV  LNAGWNIKGV  KPGTTASDNV  DFVRTYDTVE  FLSADTKTTT
101  VNVESKDNGK  KTEVKIGAKT  SVIKEKDGKL  VTGKDKGENG  SSTDEGEGLV
151  TAKEVIDAVN  KAGWRMKTTT  ANGQTGQADK  FETVTSGTNV  TFASGKGTTA
201  TVSKDDQGNI  TVMYDVNVGD  ALNVNQLQNS  GWNLDSKAVA  GSSGKVISGN
251  VSPSKGKMDE  TVNINAGNNI  EITRNGKNID  IATSMTPQFS  SVSLGAGADA
301  PTLSVDGDAL  NVGSKKDNKP  VRITNVAPGV  KEGDVTNVAQ  LKGVAQNLNN
351  RIDNVDGNAR  AGIAQAIATA  GLVQAYLPGK  SMMAIGGGTY  RGEAGYAIGY
401  SSISDGGNWI  IKGTASGNSR  GHFGASASVG  YQW*
```

FIG. 8A

```
   1  ATGAACAAAA  TATACCGCAT  CATTTGGAAT  AGTGCCCTCA  ATGCATGGGT
  51  CGTCGTATCC  GAGCTCACAC  GCAACCACAC  CAAACGCGCC  TCCGCAACCG
 101  TGAAGACCGC  CGTATTGGCG  ACTCTGTTGT  TTGCAACGGT  TCAGGCAAGT
 151  GCTAACCGTG  CGGCAAGCGT  TAAAGACGTA  TTAAACGCTG  GCTGGAACAT
 201  TAAAGGCGTT  AAACCCGGTA  CAACAGCTTC  CGATAACGTT  GATTTCGTCC
 251  GCACTTACGA  CACAGTCGAG  TTCTTGAGCG  CAGATACGAA  AACAACGACT
 301  GTTAATGTGG  AAAGCAAAGA  CAACGGCAAG  AAAACCGAAG  TTAAAATCGG
 351  TGCGAAGACT  TCTGTTATTA  AGAAAAAGA   CGGTAAGTTG  GTTACTGGTA
 401  AAGACAAAGG  CGAGAATGGT  TCTTCTACAG  ACGAAGGCGA  AGGCTTAGTG
 451  ACTGCAAAAG  AAGTGATTGA  TGCAGTAAAC  AAGGCTGGTT  GGAGAATGAA
 501  AACAACAACC  GCTAATGGTC  AAACAGGTCA  AGCTGACAAG  TTTGAAACCG
 551  TTACATCAGG  CACAAATGTA  ACCTTTGCTA  GTGGTAAAGG  TACAACTGCG
 601  ACTGTAAGTA  AAGATGATCA  AGGCAACATC  ACTGTTATGT  ATGATGTAAA
 651  TGTCGGCGAT  GCCCTAAACG  TCAATCAGCT  GCAAAACAGC  GGTTGGAATT
 701  TGGATTCCAA  AGCGGTTGCA  GGTTCTTCGG  GCAAAGTCAT  CAGCGGCAAT
 751  GTTTCGCCGA  GCAAGGGAAA  GATGGATGAA  ACCGTCAACA  TTAATGCCGG
 801  CAACAACATC  GAGATTACCC  GCAACGGTAA  AAATATCGAC  ATCGCCACTT
 851  CGATGACCCC  GCAGTTTTCC  AGCGTTTCGC  TCGGCGCGGG  GGCGGATGCG
 901  CCCACTTTGA  GCGTGGATGG  GGACGCATTG  AATGTCGGCA  GCAAGAAGGA
 951  CAACAAACCC  GTCCGCATTA  CCAATGTCGC  CCCGGGCGTT  AAAGAGGGGG
1001  ATGTTACAAA  CGTCGCACAA  CTTAAAGGCG  TGGCGCAAAA  CTTGAACAAC
1051  CGCATCGACA  ATGTGGACGG  CAACGCGCGT  GCGGGCATCG  CCCAAGCGAT
1101  TGCAACCGCA  GGTCTGGTTC  AGGCGTATTT  GCCCGGCAAG  AGTATGATGG
1151  CGATCGGCGG  CGGCACTTAT  CGCGGCGAAG  CCGGTTACGC  CATCGGCTAC
1201  TCCAGTATTT  CCGACGGCGG  AAATTGGATT  ATCAAAGGCA  CGGCTTCCGG
1251  CAATTCGCGC  GGCCATTTCG  GTGCTTCCGC  ATCTGTCGGT  TATCAGTGGT
1301  AA
```

FIG. 8B

```
  1  MNKIYRIIWN SALNAWVVVS ELTRNHTKRA SATVKTAVLA TLLFATVQAS
 51  ANTLKAGDNL KIKQFTYSLK KDLTDLTSVG TEKLSFSANG NKVNITSDTK
101  GLNFAKETAG TNGDTTVHLN GIGSTLTDRA ASVKDVLNAG WNIKGVKNVD
151  FVRTYDTVEF LSADTKTTTV NVESKDNGKK TEVKIGAKTS VIKEKDGKLV
201  TGKDKGENGS STDEGEGLVT AKEVIDAVNK AGWRMKTTTA NGQTGQADKF
251  ETVTSGTNVT FASGKGTTAT VSKDDQGNIT VMYDVNVGDA LNVNQLQNSG
301  WNLDSKAVAG SSGKVISGNV SPSKGKMDET VNINAGNNIE ITRNGKNIDI
351  ATSMTPQFSS VSLGAGADAP TLSVDGDALN VGSKKDNKPV RITNVAPGVK
401  EGDVTNVAQL KGVAQNLNNR IDNVDGNARA GIAQAIATAG LVQAYLPGKS
451  MMAIGGGTYR GEAGYAIGYS SISDGGNWII KGTASGNSRG HFGASASVGY
501  QW*
```

FIG. 9A

```
   1 ATGAACAAAA TATACCGCAT CATTTGGAAT AGTGCCCTCA ATGCATGGGT
  51 CGTCGTATCC GAGCTCACAC GCAACCACAC CAAACGCGCC TCCGCAACCG
 101 TGAAGACCGC CGTATTGGCG ACTCTGTTGT TTGCAACGGT TCAGGCAAGT
 151 GCTAACACCC TCAAAGCCGG CGACAACCTG AAAATCAAAC AATTCACCTA
 201 CTCGCTGAAA AAAGACCTCA CAGATCTGAC CAGTGTTGGA ACTGAAAAAT
 251 TATCGTTTAG CGCAAACGGC AATAAAGTCA ACATCACAAG CGACACCAAA
 301 GGCTTGAATT TTGCGAAAGA AACGGCTGGG ACGAACGGCG ACACCACGGT
 351 TCATCTGAAC GGTATTGGTT CGACTTTGAC CGATCGTGCG GCAAGCGTTA
 401 AAGACGTATT AAACGCTGGC TGGAACATTA AAGGCGTTAA AAACGTTGAT
 451 TTCGTCCGCA CTTACGACAC AGTCGAGTTC TTGAGCGCAG ATACGAAAAC
 501 AACGACTGTT AATGTGGAAA GCAAAGACAA CGGCAAGAAA ACCGAAGTTA
 551 AAATCGGTGC GAAGACTTCT GTTATTAAAG AAAAAGACGG TAAGTTGGTT
 601 ACTGGTAAAG ACAAAGGCGA AAATGGTTCT TCTACAGACG AAGGCGAAGG
 651 CTTAGTGACT GCAAAAGAAG TGATTGATGC AGTAAACAAG GCTGGTTGGA
 701 GAATGAAAAC AACAACCGCT AATGGTCAAA CAGGTCAAGC TGACAAGTTT
 751 GAAACCGTTA CATCAGGCAC AAATGTAACC TTTGCTAGTG GTAAAGGTAC
 801 AACTGCGACT GTAAGTAAAG ATGATCAAGG CAACATCACT GTTATGTATG
 851 ATGTAAATGT CGGCGATGCC CTAAACGTCA ATCAGCTGCA AAACAGCGGT
 901 TGGAATTTGG ATTCCAAAGC GGTTGCAGGT TCTTCGGGCA AAGTCATCAG
 951 CGGCAATGTT TCGCCGAGCA AGGGAAAGAT GGATGAAACC GTCAACATTA
1001 ATGCCGGCAA CAACATCGAG ATTACCCGCA ACGGTAAAAA TATCGACATC
1051 GCCACTTCGA TGACCCCGCA GTTTTCCAGC GTTTCGCTCG GCGCGGGGGC
1101 GGATGCGCCC ACTTTGAGCG TGGATGGGGA CGCATTGAAT GTCGGCAGCA
1151 AGAAGGACAA CAAACCCGTC CGCATTACCA ATGTCGCCCC GGGCGTTAAA
1201 GAGGGGGATG TTACAAACGT CGCACAACTT AAAGGCGTGG CGCAAAACTT
1251 GAACAACCGC ATCGACAATG TGGACGGCAA CGCGCGTGCG GGCATCGCCC
1301 AAGCGATTGC AACCGCAGGT CTGGTTCAGG CGTATTTGCC CGGCAAGAGT
1351 ATGATGGCGA TCGGCGGCGG CACTTATCGC GGCGAAGCCG GTTACGCCAT
1401 CGGCTACTCC AGTATTTCCG ACGGCGGAAA TTGGATTATC AAAGGCACGG
1451 CTTCCGGCAA TTCGCGCGGC CATTTCGGTG CTTCCGCATC TGTCGGTTAT
1501 CAGTGGTAA
```

FIG. 9B

```
                1                                                                     50
H41             MNKIYRIIWN SALNAWVAVS ELTRNHTKRA SATVKTAVLA TLLFATVQAN
PMC21           MNKIYRIIWN SALNAWVVVS DLTRNHTKRA SATVNTAVLA TLLFATVQAS
H41Studel       MNKIYRIIWN SALNAWVAVS ELTRNHTKRA SATVKTAVLA TLLFATVQAN
PMC21Bgldel     MNKIYRIIWN SALNAWVVVS ELTRNHTKRA SATVKTAVLA TLLFATVQAS
PMC21C1C5       MNKIYRIIWN SALNAWVVVS ELTRNHTKRA SATVKTAVLA TLLFATVQAS
                                              C1

51                                                                    100
H41             ATDED..EEE ELESVQRS.V VGSIQASMEG SVELET...I SLSMTNDSKE
PMC21           ANNEEQEEYL YLHPVQRTVA VLIVNSDKEG AGEKEKVEEN SDWAVYFNEK
H41Studel       ATDE...... .......... .......... .......... ..........
PMC21Bgldel     ANNE...... .......... .......... .......... ..........
PMC21C1C5       AN........ .......... .......... .......... ..........
                                               V1

101                                                                   150
H41             FVDPYIVVTL KAGDNLKIKQ N.TNENTNAS SFTYSLKKDL TGLINVETEK
PMC21           GVLTAREITL KAGDNLKIKQ NGTN...... .FTYSLKKDL TDLTSVGTEK
H41Studel       .......... .......... .......... .......... TGLINVETEK
PMC21Bgldel     .......... .......... .......... .......... TDLTSVGTEK
PMC21C1C5       .......... .......... .......... .......... ..........
                    V1            C2            V2            C3

151                                                                   200
H41             LSFGANGKKV NIISDTKGLN FAKETAGTNG DTTVHLNGIG STLTDMLLNT
PMC21           LSFSAHGNKV NITSDTKGLN FAKETAGTNG DTTVHLNGIG STLTDTLLNT
H41Studel       LSFGANGKKV NIISDTKGLN FAKETAGTNG DTTVHLNGIG STLTDMLLNT
PMC21Bgldel     LSFSANGNKV NITSDTKGLN FAKETAGTNG DTTVHLNGIG STLTDTLLNT
PMC21C1C5       .......... .......... .......... .......... ..........
                             C3                                          V3

201                                                                   250
H41             GATTNVTNDN VTDDEKKRAA SVKDVLNAGW NIKGVKPGTT ASDNVDFVRT
PMC21           GATTNVTNDN VTDDEKKRAA SVKDVLNAGW NIKGVKPGTT ASDNVDFVRT
H41Studel       GATTNVTNDN VTDDEKKRAA SVKDVLNAGW NIKGVKPGTT ASDNVDFVRT
PMC21Bgldel     GATTNVTNDN VTDDEKKRAA SVKDVLNAGW NIKGVKPGTT ASDNVDFVRT
PMC21C1C5       .......... .......... .......... .......... ...NVDFVRT
                    V3            C4            V4      C5

251                                                                   300
H41             YDTVEFLSAD TKTTTVNVES KDNGKKTEVK IGAKTSVIKE KDGKLVTGKG
PMC21           YDTVEFLSAD TKTTTVNVES KDNGKKTEVK IGAKTSVIKE KDGKLVTGKD
H41Studel       YDTVEFLSAD TKTTTVNVES KDNGKKTEVK IGAKTSVIKE KDGKLVTGKG
PMC21Bgldel     YDTVEFLSAD TKTTTVNVES KDNGKKTEVK IGAKTSVIKE KDGKLVTGKD
PMC21C1C5       YDTVEFLSAD TKTTTVNVES KDNGKKTEVK IGAKTSVIKE KDGKLVTGKD
                                               C5

301                                                                   350
H41             KGENGSSTDE GEGLVTAKEV IDAVNKAGWR MKTTTANGQT GQADKFETVT
PMC21           KGENGSSTDE GEGLVTAKEV IDAVNKAGWR MKTTTANGQT GQADKFETVT
H41Studel       KGENGSSTDE GEGLVTAKEV IDAVNKAGWR MKTTTANGQT GQADKFETVT
PMC21Bgldel     KGENGSSTDE GEGLVTAKEV IDAVNKAGWR MKTTTANGQT GQADKFETVT
PMC21C1C5       KGENGSSTDE GEGLVTAKEV IDAVNKAGWR MKTTTANGQT GQADKFETVT
                                               C5

351                                                                   400
H41             SGTKVTFASG NGTTATVSKD DQGNITVKYD VNVGDALNVN QLQNSGWNLD
PMC21           SGTNVTFASG KGTTATVSKD DQGNITVMYD VNVGDALNVN QLQNSGWNLD
H41Studel       SGTKVTFASG NGTTATVSKD DQGNITVKYD VNVGDALNVN QLQNSGWNLD
PMC21Bgldel     SGTNVTFASG KGTTATVSKD DQGNITVMYD VNVGDALNVN QLQNSGWNLD
PMC21C1C5       SGTNVTFASG KGTTATVSKD DQGNITVMYD VNVGDALNVN QLQNSGWNLD
                                               C5
```

FIG. 10A

```
              401                                                   450
       H41   SKAVAGSSGK VISGNVSPSK GKMDETVNIN AGNNIEITRN GKNIDIATSM
     PMC21   SKAVAGSSGK VISGNVSPSK GKMDETVNIN AGNNIEITRN GKNIDIATSM
  H41Studel  SKAVAGSSGK VISGNVSPSK GKMDETVNIN AGNNIEITRN GKNIDIATSM
 PMC21Bgldel SKAVAGSSGK VISGNVSPSK GKMDETVNIN AGNNIEITRN GKNIDIATSM
   PMC21C1C5 SKAVAGSSGK VISGNVSPSK GKMDETVNIN AGNNIEITRN GKNIDIATSM
                                                   C5

451                                                   500
       H41   TPQFSSVSLG AGADAPTLSV DDEGALNVGS KDANKPVRIT NVAPGVKEGD
     PMC21   TPQFSSVSLG AGADAPTLSV DG.DALNVGS KKDNKPVRIT NVAPGVKEGD
  H41Studel  TPQFSSVSLG AGADAPTLSV DDEGALNVGS KDANKPVRIT NVAPGVKEGD
 PMC21Bgldel TPQFSSVSLG AGADAPTLSV DG.DALNVGS KKDNKPVRIT NVAPGVKEGD
   PMC21C1C5 TPQFSSVSLG AGADAPTLSV DG.DALNVGS KKDNKPVRIT NVAPGVKEGD
                                                   C5

501                                                   550
       H41   VTNVAQLKGV AQNLNNRIDN VNGNARAGIA QAIATAGLVQ AYLPGKSMMA
     PMC21   VTNVAQLKGV AQNLNNRIDN VDGNARAGIA QAIATAGLVQ AYLPGKSMMA
  H41Studel  VTNVAQLKGV AQNLNNRIDN VNGNARAGIA QAIATAGLVQ AYLPGKSMMA
 PMC21Bgldel VTNVAQLKGV AQNLNNRIDN VDGNARAGIA QAIATAGLVQ AYLPGKSMMA
   PMC21C1C5 VTNVAQLKGV AQNLNNRIDN VDGNARAGIA QAIATAGLVQ AYLPGKSMMA
                                                   C5

551                                                   600
       H41   IGGGTYLGEA GYAIGYSSIS AGGNWIIKGT ASGNSRGHFG ASASVGYQW.
     PMC21   IGGGTYRGEA GYAIGYSSIS DGGNWIIKGT ASGNSRGHFG ASASVGYQW.
  H41Studel  IGGGTYLGEA GYAIGYSSIS AGGNWIIKGT ASGNSRGHFG ASASVGYQW.
 PMC21Bgldel IGGGTYRGEA GYAIGYSSIS DGGNWIIKGT ASGNSRGHFG ASASVGYQW.
   PMC21C1C5 IGGGTYRGEA GYAIGYSSIS DGGNWIIKGT ASGNSRGHFG ASASVGYQW.
                                                   C5
```

```
 52    NNEEQEEYL  YLHPVQRTVA  VLIVNSDKEG  AGEKEKVEEN  SDWAVYFNEK
101    GVLTAREITL  KAGDNLKIKQ  NGTNFTYSLK  KDLTDLTSVG  TEKLSFSAHG
151    NKVNITSDTK  GLNFAKETAG  TNGDTTVHLN  GIGSTLTDTL  LNTGATTNVT
201    NDNVTDDEKK  RAASVKDVLN  AGWNIKGVKP  GTTASDNVDF  VRTYDTVEFL
251    SADTKTTTVN  VESKDNGKKT  EVKIGAKTSV  IKEKDGKLVT  GKDKGENGSS
301    TDEGEGLVTA  KEVIDAVNKA  GWRMKTTTAN  GQTGQADKFE  TVTSGTNVTF
351    ASGKGTTATV  SKDDQGNITV  MYDVNVGDAL  NVNQLQNSGW  NLDSKAVAGS
401    SGKVISGNVS  PSKGKMDETV  NINAGNNIEI  TRNGKNIDIA  TSMTPQFSSV
451    SLGAGADAPT  LSVDGDALNV  GSKKDNKPVR  ITNVAPGVKE  GDVTNVAQLK
501    GVAQNLNNRI  DNVDGNARAG  IAQAIATAGL  VQAYLPGKSM  MAIGGGTYRG
551    EAGYAIGYSS  ISDGGNWIIK  GTASGNSRGH  FGASASVGYQ  W*
```

FIG. 14A

```
 52    TDEDEEEEL  ESVQRSVVGS  IQASMEGSVE  LETISLSMTN  DSKEFVDPYI
101    VVTLKAGDNL  KIKQNTNENT  NASSFTYSLK  KDLTGLINVE  TEKLSFGANG
151    KKVNIISDTK  GLNFAKETAG  TNGDTTVHLN  GIGSTLTDML  LNTGATTNVT
201    NDNVTDDEKK  RAASVKDVLN  AGWNIKGVKP  GTTASDNVDF  VRTYDTVEFL
251    SADTKTTTVN  VESKDNGKKT  EVKIGAKTSV  IKEKDGKLVT  GKGKGENGSS
301    TDEGEGLVTA  KEVIDAVNKA  GWRMKTTTAN  GQTGQADKFE  TVTSGTKVTF
351    ASGNGTTATV  SKDDQGNITV  KYDVNVGDAL  NVNQLQNSGW  NLDSKAVAGS
401    SGKVISGNVS  PSKGKMDETV  NINAGNNIEI  TRNGKNIDIA  TSMTPQFSSV
451    SLGAGADAPT  LSVDDEGALN  VGSKDANKPV  RITNVAPGVK  EGDVTNVAQL
501    KGVAQNLNNR  IDNVNGNARA  GIAQAIATAG  LVQAYLPGKS  MMAIGGGTYL
551    GEAGYAIGYS  SISAGGNWII  KGTASGNSRG  HFGASASVGY  QW*
```

FIG. 14B

| 52 | NNETDLTSV | GTEKLSFSAN | GNKVNITSDT | KGLNFAKETA | GTNGDTTVHL |
| 101 | NGIGSTLTDT | LLNTGATTNV | TNDNVTDDEK | KRAASVKDVL | NAGWNIKGVK |
| 151 | PGTTASDNVD | FVRTYDTVEF | LSADTKTTTV | NVESKDNGKK | TEVKIGAKTS |
| 201 | VIKEKDGKLV | TGKDKGENGS | STDEGEGLVT | AKEVIDAVNK | AGWRMKTTTA |
| 251 | NGQTGQADKF | ETVTSGTNVT | FASGKGTTAT | VSKDDQGNIT | VMYDVNVGDA |
| 301 | LNVNQLQNSG | WNLDSKAVAG | SSGKVISGNV | SPSKGKMDET | VNINAGNNIE |
| 351 | ITRNGKNIDI | ATSMTPQFSS | VSLGAGADAP | TLSVDGDALN | VGSKKDNKPV |
| 401 | RITNVAPGVK | EGDVTNVAQL | KGVAQNLNNR | IDNVDGNARA | GIAQAIATAG |
| 451 | LVQAYLPGKS | MMAIGGGTYR | GEAGYAIGYS | SISDGGNWII | KGTASGNSRG |
| 501 | HFGASASVGY | QW* |

FIG. 14C

| 52 | TDETGLINV | ETEKLSFGAN | GKKVNIISDT | KGLNFAKETA | GTNGDTTVHL |
| 101 | NGIGSTLTDM | LLNTGATTNV | TNDNVTDDEK | KRAASVKDVL | NAGWNIKGVK |
| 151 | PGTTASDNVD | FVRTYDTVEF | LSADTKTTTV | NVESKDNGKK | TEVKIGAKTS |
| 201 | VIKEKDGKLV | TGKGKGENGS | STDEGEGLVT | AKEVIDAVNK | AGWRMKTTTA |
| 251 | NGQTGQADKF | ETVTSGTKVT | FASGNGTTAT | VSKDDQGNIT | VKYDVNVGDA |
| 301 | LNVNQLQNSG | WNLDSKAVAG | SSGKVISGNV | SPSKGKMDET | VNINAGNNIE |
| 351 | ITRNGKNIDI | ATSMTPQFSS | VSLGAGADAP | TLSVDDEGAL | NVGSKDANKP |
| 401 | VRITNVAPGV | KEGDVTNVAQ | LKGVAQNLNN | RIDNVNGNAR | AGIAQAIATA |
| 451 | GLVQAYLPGK | SMMAIGGGTY | LGEAGYAIGY | SSISAGGNWI | IKGTASGNSR |
| 501 | GHFGASASVG | YQW* |

FIG. 14D

```
 52    NNVDFVRTY  DTVEFLSADT  KTTTVNVESK  DNGKKTEVKI  GAKTSVIKEK
101    DGKLVTGKDK  GENGSSTDEG  EGLVTAKEVI  DAVNKAGWRM  KTTTANGQTG
151    QADKFETVTS  GTNVTFASGK  GTTATVSKDD  QGNITVMYDV  NVGDALNVNQ
201    LQNSGWNLDS  KAVAGSSGKV  ISGNVSPSKG  KMDETVNINA  GNNIEITRNG
251    KNIDIATSMT  PQFSSVSLGA  GADAPTLSVD  GDALNVGSKK  DNKPVRITNV
301    APGVKEGDVT  NVAQLKGVAQ  NLNNRIDNVD  GNARAGIAQA  IATAGLVQAY
351    LPGKSMMAIG  GGTYRGEAGY  AIGYSSISDG  GNWIIKGTAS  GNSRGHFGAS
401    ASVGYQW*
```

FIG. 14E

```
 52    NRAASVKDV  LNAGWNIKGV  KPGTTASDNV  DFVRTYDTVE  FLSADTKTTT
101    VNVESKDNGK  KTEVKIGAKT  SVIKEKDGKL  VTGKDKGENG  SSTDEGEGLV
151    TAKEVIDAVN  KAGWRMKTTT  ANGQTGQADK  FETVTSGTNV  TFASGKGTTA
201    TVSKDDQGNI  TVMYDVNVGD  ALNVNQLQNS  GWNLDSKAVA  GSSGKVISGN
251    VSPSKGKMDE  TVNINAGNNI  EITRNGKNID  IATSMTPQFS  SVSLGAGADA
301    PTLSVDGDAL  NVGSKKDNKP  VRITNVAPGV  KEGDVTNVAQ  LKGVAQNLNN
351    RIDNVDGNAR  AGIAQAIATA  GLVQAYLPGK  SMMAIGGGTY  RGEAGYAIGY
401    SSISDGGNWI  IKGTASGNSR  GHFGASASVG  YQW*
```

FIG. 14F

```
 50 SANTLKAGDNL  KIKQFTYSLK  KDLTDLTSVG  TEKLSFSANG  NKVNITSDTK
101    GLNFAKETAG  TNGDTTVHLN  GIGSTLTDRA  ASVKDVLNAG  WNIKGVKNVD
151    FVRTYDTVEF  LSADTKTTTV  NVESKDNGKK  TEVKIGAKTS  VIKEKDGKLV
201    TGKDKGENGS  STDEGEGLVT  AKEVIDAVNK  AGWRMKTTTA  NGQTGQADKF

251    ETVTSGTNVT  FASGKGTTAT  VSKDDQGNIT  VMYDVNVGDA  LNVNQLQNSG
301    WNLDSKAVAG  SSGKVISGNV  SPSKGKMDET  VNINAGNNIE  ITRNGKNIDI
351    ATSMTPQFSS  VSLGAGADAP  TLSVDGDALN  VGSKKDNKPV  RITNVAPGVK
401    EGDVTNVAQL  KGVAQNLNNR  IDNVDGNARA  GIAQAIATAG  LVQAYLPGKS
451    MMAIGGGTYR  GEAGYAIGYS  SISDGGNWII  KGTASGNSRG  HFGASASVGY
501    QW*
```

FIG. 14G

MODIFIED SURFACE ANTIGEN

CROSS-REFERENCE TO RELATED APPLICATIONS

This application is a continuation of and claims the priority of copending U.S. patent application Ser. No. 09/771,382, filed Jan. 25, 2001, which in turn was a non-provisional application based on and entitled to priority, pursuant to 35 U.S.C. §119(e), of U.S. Provisional Application Ser. No. 60/177,917, filed Jan. 25, 2000, which priority is hereby claimed. The disclosure of these related applications are hereby incorporated herein by reference in their entireties.

FIELD OF THE INVENTION

This invention relates to novel proteins that constitute modified forms of a *Neisseria meningitidis* surface antigen, to nucleic acids encoding such novel peptides and polypeptides, and to the use of these in diagnostics, in therapeutic and prophylactic vaccines and in the design and/or screening of medicaments. More particularly, by having deletions of non-conserved amino acids, the modified surface antigens of the invention may be useful in vaccines which effectively immunize against a broader spectrum of *N. meningitidis* strains than would be expected from a corresponding wild-type surface antigen.

BACKGROUND OF THE INVENTION

*Neisseria meningitidis* is a Gram-negative bacterium and the causative agent of meningococcal meningitis and septicemia. Its only known host is the human, and it may be carried asymptomatically by approximately 10% of the population (Caugant et al, 1994, Journal of Clinical Microbiology 32 323).

*N. meningitidis* may express a polysaccharide capsule, and this allows classification of the bacteria according to the nature of the capsule expressed. There are at least twelve serogroups of *N. meningitidis*: A, B, C, 29-E, H, I, K, L, W135, X, Y and Z, of which serogroups A, B, and C cause 90% of meningococcal disease (Poolman et al, 1995, Infectious Agents and Disease 4 13). Vaccines directed against serogroups A and C are available, but the serogroup B capsular polysaccharide is poorly immunogenic and does not induce protection in humans. Other membrane and extracellular components are therefore being examined for their suitability for inclusion in vaccines. Examples include the outer membrane proteins of classes 1, 2 and 3 (porin; encoded by por genes), and classes 4 (Rmp) and 5 (Opacity proteins; encoded by opa and opc genes). However, to date, none of these candidates is able to induce complete protection, particularly in children (Romero et al., 1994, Clinical Microbiology Review, 7 559; Poolman et al., 1995, supra).

To create an effective vaccine, it is necessary to identify components of *N. meningitidis* which are present in a majority of strains, and which are capable of inducing a protective immune response (for example, bactericidal antibodies).

In this regard, reference is made to International Publications WO 99/24578, WO99/36544, WO99/58683 and WO99/57280, each of which is incorporated herein by reference and describe a number of candidate proteins that may be useful in vaccines to immunize against *Neisseria meningitidis*.

In this regard, particular reference is made to International Publication WO99/31132 and Peak et al. 2000, FEMS Immunol. Med. Microbiol. 28 329, each of which is incorporated herein by reference and describe a novel surface antigen isolated from a number of different strains of *N. meningitidis*, which surface antigen, and allelic variants thereof, for the purposes of this specification will be referred to as NhhA.

SUMMARY OF THE INVENTION

The present inventors have discovered that the NhhA surface antigen has polypeptide regions which are variable between *N. meningitidis* strains, and other regions which are conserved between strains. The variable regions may be immunogenic and tend to elicit strain-specific immune responses, such that vaccines incorporating an NhhA antigen derived from a particular strain of *N. meningitidis* tend to preferentially immunize against that particular strain. As a result, the present inventors have sought to produce a modified NhhA polypeptide which elicits an immune response which is not as strain-specific as that elicited by wild-type NhhA. This modified NhhA antigen will be useful for the production of therapeutic and/or prophylactic vaccines against *N. meningitidis* as will be described hereinafter. By directing the immune response primarily against conserved epitopes, such vaccines should effectively immunize against a broader spectrum of *N. meningitidis* strains than would be expected following immunization with wild-type NhhA.

The present invention is therefore broadly directed to isolated proteins having conserved amino acids of NhhA polypeptides.

Proteins of the invention may therefore have one or more deletions of non-conserved amino acids compared to a corresponding wild-type NhhA polypeptide.

In a first aspect, the invention provides an isolated protein comprising twelve or more contiguous conserved amino acids sequences of an NhhA polypeptide, said isolated protein excluding wild-type NhhA polypeptides.

Suitably, the protein of the invention is capable of eliciting an immune response.

Preferably, the immune response is less strain-specific than that elicited by said corresponding wild-type NhhA polypeptide.

More preferably, said immune response provides protection against one or more strains of *N. meningitidis*, or even more preferably a plurality of strains of *N. meningitidis*.

Wild-type NhhA polypeptide sequences are exemplified in FIG. 1 (SEQ ID NOS:1 to 10).

A consensus amino acid sequence is also set forth in FIG. 1 (SEQ ID NO:1).

The isolated protein of the invention preferably comprises one or more constant regions of an NhhA polypeptide, herein designated C1, C2, C3, C4 and C5 regions in FIG. 1.

It will be appreciated that according to this aspect, suitably one or more non-conserved amino acids of a variable region of an NhhA polypeptide, designated as V1, V2, V3 or V4 regions in FIG. 1, are deleted with respect to a wild-type NhhA polypeptide.

Preferably, a V1 region, or at least a substantial portion thereof, is deleted.

In particular embodiments, the isolated protein has an amino acid sequence as set forth in any one of FIGS. 5 to 9 (SEQ ID NOS:23 to 27) which are examples of "modified NhhA polypeptides of the invention". In FIGS. 14A-14G (SEQ ID NOS:33 to 39) further examples are provided of "mature" polypeptides predicted to result of removal of N-terminal signal sequences.

According to a second aspect, the invention provides an isolated nucleic acid encoding a polypeptide according to the first aspect.

Wild-type nhhA nucleic acid sequences are exemplified in FIG. 2 (SEQ ID NOS:12 to 21).

A consensus nucleic acid sequence is also set forth in FIG. 2 (SEQ ID NO:22).

Preferably, the C1, C2, C3, C4 and C5 regions are encoded by respective nucleotide sequences as set forth in FIG. 2.

Preferably, the V1, V2, V3 and V4 regions are encoded by respective nucleotide sequences as set forth in FIG. 2.

In a particular embodiment, the isolated nucleic acid of the invention has a nucleotide sequence as set forth in any one of FIGS. 5 to 9 (SEQ ID NOS:28 to 32), which are particular examples of "modified nhhA nucleic acids of the invention".

The invention according to the first and second aspects extends to homologs, fragments, variants and derivatives of the isolated proteins and nucleic acids of the invention.

Specifically excluded from the scope of the invention are wild-type NhhA polypeptides and nhhA nucleic acids.

In a third aspect, the invention resides in an expression construct comprising an expression vector and a nucleic acid according to the second aspect, wherein said sequence is operably linked to one or more regulatory nucleic acids in said expression vector.

In a fourth aspect, the invention provides a host cell containing an expression construct according to the third aspect.

In a fifth aspect of the invention, there is provided a method of producing a recombinant isolated protein according to the first aspect, said method comprising the steps of:
(i) culturing a host cell containing an expression vector according to the third aspect such that said polypeptide is expressed in said host cell; and
(ii) isolating said recombinant polypeptide.

In a sixth aspect, the invention provides an antibody or antibody fragment that binds to a protein of the invention, fragment, variant or derivative thereof.

In a seventh aspect, the invention provides a method of detecting *N. meningitidis* in a biological sample suspected of containing same, said method comprising the steps of:—
(i) isolating the biological sample from an individual;
(ii) combining the above-mentioned antibody or antibody fragment with the biological sample; and
(iii) detecting specifically bound antibody or antibody fragment which indicates the presence of *N. meningitidis*.

In an eighth aspect, there is provided a method of detecting *N. meningitidis* bacteria in a biological sample suspected of containing said bacteria, said method comprising the steps of:—
(i) isolating the biological sample from a patient;
(ii) detecting a nucleic acid sequence according to the second-mentioned aspect in said sample which indicates the presence of said bacteria.

In a ninth aspect, the invention provides a method for diagnosing infection of an individual by *N. meningitidis*, said method comprising the steps of:—
(i) contacting a biological sample from an individual with a polypeptide, fragment, variant or derivative of the invention; and
(ii) determining the presence or absence of a complex between said polypeptide, fragment, variant or derivative and *N. meningitidis*-specific antibodies in said sample, wherein the presence of said complex is indicative of said infection.

Preferably, the individual is a mammal.

More preferably, the individual is a human.

In a tenth aspect, the invention also extends to the use of an isolated protein according to the first-mentioned aspect, the use of isolated nucleic acids according to the second aspect or the use of the antibody or antibody fragment mentioned above in a kit for detecting *N. meningitidis* bacteria in a biological sample.

In an eleventh aspect of the invention, there is provided a pharmaceutical composition comprising an isolated protein according to the first mentioned aspect.

Preferably, said pharmaceutical composition is a vaccine.

In a twelfth aspect, the invention provides a method of preventing infection of a patient by *N. meningitidis*, comprising the step of administrating a pharmaceutically effective amount of the above-mentioned vaccine.

In a thirteenth aspect, the invention provides a method of identifying an immunogenic fragment of an isolated protein, variant or derivative according to the first mentioned aspect, comprising the steps of:—
(i) producing a fragment of said polypeptide, variant or derivative;
(ii) administering said fragment to an individual; and
(iii) detecting an immune response in said individual, which response includes production of elements which specifically bind *N. meningitidis* and/or said polypeptide, variant or derivative, and/or a protective effect against *N. meningitidis* infection.

Preferably, the individual is a mammal.

More preferably, the individual is a human.

BRIEF DESCRIPTION OF THE FIGURES AND TABLES

Table 1: Identification of amino acids of the conserved regions (C1, C2, C3, C4 and C5) and variable regions (V1, V2, V3 and V4) of an NhhA polypeptide from each of ten (10) indicated strains of *N. meningitidis*. Relevant SEQ ID NOS are also indicated. Column 1=strain designation. SEQ ID NOS:1-9 were previously described in copending application WO99/31132; the sequences of NhhA and nhhA of strain Z2491 were obtained from the database of the Wellcome Trust/Sanger Institute genomic sequencing project for *N. meningitidis*; column 2=amino acid numbering of C1 region; column 3=amino acid numbering of V1 region; column 4=amino acid numbering of C2 region; column 5=amino acid numbering of V2 region; column 6=amino acid numbering of C3 region, column 7=amino acid numbering of V2 region; column 8=amino acid numbering of C4 region; column 9=amino acid numbering of V4 region; column 10=amino acid numbering of C5 region. Note that the amino acid numbering of the consensus sequence (SEQ ID NO:11) is also indicated.

Table 2: Table of amino acid substitutions.

FIG. 1 (comprising FIGS. 1A-1E): Amino acid sequence alignments of NhhA polypeptide amino acid sequences from ten (10) *N. meningitidis* strains (SEQ ID NOS:1-10) together with consensus sequence (SEQ ID NO:11). Strain names and polypeptide sequences used in this alignment correspond to the strain names and SEQ ID NOS in column 1 of Table 1. Amino acids are indicated by standard single letter abbreviations. Consensus amino acids are shown only where residues are completely conserved. Conserved regions (double underlined, labeled C1, C2, C3, C4, C5) and variable regions (single underlined, labeled V1, V2, V3, V4) are indicated under the consensus sequence.

FIG. 2 (comprising FIGS. 2A-2H): Nucleotide sequence alignment of nhhA nucleic acids from ten (10) *N. meningitidis* strains, which sequences encode the amino acid sequences of FIG. 1. Regions C1, C2, C3, C4, C5 and V1, V2, V3, V4 are as described in FIG. 1 and Table 1.

Figure 3B:
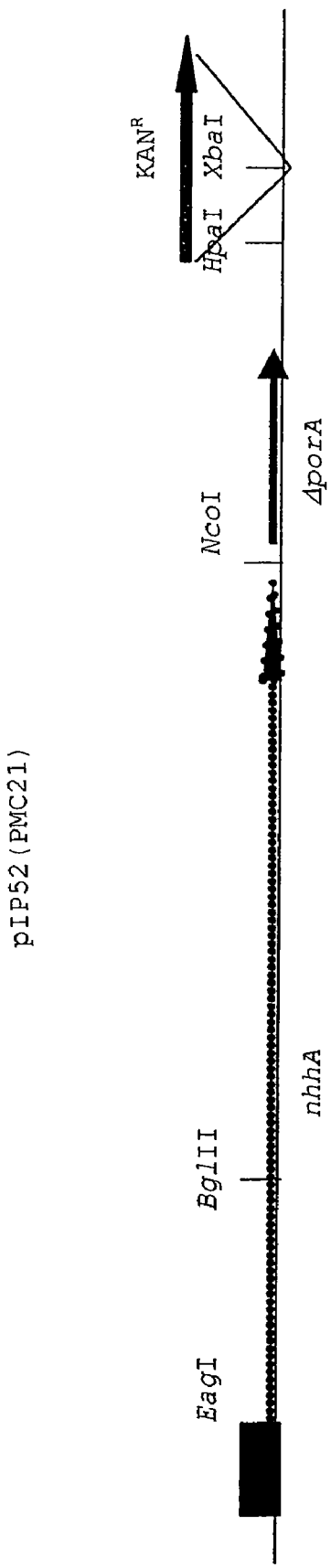

FIG. 3 (comprising FIGS. 3A and 3B): Plasmid map corresponding to pCO14K with a PCR amplification product encoding wild-type PMC21 NhhA operably linked to the porA promoter. (Not drawn to scale) FIG. 3A: Solid arrows indicate the arrangement of the porA and kanR genes in pCO14K. Oligonucleotide primers HOMP5' and HOMP3'AN used to amplify the nhhA gene of strain PMC21 are shown. The nhhA gene is shown by dotted arrow, the porA promoter by a black box, and EagI and NcoI restriction sites used to replace porA with nhhA in as described in Example 2 are shown. FIG. 3B Arrangement of genes in pIP52(PMC21), as described in Example 2. The BglII site used to construct a mutant as described in Example 4 is shown.

Figure 4A:
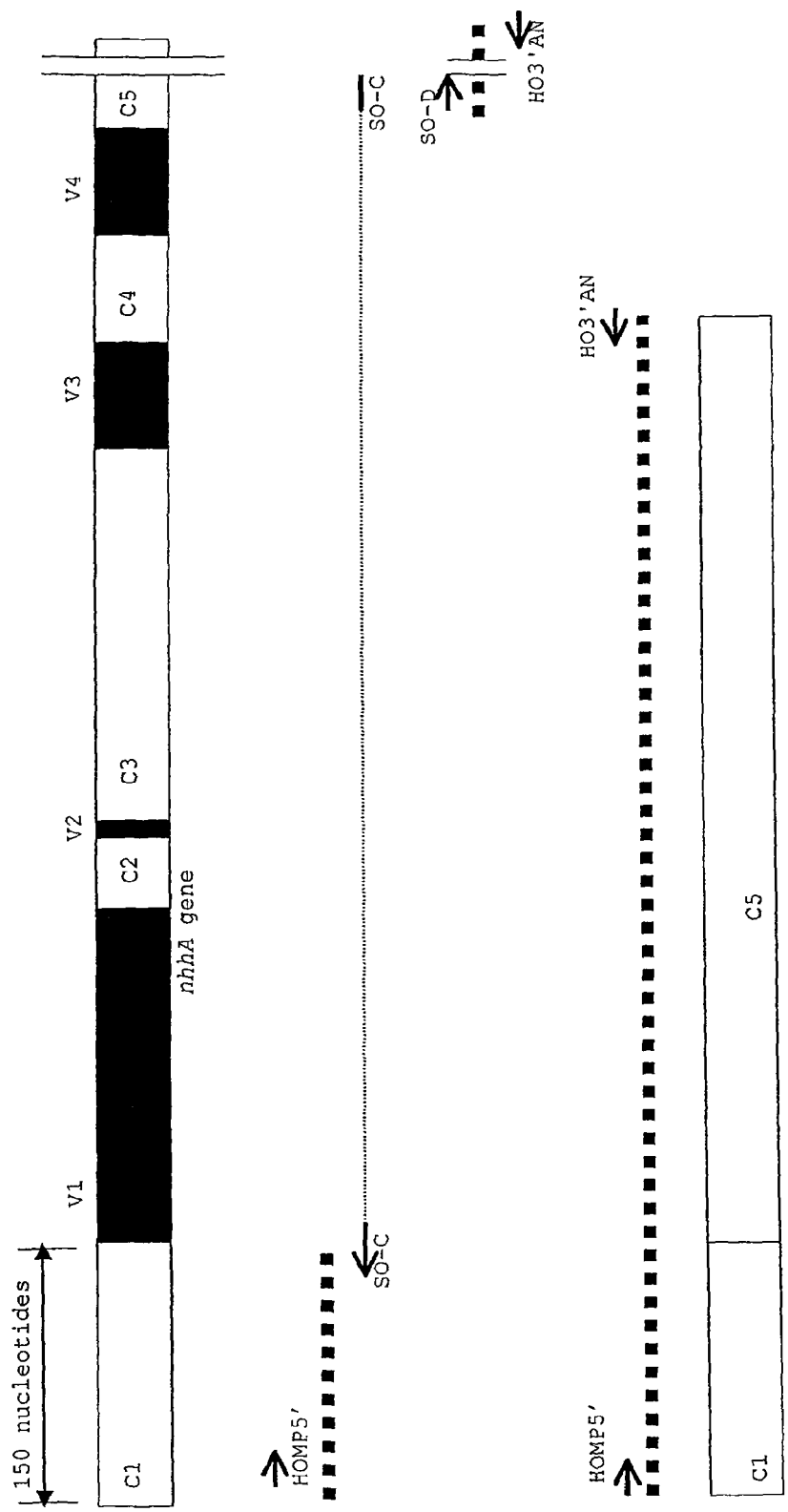
Figure 4B:
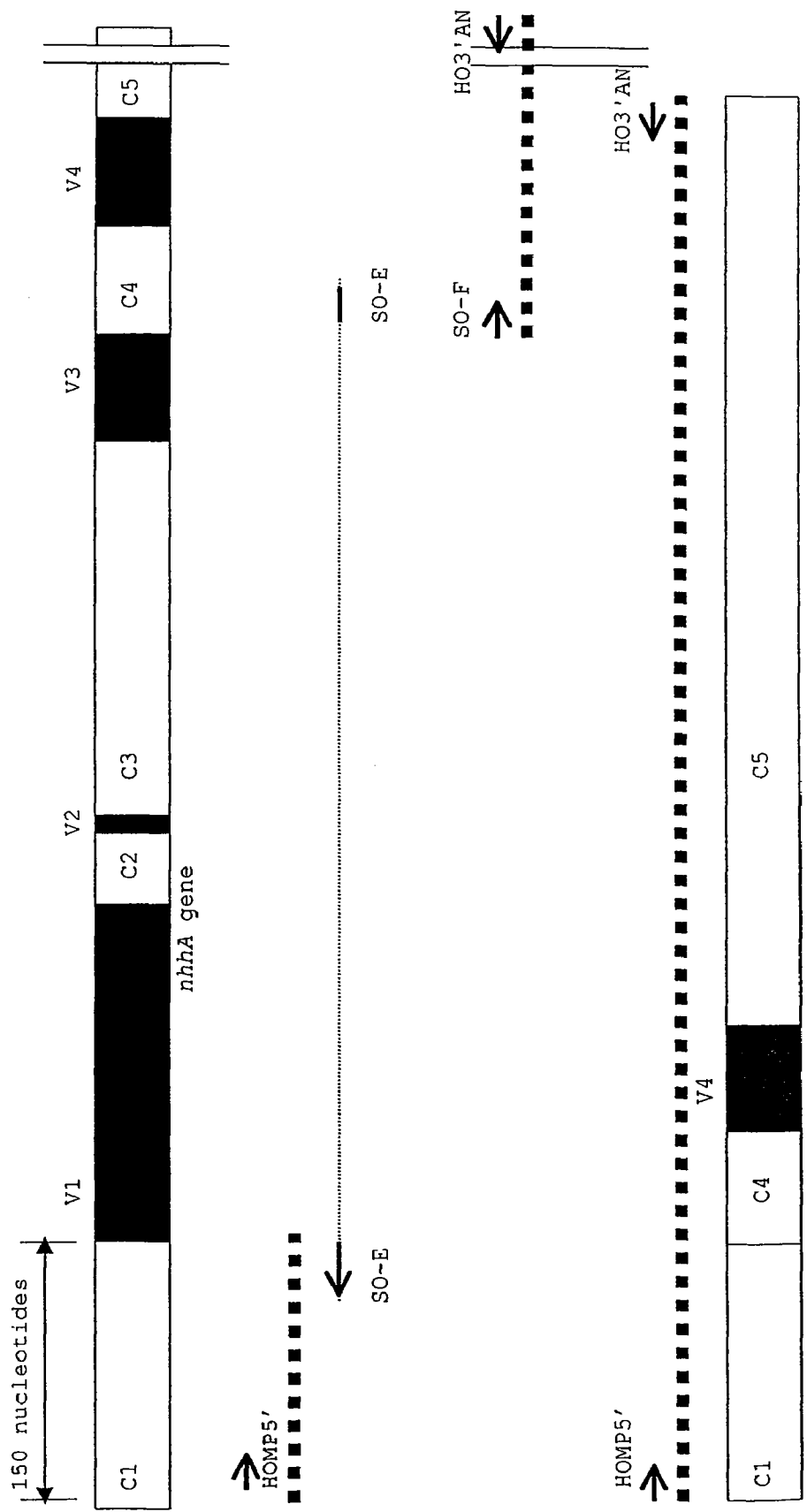
Figure 4C:
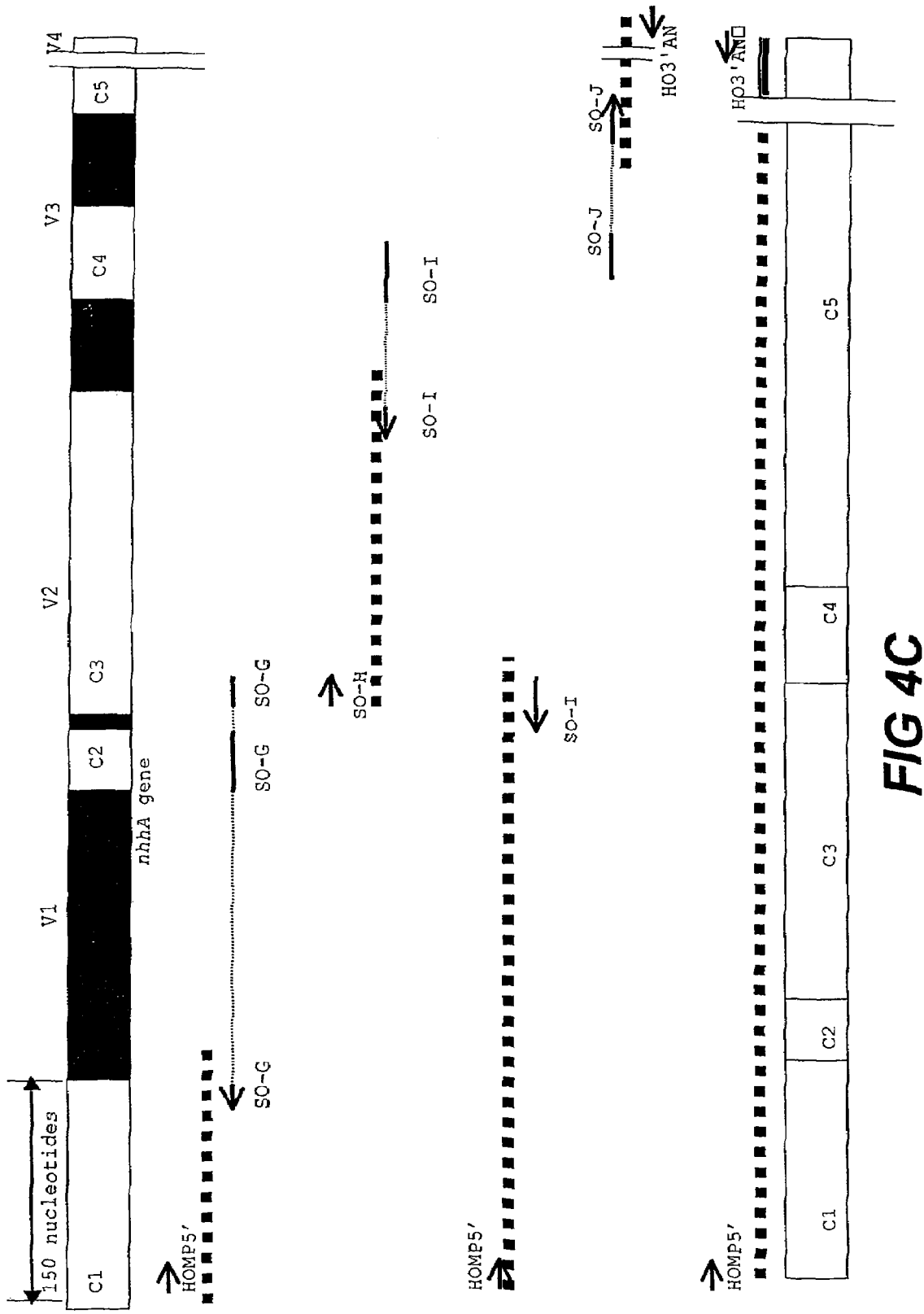

FIG. 4 (comprising FIGS. 4A-4C): Schematic representation of Splice Overlap Extension PCR strategy for deletion of specific regions of NhhA polypeptides. A schematic of the wild-type nhhA gene is shown at the top of FIGS. 4A-C, and the recombinant nhhA is shown at the bottom of these figures, with variable regions shown as black and constant regions by unfilled boxes. Arrows indicate approximate location of oligonucleotide primers. Vertical hatched lines indicate amplification products. Where oligonucleotide sequence is from discontinuous regions of an nhhA nucleic acid, this is shown by a dotted line between such discontinuous regions. Approximate scale indicated. Double vertical lines indicate that only a portion of the C5 region is shown. FIG. 4A: shows the strategy as described in Example 6. FIG. 4B: shows the strategy as described in Example 7. FIG. 4C: shows the strategy as described in Example 8.

FIG. 5 (comprising FIGS. 5A and 5B): FIG. 5A Amino acid sequence of PMC 21 NhhA deletion mutant polypeptide (SEQ ID NO:23) produced in Example 4; and FIG. 5B encoding nucleotide sequence (SEQ ID NO:28).

FIG. 6 (comprising FIGS. 6A and 6B): FIG. 6A Amino acid sequence of H41N NhhA deletion mutant polypeptide (SEQ ID NO:24) produced in Example 5; and FIG. 6B encoding nucleotide sequence (SEQ ID NO:29).

FIG. 7 (comprising FIGS. 7A and 7B): FIG. 7A Amino acid sequence of PMC21 NhhA deletion mutant polypeptide (SEQ ID NO:25) produced by splice overlap PCR in Example 6; and FIG. 7B encoding nucleotide sequence (SEQ ID NO:30).

FIG. 8 (comprising FIGS. 8A and 8B): FIG. 8A Amino acid sequence of PMC21 NhhA deletion mutant polypeptide (SEQ ID NO:26) produced by splice overlap PCR in Example 7; and FIG. 8B encoding nucleotide sequence (SEQ ID NO:31).

FIG. 9 (comprising FIGS. 9A and 9B): FIG. 9A Amino acid sequence of PMC21 NhhA deletion mutant polypeptide (SEQ ID NO: 27) produced by splice overlap PCR in Example 8; and FIG. 9B encoding nucleotide sequence (SEQ ID NO:32).

FIG. 10 (comprising FIGS. 10A and 10B): Amino acid sequence alignments of wild type and NhhA deletion mutant polypeptide sequences. These polypeptides were produced as described in Example 2, Example 3, Example 4 and Example 5. Amino acids are indicated by the one letter abbreviation. Conserved regions labeled C1, C2, C3, C4 and C5 corresponding to those defined in Table 1 and FIG. 1 are indicated by double underlining of full length sequences from H41 and PMC21, and variable regions labeled V1, V2, V3, V4 corresponding to those defined in Table 1 and FIG. 1 are indicated by single underlining of full length sequences from H41 and PMC21.

Figure 11:
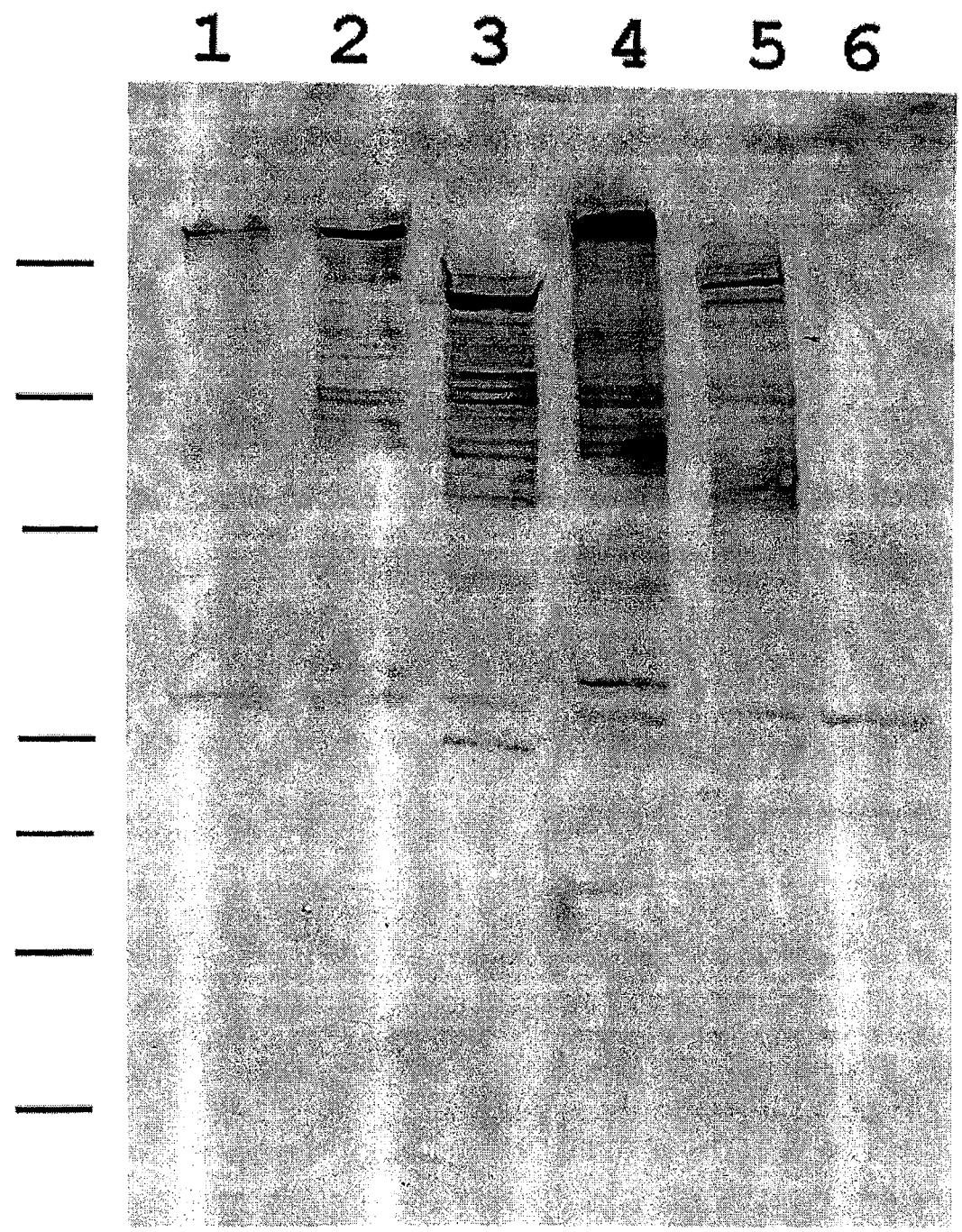

FIG. 11: Western immunoblot showing over expressed NhhA. 45 µg total cell protein was separated on 4-20% gradient SDS-PAGE before transfer to a nitrocellulose filter and western immunoblot as described in Example 9. Lane 1: Parental strain showing wild-type level of NhhA expression. Lane 2: Strain P6 (overexpresses PMC 21 NhhA as described in Example 2). Lane 3: Strain PΔ6 (overexpresses the truncated PMC 21NhhA described in Example 4). Lane 4: Strain H14 (overexpresses H41 NhhA described in Example 3). Lane 5: Strain HΔ8 (overexpresses the truncated H41 NhhA described in Example 5). Lane 6: Strain 2A (NhhA expression abolished by mutation of nhhA gene as described in International Publication WO99/31132). Migration of standards is indicated: 185 kDa, 119 kDa, 85 kDa, 62 kDa, 51.2 kDa, 38.2 kDa, 22.4 kDa. Wild-type NhhA polypeptide is present as a high molecular weight immunoreactive band present in lane 1 but absent from lane 6.

Figure 12:
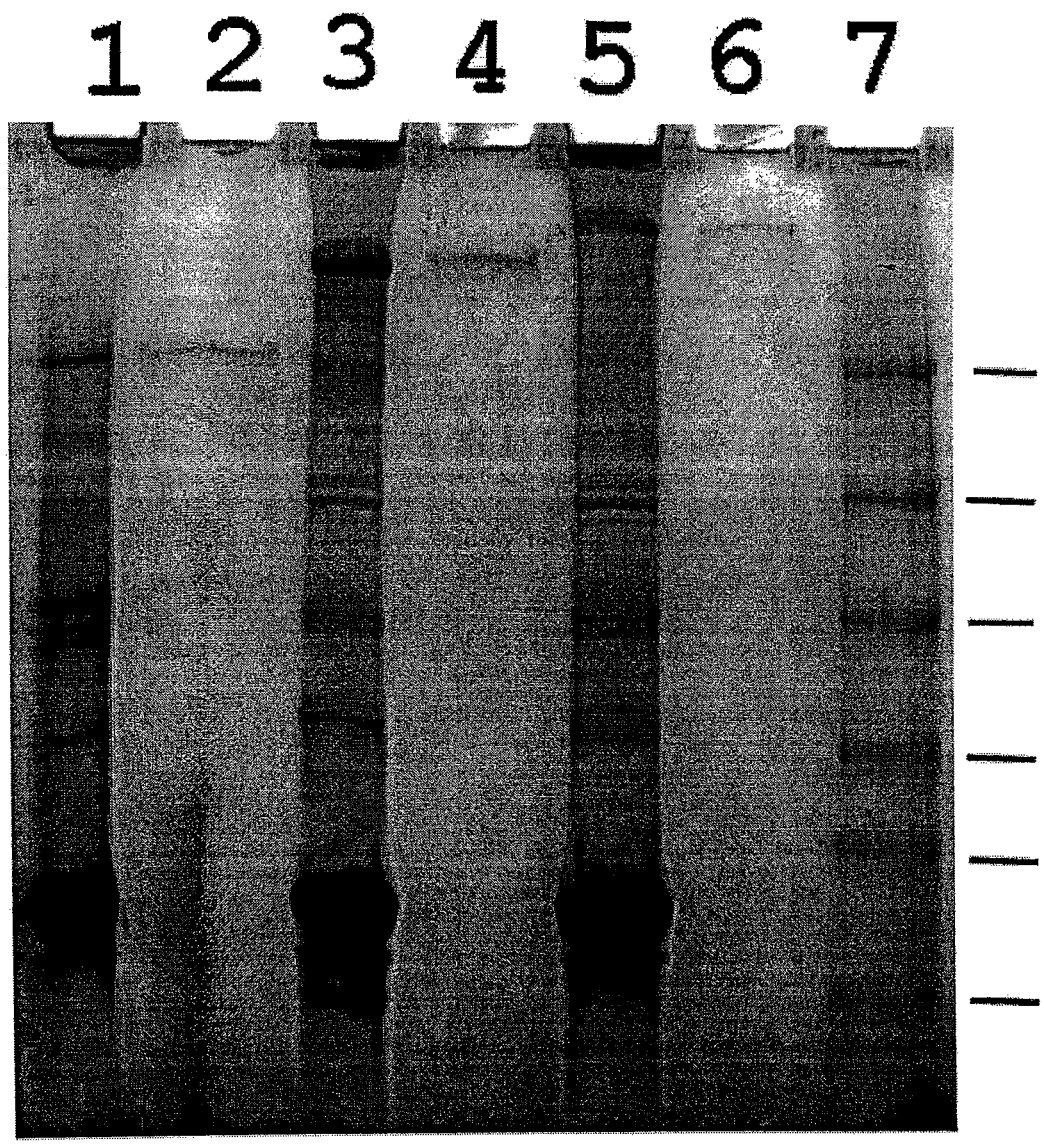

FIG. 12: Isolated NhhA deletion mutant polypeptides. NhhA polypeptides were isolated as described in Example 9 before separation on 4-20% SD-PAGE. The polyacrylamide gel was Coomassie stained. Lane 1: OMC preparation of Strain overexpressing the truncated PMC21 NhhA polypeptide described in Example 6. Lane 2: Purified truncated PMC21 NhhA polypeptide. Lane 3: OMC preparation of Strain over-expressing the truncated PMC21 NhhA polypeptide described in Example 4. Lane 4: Purified truncated PMC21 NhhA polypeptide. Lane 5: OMC preparation of a strain overexpressing PMC21 NhhA polypeptide described in Example 2. Lane 6: Purified PMC21 NhhA polypeptide. Lane 7: Molecular weight standards of 173 kDa, 111 kDa, 80 kDa, 61 kDa, 49 kDa, 36 kDa. Note that the reactive high molecular weight species in all lanes except 6 probably represents multimers of NhhA polypeptides. Other bands are probably less stable forms of NhhA or breakdown products. Note these are absent from lane 6.

Figures 13A, 13B, 13C:
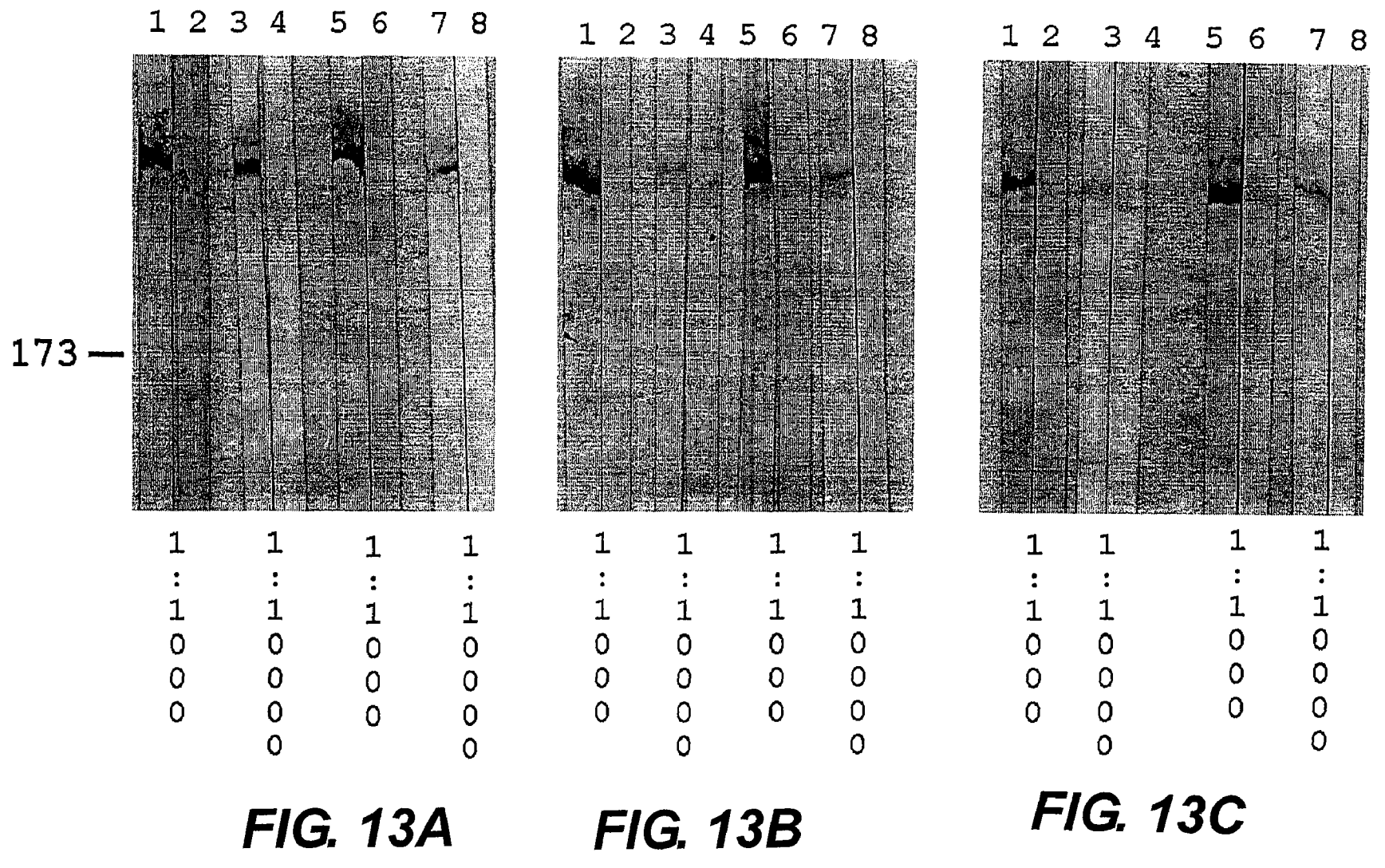

FIG. 13 (comprising FIGS. 13A-13C): Western Immunoblot using anti-NhhA protein mouse sera. In all of FIGS. 13A-13C, lanes 1, 3, 5, 7, contain OMC of Strain over expressing PMC21 NhhA polypeptide, and lanes 2, 4, 6, and 8 contain OMC of strain 2A which does not express NhhA. FIG. 13A: Lanes 1 and 2: mouse A inoculated with wild-type PMC21 NhhA at a 1:1000 dilution. Lanes 3 and 4: mouse A inoculated with wild-type PMC21 NhhA at a 1:10.000 dilution. Lanes 5 and 6, mouse B inoculated with wild-type PMC21 NhhA at a 1:1000 dilution. Lanes 7 and 8: mouse B inoculated with wild-type PMC21 NhhA at a 1:10.000 dilution. FIG. 13B: Lanes 1 & 2: mouse C inoculated with truncated PMC21 NhhA polypeptide (Example 4) at a 1:1000 dilution. Lanes 3 & 4: mouse C inoculated with truncated PMC21 NhhA polypeptide (Example 4) at a 1:10,000 dilution. Lanes 5 & 6: mouse D inoculated with truncated PMC21 NhhA (Example 4) at a 1:1000 dilution. Lanes 7 and 8: mouse D inoculated with truncated PMC21 NhhA (Example 4) at a 1:1000 dilution. FIG. 13C: Lanes 1 & 2: mouse E inoculated with truncated PMC21 NhhA (Example 6) at a 1:1000 dilution. Lanes 3 and 4: mouse E inoculated with truncated PMC21 NhhA (Example 6) at a 1:10,000 dilution. Lanes 5 & 6: mouse F inoculated with truncated PMC21 NhhA (Example 6) at a 1:1000 dilution. Lanes 7 & 8: mouse F inoculated with truncated PMC21 NhhA (Example 6) at a 1:1000 dilution.

FIG. 14 (comprising FIGS. 14A-14G): Predicted mature NhhA polypeptide deletion mutants. FIG. 14A: predicted mature protein described in Example 2 (SEQ ID NO:33); FIG. 14B: predicted mature protein described in Example 3 (SEQ ID NO:34); FIG. 14C: predicted mature protein described in Example 4 (SEQ ID NO:35); FIG. 14D: predicted mature protein described in Example 5 (SEQ ID NO:36); FIG. 14E: predicted mature protein described in Example 6 (SEQ ID NO:37); FIG. 14F: predicted mature protein described in Example 7 (SEQ ID NO:38); and FIG. 14G: predicted mature protein described in Example 8 (SEQ ID NO:39).

DETAILED DESCRIPTION OF THE INVENTION

Throughout this specification, unless the context requires otherwise, the words "comprise", "comprises" and "comprising" will be understood to imply the inclusion of a stated integer or group of integers but not the exclusion of any other integer or group of integers.

With regard to nomenclature, NhhA is used herein when reference is made to proteins of the invention, while nhhA is used herein when reference is made to nucleic acids of the invention. It will also be understood that NhhA/nhhA proteins and nucleic acids include the HiaNm/hianm proteins and nucleic acids referred to in WO99/31132, for example, without limitation thereto.

The present invention is predicated, at least in part, by the elucidation of conserved and less-conserved regions in the NhhA polypeptide in ten (10) strains of *N. meningitidis*. Corresponding regions are predicted to be conserved in other allelic variants of the exemplified NhhA polypeptides.

It will be appreciated that central to the present invention is the realization that by deleting non-conserved amino acids in a wild-type NhhA polypeptide to form a modified NhhA polypeptide of the invention, an immune response may be elicited upon immunization by said polypeptide of the invention which, by directing the immune response against conserved epitopes, will provide protection against one or more heterologous strains of *N. meningitidis*.

As used herein, "non-conserved" amino acids are amino acid residues present in a wild-type NhhA polypeptide from a first *N. meningitidis* strain, but which are not present in a wild-type NhhA polypeptide from one or more other strains.

Suitably, the polypeptides of the first aspect have at least a portion of one of the V1, V2, V3 or V4 regions deleted with respect to the corresponding wild-type sequence, and accordingly, may be collectively referred to as examples of "deletion mutants".

It will be appreciated that the present inventors have identified the V1, V2, V3 and V4 regions as being regions of wild-type NhhA polypeptides having relatively high frequencies of non-conserved amino acids compared to the relatively conserved C1-5 regions.

Of the V regions, the V1 (hypervariable) and V2 regions have the highest frequency of non-conserved amino acids, while V3 and V4 have relatively lower frequencies. However, the V1 region constitutes a more significant proportion of wild-type NhhA polypeptides than does the V2 region (in terms of total amino acids). Therefore, it is preferred that the isolated proteins according to the first-mentioned aspect have at least a substantial portion of the V1 region deleted.

It will also be realized by the skilled person that in constructing said deletion mutants, "shuffling" of regions between NhhA polypeptides of different *N. meningitidis* strains is possible. For example, an NhhA polypeptide of the invention may comprise a H41 C1 region together with a PMC21 C5 region.

Such "shuffling" is particularly well-suited to recombinant DNA methods.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native or recombinant form.

By "protein" is meant an amino acid polymer. The amino acids may be natural or non-natural amino acids as are well understood in the art.

A "peptide" is a protein having no more than fifty (50) amino acids.

A polypeptide is a protein having fifty (50) or more amino acids.

As used herein, the phrase "elicits an immune response" refers to the ability of an isolated polypeptide of the invention to produce an immune response in a mammal to which it is administered, wherein the response is directed to *N. meningitidis* and/or said polypeptide. Preferably, the immune response includes production of bactericidal antibodies. More preferably, the immune response is protective against *N. meningitidis* infection.

"Strain-specific" is used herein in the context of an immune response which is directed to, or at least predominantly directed to, an autologous *N. meningitidis* strain.

As used herein, "cross-reactive" means an ability of a polypeptide of the invention to elicit an immune response directed to one or more heterologous *N. meningitidis* strains.

As used herein, "cross-protective" means an ability of a polypeptide of the invention to elicit an immune response and thereby provide protection against infection by one or more heterologous *N. meningitidis* strains.

Therefore, in light of the foregoing, said polypeptide of the invention may be referred to herein as an "immunogen", or as being "immunogenic".

Although for the purposes of the present invention, said modified NhhA proteins have been exemplified by the amino acid sequences set forth in FIGS. 5 to 9 (SEQ ID NOS:23-27) and FIG. 14, the present invention also contemplates fragments, derivatives and variants (such as allelic variants) of the exemplified proteins.

For example, amino acids can be deleted from any of the C1-5 sequences set forth in FIG. 1, while not all non-conserved amino acids in the V1-4 regions need be deleted in order to reduce strain-specific immunogenicity. Therefore, isolated proteins of the invention may include fragments of the C1-5 and V1-4 regions.

Indeed, as will be described hereinafter in the Examples, it may be advantageous for the purposes of recombinant DNA-based production of polypeptides of the invention, to delete one or a few amino acids of a C1, C2, C3, C4 and/or C5 region or a V1, V2, V3 and/or V4 region in the interests of utilizing convenient restriction endonuclease sites and achieving high level expression of stable, immunogenic protein.

In one embodiment, a "fragment" includes an amino acid sequence that constitutes less than 100%, but at least 20%, preferably at least 50%, more preferably at least 80% or even more preferably at least 90% of said C1, C2, C3, C4 or C5 regions.

Fragments, for example, may be peptides comprising as few as twelve amino acids such as the C2 region (SEQ ID NO:11) or sequences of at least twenty contiguous amino acids, or more than one hundred contiguous amino acids corresponding to some or all of the C1, C2, C3, C4 and/or C5 regions described herein.

Other fragments exemplified herein are modified NhhA polypeptides of the invention which have undergone post-translational processing to form a mature polypeptide, such as shown in FIG. 14.

In another embodiment, a "fragment" is a small peptide, for example of at least 6, preferably at least 10 and more preferably at least 20 amino acids in length, which comprises one or more antigenic determinants or epitopes derived from modified NhhA proteins of the invention. Larger fragments comprising more than one peptide are also contemplated, and may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of a polypeptide of the invention with proteinases such as endoLys-C, endoArg-C, endoGlu-C and staphylococcins V8-protease. The digested fragments can be purified by, for example, high performance liquid chromatographic (HPLC) techniques.

As used herein, "variant" polypeptides are polypeptides of the invention in which one or more amino acids have been replaced by different amino acids. It is well understood in the art that some amino acids may be changed to others with broadly similar properties without changing the nature of the activity of the polypeptide (conservative substitutions). Exemplary conservative substitutions in the polypeptide may be made according to Table 2.

Substantial changes in function are made by selecting substitutions that are less conservative than those shown in Table 2. Other replacements would be non-conservative substitutions and relatively fewer of these may be tolerated. Generally, the substitutions which are likely to produce the greatest changes in a polypeptide's properties are those in which (a) a hydrophilic residue (e.g., Ser or Thr) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp) or (d) a residue having a bulky side chain (e.g., Phe or Trp) is substituted for, or by, one having a smaller side chain (e.g., Ala, Ser) or no side chain (e.g., Gly).

The term "variant" also includes NhhA polypeptides of the invention produced from allelic variants of the sequences exemplified in this specification.

NhhA polypeptide variants may fall within the scope of the term "polypeptide homologs".

Polypeptide homologs share at least 70%, preferably at least 80% and more preferably at least 90% sequence identity with the amino acid sequences of modified NhhA polypeptides of the invention as hereinbefore described.

As generally used herein, a "homolog" shares a definable nucleotide or amino acid sequence relationship with a nucleic acid or polypeptide of the invention as the case may be.

For example, such homologs are contemplated as having amino acid sequences that differ from those exemplified herein, but which are immunogenic and provide cross-protective immunity.

Specifically excluded from the scope of the term "homologs" are wild-type NhhA polypeptides and nhhA nucleic acids.

Included within the scope of homologs are "orthologs", which are functionally-related polypeptides and their encoding nucleic acids, isolated from bacterial species other than *N. meningitidis*.

Terms used herein to describe sequence relationships between respective nucleic acids and polypeptides include "comparison window", "sequence identity", "percentage of sequence identity" and "substantial identity". Because respective nucleic acids/polypeptides may each comprise (1) only one or more portions of a complete nucleic acid/polypeptide sequence that are shared by the nucleic acids/polypeptides, and (2) one or more portions which are divergent between the nucleic acids/polypeptides, sequence comparisons are typically performed by comparing sequences over a "comparison window" to identify and compare local regions of sequence similarity. A "comparison window" refers to a conceptual segment of typically 12 contiguous residues that is compared to a reference sequence. The comparison window may comprise additions or deletions (i.e., gaps) of about 20% or less as compared to the reference sequence (which does not comprise additions or deletions) for optimal alignment of the respective sequences. Optimal alignment of sequences for aligning a comparison window may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 253389, which is incorporated herein by reference.

A detailed discussion of sequence analysis can be found in Unit 19.3 of CURRENT PROTOCOLS 1N MOLECULAR BIOLOGY Eds. Ausubel et al. (John Wiley & Sons Inc NY, 1995-1999).

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for windows; available from Hitachi Software engineering Co., Ltd., South San Francisco, Calif., USA).

Thus, it is well within the capabilities of the skilled person to prepare polypeptide homologs of the invention, such as variants as hereinbefore defined, by recombinant DNA technology. For example, nucleic acids of the invention can be mutated using either random mutagenesis for example using transposon mutagenesis, or site-directed mutagenesis. The resultant DNA fragments are then cloned into suitable expression hosts such as *E. coli* using conventional technology and clones that retain the desired activity are detected. Where the clones have been derived using random mutagenesis techniques, positive clones would have to be sequenced in order to detect the mutation.

As used herein, "derivative" polypeptides are polypeptides of the invention which have been altered, for example by conjugation or complexing with other chemical moieties or by post-translational modification techniques as would be understood in the art. Such derivatives include amino acid deletions and/or additions to NhhA polypeptides of the invention, or variants thereof, wherein said derivatives elicit an immune response.

"Additions" of amino acids may include fusion of the polypeptides or variants thereof with other polypeptides or proteins. In this regard, it will be appreciated that the polypeptides or variants of the invention may be incorporated into larger polypeptides, and such larger polypeptides may also be expected to be immunogenic. The polypeptides as described above may be fused to a further protein, for example, which is not derived from N. meningitidis. The other protein may, by way of example, assist in the purification of the protein. For instance a polyhistidine tag, or a maltose binding protein may be used. Alternatively, it may produce an immune response which is effective against N. meningitidis or it may produce an immune response against another pathogen. Other possible fusion proteins are those which produce an immunomodulatory response. Particular examples of such proteins include Protein A or glutathione S-transferase (GST). In addition, the polypeptide may be fused to an oligosaccharide based vaccine component where it acts as a carrier protein.

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention. Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4,6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

The invention also contemplates covalently modifying a polypeptide, fragment or variant of the invention with dinitrophenol, in order to render it immunogenic in humans.

Isolated proteins of the invention (inclusive of fragments, variants, derivatives and homologs) may be prepared by any suitable procedure known to those of skill in the art.

For example, the protein may be prepared as a recombinant polypeptide by a procedure including the steps of:
  (i) preparing an expression construct which comprises a modified nhhA nucleic acid of the invention, operably linked to one or more regulatory nucleotide sequences;
  (ii) transfecting or transforming a suitable host cell with the expression construct; and
  (iii) expressing the recombinant polypeptide in said host cell.

A number of Examples will be provided hereinafter which describe production of modified nhhA nucleic acids of the invention by PCR.

In one particular embodiment, PCR is splice overlap PCR, as will be described hereinafter, which method is based on that described in Ho et al., 1989, Gene 77 51, and by Horton et al., 1989, Gene 77 61, which are both incorporated herein by reference.

For the purposes of host cell expression, the recombinant nucleic acid is operably linked to one or more regulatory sequences in an expression vector.

An "expression vector" may be either a self-replicating extra-chromosomal vector such as a plasmid, or a vector that integrates into a host genome.

By "operably linked" is meant that said regulatory nucleotide sequence(s) is/are positioned relative to the recombinant nucleic acid of the invention to initiate, regulate or otherwise control transcription.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences.

Constitutive or inducible promoters as known in the art are contemplated by the invention. The promoters may be either naturally occurring promoters, or hybrid promoters that combine elements of more than one promoter.

In a preferred embodiment, the expression vector contains a selectable marker gene to allow the selection of transformed host cells. Selectable marker genes are well known in the art and will vary with the host cell used.

In an embodiment, the expression vector is pCO14K, which has a porA promoter and kanamycin selection gene, as will be described in detail hereinafter. According to this embodiment, the host cell is a bacterium selected from the group consisting of E. coli and N. meningitidis.

The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide.

In order to express said fusion polypeptide, it is necessary to ligate a nucleotide sequence according to the invention into the expression vector so that the translational reading frames of the fusion partner and the nucleotide sequence of the invention coincide.

Well known examples of fusion partners include, but are not limited to, glutathione-S-transferase (GST), Fc portion of human IgG, maltose binding protein (MBP) and hexahistidine ($HIS_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

A preferred fusion partner is MBP, which is described hereinafter in Example 11.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing sub-cellular localization of the fusion polypeptide of the invention, or for isolating cells which express the fusion polypeptide of the invention. Flow cytometric methods such as fluorescence activated cell sorting (FACS) are particularly useful in this latter application.

Preferably, the fusion partners also have protease cleavage sites, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-myc, influenza virus haemagglutinin and FLAG tags.

As hereinbefore, polypeptides of the invention may be produced by culturing a host cell transformed with said expression construct comprising a nucleic acid encoding a polypeptide, or polypeptide homolog, of the invention. The conditions appropriate for protein expression will vary with the choice of expression vector and the host cell. This is easily ascertained by one skilled in the art through routine experimentation.

Suitable host cells for expression may be prokaryotic or eukaryotic. One preferred host cell for expression of a polypeptide according to the invention is a bacterium. The bacterium used may be *Escherichia coli* or *N. meningitidis*.

In a preferred embodiment, the host cell is *N. meningitidis* which has been modified so as to not express PorA, Opa, Opc or capsular polysaccharide and expresses a desired lipopolysaccharide phenotype.

Alternatively, the host cell may be an insect cell such as, for example, SF9 cells that may be utilized with a baculovirus expression system.

The recombinant protein may be conveniently prepared by a person skilled in the art using standard protocols as for example described in Sambrook, et al., MOLECULAR CLONING. A Laboratory Manual (Cold Spring Harbor Press, 1989), incorporated herein by reference, in particular Sections 16 and 17; CURRENT PROTOCOLS IN MOLECULAR BIOLOGY Eds. Ausubel et al., (John Wiley & Sons, Inc. 1995-1999), incorporated herein by reference, in particular Chapters 10 and 16; and CURRENT PROTOCOLS IN PROTEIN SCIENCE Eds. Coligan et al., (John Wiley & Sons, Inc. 1995-1999) which is incorporated by reference herein, in particular Chapters 1, 5 and 6.

Preferred methods of expression of recombinant modified NhhA proteins of the invention, and methods for detection of expressed protein, are provided hereinafter in the Examples.

Nucleotide Sequences

The invention provides an isolated nucleic acid that encodes a modified NhhA protein of the invention.

Preferably, said isolated nucleic acid has a nucleotide sequence that encodes one or more NhhA polypeptide constant (C) regions as described in FIGS. 1 and 2. The isolated nucleic acid may further encode one or more non-conserved (V region) amino acids such as also identified in FIGS. 1 and 2.

Particular embodiments of such isolated nucleic acids are provided in SEQ ID NOS:28-32 and FIGS. 5-9.

The term "nucleic acid" as used herein designates single- or double-stranded mRNA, RNA, cRNA and DNA, said DNA inclusive of cDNA and genomic DNA.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labeled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

The present invention also contemplates homologs of nucleic acids of the invention as hereinbefore defined.

Such nucleic acid homologs exclude nucleic acids encoding full-length wild-type NhhA polypeptides.

For example, nucleic acid homologs encode peptides and polypeptides, structurally related to NhhA V and C regions of the invention, that may be useful for the purposes of providing cross-protective immunity to *N. meningitidis* by immunization.

In one embodiment, nucleic acid homologs encode polypeptide homologs of the invention, inclusive of variants, fragments and derivatives thereof.

In another embodiment, nucleic acid homologs share at least 60%, preferably at least 70%, more preferably at least 80%, and even more preferably at least 90% sequence identity with the nucleic acids of the invention.

In yet another embodiment, nucleic acid homologs hybridize to nucleic acids of the invention under at least low stringency conditions, preferably under at least medium stringency conditions and more preferably under high stringency conditions.

"Hybridize and Hybridization" is used herein to denote the pairing of at least partly complementary nucleotide sequences to produce a DNA-DNA, RNA-RNA or DNA-RNA hybrid. Hybrid sequences comprising complementary nucleotide sequences occur through base-pairing between complementary purines and pyrimidines as are well known in the art.

In this regard, it will be appreciated that modified purines (for example, inosine, methylinosine and methyladenosine) and modified pyrimidines (thiouridine and methylcytosine) may also engage in base pairing.

"Stringency" as used herein, refers to temperature and ionic strength conditions, and presence or absence of certain organic solvents and/or detergents during hybridisation. The higher the stringency, the higher will be the required level of complementarity between hybridizing nucleotide sequences.

"Stringent conditions" designates those conditions under which only nucleic acid having a high frequency of complementary bases will hybridize.

Reference herein to low stringency conditions includes and encompasses:—
(i) from at least about 1% v/v to at least about 15% v/v formamide and from at least about 1 M to at least about 2 M salt for hybridisation at 42° C., and at least about 1 M to at least about 2 M salt for washing at 42° C.; and
(ii) 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at room temperature.

Medium stringency conditions include and encompass:—
(i) from at least about 16% v/v to at least about 30% v/v formamide and from at least about 0.5 M to at least about 0.9 M salt for hybridisation at 42° C., and at least about 0.5 M to at least about 0.9 M salt for washing at 42° C.; and
(ii) 1% Bovine Serum Albumin (BSA), 1 mM EDTA, 0.5 M $NaHPO_4$ (pH 7.2), 7% SDS for hybridization at 65° C. and (a) 2×SSC, 0.1% SDS; or (b) 0.5% BSA, 1 mM EDTA, 40 mM $NaHPO_4$ (pH 7.2), 5% SDS for washing at 42° C.

High stringency conditions include and encompass:—
(i) from at least about 31% v/v to at least about 50% v/v formamide and from at least about 0.01 M to at least about 0.15 M salt for hybridisation at 42° C., and at least about 0.01 M to at least about 0.15 M salt for washing at 42° C.;
(ii) 1% BSA, 1 mM EDTA, 0.5 M $NaHPO_4$ (pH 7.2), 7% SDS for hybridization at 65° C., and (a) 0.1×SSC, 0.1% SDS; or (b) 0.5% BSA, 1 mM EDTA, 40 mM $NaHPO_4$ (pH 7.2), 1% SDS for washing at a temperature in excess of 65° C. for about one hour; and
(iii) 0.2×SSC, 0.1% SDS for washing at or above 68° C. for about 20 minutes.

In general, washing is carried out at $T_m$=69.3+0.41 (G+C) %-12° C. In general, the $T_m$ of a duplex DNA decreases by about 1° C. with every increase of 1% in the number of mismatched bases.

Notwithstanding the above, stringent conditions are well known in the art, such as described in Chapters 2.9 and 2.10 of. Ausubel et al., supra, which are herein incorporated by reference. A skilled addressee will also recognize that various factors can be manipulated to optimize the specificity of the hybridization. Optimization of the stringency of the final washes can serve to ensure a high degree of hybridization.

Typically, complementary nucleotide sequences are identified by blotting techniques that include a step whereby nucleotides are immobilized on a matrix (preferably a synthetic membrane such as nitrocellulose), a hybridization step, and a detection step. Southern blotting is used to identify a complementary DNA sequence; northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in Ausubel et al., supra, at pages 2.9.1 through 2.9.20. According to such methods, Southern blotting involves separating DNA molecules according to size by gel electrophoresis, transferring the size-separated DNA to a synthetic membrane, and hybridizing the membrane bound DNA to a complementary nucleotide sequence.

In dot blotting and slot blotting, DNA samples are directly applied to a synthetic membrane prior to hybridization as above.

An alternative blotting step is used when identifying complementary nucleic acids in a cDNA or genomic DNA library, such as through the process of plaque or colony hybridization. Other typical examples of this procedure is described in Chapters 8-12 of Sambrook et al., supra which are herein incorporated by reference.

Typically, the following general procedure can be used to determine hybridization conditions. Nucleic acids are blotted/transferred to a synthetic membrane, as described above. A wild type nucleotide sequence of the invention is labeled as described above, and the ability of this labeled nucleic acid to hybridize with an immobilized nucleotide sequence analyzed.

A skilled addressee will recognize that a number of factors influence hybridization. The specific activity of radioactively labeled polynucleotide sequence should typically be greater than or equal to about $10^8$ dpm/µg to provide a detectable signal. A radiolabeled nucleotide sequence of specific activity $10^8$ to $10^9$ dpm/µg can detect approximately 0.5 pg of DNA. It is well known in the art that sufficient DNA must be immobilized on the membrane to permit detection. It is desirable to have excess immobilized DNA, usually 1-10 µg. Adding an inert polymer such as 10% (w/v) dextran sulfate (MW 500,000) or polyethylene glycol 6000 during hybridization can also increase the sensitivity of hybridization (see Ausubel et al., supra at 2.10.10).

To achieve meaningful results from hybridization between a nucleic acid immobilized on a membrane and a labeled nucleic acid, a sufficient amount of the labeled nucleic acid must be hybridized to the immobilized nucleic acid following washing. Washing ensures that the labeled nucleic acid is hybridized only to the immobilized nucleic acid with a desired degree of complementarity to the labeled nucleic acid.

Methods for detecting labeled nucleic acids hybridized to an immobilized nucleic acid are well known to practitioners in the art. Such methods include autoradiography, chemiluminescent, fluorescent and colorimetric detection.

In another embodiment, nucleic acid homologs of the invention may be prepared according to the following procedure:
(i) obtaining a nucleic acid extract from a suitable host;
(ii) creating primers which are optionally degenerate wherein each comprises a portion of a nucleotide sequence of the invention; and
(iii) using said primers to amplify, via nucleic acid amplification techniques, one or more amplification products from said nucleic acid extract.

Suitably, the host is a bacterium.

Preferably, the host is of the genus *Neisseria*.

More preferably, the host is *N. meningitidis* or *N. lactamica*.

Primers useful according to nucleic acid sequence amplification methods include SEQ ID NOS:40-51 as described in detail hereinafter.

Suitable nucleic acid amplification techniques are well known to the skilled addressee, and include polymerase chain reaction (PCR) as for example described in Chapter 15 of Ausubel et al. supra, which is incorporated herein by reference; strand displacement amplification (SDA) as for example described in U.S. Pat. No. 5,422,252 which is incorporated herein by reference; rolling circle replication (RCR) as for example described in Liu et al., 1996, J. Am. Chem. Soc. 118 1587 and International application WO 92/01813 and Lizardi et al., (International Application WO 97/19193) which are incorporated herein by reference; nucleic acid sequence-based amplification (NASBA) as for example described by Sooknanan et al., 1994, Biotechniques 17 1077) which is incorporated herein by reference; and Q-β replicase amplification as for example described by Tyagi et al., 1996, Proc. Natl. Acad. Sci. USA 93 5395 which is incorporated herein by reference.

As used herein, an "amplification product" refers to a nucleic acid product generated by nucleic acid amplification techniques.

Antibodies

The invention also contemplates antibodies against the isolated proteins fragments, variants and derivatives of the invention. Antibodies of the invention may be polyclonal or monoclonal. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. Antibodies: A Laboratory Manual, Cold Spring Harbor, Cold Spring Harbor Laboratory, 1988, which are both herein incorporated by reference.

Generally, antibodies of the invention bind to or conjugate with a polypeptide, fragment, variant or derivative of the invention. For example, the antibodies may comprise polyclonal antibodies. Such antibodies may be prepared for example by injecting a polypeptide, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, supra, and in Harlow & Lane, 1988, supra.

In lieu of the polyclonal antisera obtained in the production species, monoclonal antibodies may be produced using the standard method as for example, described in an article by Köhler & Milstein, 1975, Nature 256, 495, which is herein incorporated by reference, or by more recent modifications thereof as for example, described in Coligan et al., CURRENT PROTOCOLS IN IMMUNOLOGY, supra by immortalizing spleen or other antibody producing cells derived from a production species which has been inoculated with one or more of the polypeptides, fragments, variants or derivatives of the invention.

The invention also includes within its scope antibodies which comprise Fc or Fab fragments of the polyclonal or monoclonal antibodies referred to above. Alternatively, the antibodies may comprise single chain Fv antibodies (scFvs) against the peptides of the invention. Such scFvs may be prepared, for example, in accordance with the methods described respectively in U.S. Pat. No. 5,091,513, European Patent No 239,400 or the article by Winter & Milstein, 1991, Nature 349 293, which are incorporated herein by reference.

The antibodies of the invention may be used for affinity chromatography in isolating natural or recombinant N. meningitidis polypeptides. For example reference may be made to immunoaffinity chromatographic procedures described in Chapter 9.5 of Coligan et al., CURRENT PROTOCOLS IN IMMUNOLOGY, supra.

The antibodies may be used to:
(i) screen expression libraries to identify variant polypeptides of the invention;
(ii) identify immunoreactive fragments or immunoreactive epitopes; and/or
(iii) detect N. meningitidis infection;
as will be described hereinafter but without limitation to these particular uses.

Detection of N. meningitidis

The presence or absence of N. meningitidis in an individual may be determined by isolating a biological sample from said individual, mixing an antibody or antibody fragment described above with the biological sample, and detecting specifically bound antibody or antibody fragment which indicates the presence of N. meningitidis in the sample.

The term "biological sample" as used herein refers to a sample that may be extracted, untreated, treated, diluted or concentrated from an individual, such as a patient. Suitably, the biological sample is selected from the group consisting of whole blood, serum, plasma, saliva, urine, sweat, ascitic fluid, peritoneal fluid, synovial fluid, amniotic fluid, cerebrospinal fluid, skin biopsy, and the like.

Any suitable technique for determining formation of the complex may be used. For example, an antibody or antibody fragment according to the invention having a label associated therewith may be utilized in immunoassays. Such immunoassays may include, but are not limited to, radioimmunoassays (RIAs), enzyme-linked immunosorbent assays (ELISAs) and immunochromatographic techniques (ICTs) which are well known those of skill in the art.

For example, reference may be made to Chapter 7 of Coligan et al., CURRENT PROTOCOLS IN IMMUNOLOGY, supra which discloses a variety of immunoassays that may be used in accordance with the present invention. Immunoassays may include competitive assays as understood in the art.

The label associated with the antibody or antibody fragment may include the following:
(A) direct attachment of the label to the antibody or antibody fragment;
(B) indirect attachment of the label to the antibody or antibody fragment; i.e., attachment of the label to another assay reagent which subsequently binds to the antibody or antibody fragment; and
(C) attachment to a subsequent reaction product of the antibody or antibody fragment.

The label may be selected from a group including a chromogen, a catalyst, an enzyme, a fluorophore, a chemiluminescent molecule, a lanthanide ion such as Europium ($Eu^{34}$), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes useful as labels is disclosed in U.S. Pat. No. 4,366,241, U.S. Pat. No. 4,843,000, and U.S. Pat. No. 4,849,338, all of which are herein incorporated by reference. Enzyme labels useful in the present invention include alkaline phosphatase, horseradish peroxidase, luciferase, β-galactosidase, glucose oxidase, lysozyme, malate dehydrogenase and the like. The enzyme label may be used alone or in combination with a second enzyme in solution.

Suitably, the fluorophore is selected from a group including fluorescein isothiocyanate (FITC), tetramethylrhodamine isothiocyanate (TRITL) or R-Phycoerythrin (RPE).

The invention also extends to a method for detecting infection of patients by N. meningitidis, said method comprising the steps of contacting a biological sample from a patient with a polypeptide, fragment, variant or derivative of the invention, and determining the presence or absence of a complex between said polypeptide, fragment, variant or derivative and *N. meningitidis*-specific antibodies in said serum, wherein the presence of said complex is indicative of said infection.

In a preferred embodiment, detection of the above complex is effected by detectably modifying said polypeptide, fragment, variant or derivative with a suitable label as is well known in the art and using such modified compound in an immunoassay as for example described above.

In another aspect, the invention provides a method of detecting *N. meningitidis* bacteria in a biological sample suspected of containing said bacteria, said method comprising the steps of isolating the biological sample from a patient, detecting a nucleic acid sequence according to the invention in said sample which indicates the presence of said bacteria. Detection of the said nucleic acid sequence may be determined using any suitable technique. For example, a labeled nucleic acid according to the invention may be used as a probe in a Southern blot of a nucleic acid extract obtained from a patient as is well known in the art.

Alternatively, a labeled nucleic acid according to the invention may be utilized as a probe in a Northern blot of a RNA extract from the patient.

Preferably, a nucleic acid extract from the patient is utilized in concert with oligonucleotide primers corresponding to sense and antisense sequences of a nucleic acid sequence according to the invention, or flanking sequences thereof, in a nucleic acid amplification reaction such as PCR, or the ligase chain reaction (LCR) as for example described in International Application WO89/09385 which is incorporated by reference herein.

A variety of automated solid-phase detection techniques are also appropriate. For example, very large scale immobilized primer arrays (VLSIPS™) are used for the detection of nucleic acids as for example described by Fodor et al., 1991, Science 251 767 and Kazal et al., 1996, Nature Medicine 2 753. The above generic techniques are well known to persons skilled in the art.

Pharmaceutical Compositions

A further feature of the invention is the use of the polypeptide, fragment, variant or derivative of the invention ("immunogenic agents") as actives in a pharmaceutical composition for protecting patients against infection by *N. meningitidis*.

Suitably, the pharmaceutical composition comprises a pharmaceutically-acceptable carrier, diluent or excipient.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for providing a patient with the composition of the invention. For example, oral, rectal, parenteral, sublingual, buccal, intravenous, intra-articular, intramuscular, intra-dermal, subcutaneous, inhalational, intraocular, intraperitoneal, intracerebroventricular, transdermal and the like may be employed.

Intra-muscular and subcutaneous injection is appropriate, for example, for administration of immunogenic compositions, vaccines and DNA vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the immunogenic agents of the invention with liquid carriers or finely divided solid carriers or both, and then, if necessary, shaping the product into the desired presentation.

The above compositions may be administered in a manner compatible with the dosage formulation, and in such amount as is immunogenically-effective to protect patients from *N. meningitidis* infection. The dose administered to a patient, in the context of the present invention, should be sufficient to effect a beneficial response in a patient over time such as a reduction in the level of *N. meningitidis*, or to inhibit infection by *N. meningitidis*. The quantity of the immunogenic agent(s) to be administered may depend on the subject to be treated inclusive of the age, sex, weight and general health condition thereof. In this regard, precise amounts of the immunogenic agent(s) required to be administered will depend on the judgement of the practitioner.

In determining the effective amount of the immunogenic agent to be administered in the treatment or prophylaxis against *N. meningitidis*, the physician may evaluate circulating plasma levels, progression of disease, and the production of anti-*N. meningitidis* antibodies. In any event, suitable dosages of the immunogenic agents of the invention may be readily determined by those of skill in the art. Such dosages may be in the order of nanograms to milligrams of the immunogenic agents of the invention.

The above compositions may be used as therapeutic or prophylactic vaccines. Accordingly, the invention extends to the production of vaccines containing as actives one or more of the immunogenic agents of the invention. A variety of applicable procedures are contemplated for producing such vaccines. Exemplary procedures include, for example, those described in NEW GENERATION VACCINES (1997, Levine et al., Marcel Dekker, Inc. New York, Basel Hong Kong) which is incorporated herein by reference.

An immunogenic agent according to the invention can be mixed, conjugated or fused with other antigens, including B or T cell epitopes of other antigens. In addition, it can be conjugated to a carrier as described below.

When an haptenic peptide of the invention is used (i.e., a peptide which reacts with cognate antibodies, but cannot itself elicit an immune response), it can be conjugated with an immunogenic carrier. Useful carriers are well known in the art and include for example: thyroglobulin; albumins such as human serum albumin; toxins, toxoids or any mutant cross-reactive material (CRM) of the toxin from tetanus, diptheria, pertussis, *Pseudomonas, E. coli, Staphylococcus*, and *Streptococcus*; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immunogenic protein may be used. For example, a haptenic peptide of the invention can be coupled to a T cell epitope of a bacterial toxin, toxoid or CRM. In this regard, reference may be made to U.S. Pat. No. 5,785,973 which is incorporated herein by reference.

In addition, a polypeptide, fragment, variant or derivative of the invention may act as a carrier protein in vaccine compositions directed against *Neisseria*, or against other bacteria or viruses.

The immunogenic agents of the invention may be administered as multivalent subunit vaccines in combination with antigens of *N. meningitidis*, or antigens of other organisms inclusive of the pathogenic bacteria *H. influenzae, M. catarrhalis, N. gonorrhoeae, E. coli, S. pneumoniae* etc. Alternatively or additionally, they may be administered in concert with oligosaccharide or polysaccharide components of *N. meningitidis*.

The vaccines can also contain a pharmaceutically-acceptable carrier, diluent or excipient as hereinbefore defined.

The vaccines and immunogenic compositions may include an adjuvant as is well known in the art. Adjuvants contemplated by the present invention include, but are not limited to: surface active substances such as hexadecylamine, octadecylamine, octadecyl amino acid esters, lysolecithin, dimethyldioctadecylammonium bromide, N,N-dicoctadecyl-N', N'bis (2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, QuilA and immune stimulating complexes (ISCOMS).

With regard to examples of adjuvants, reference is also made to International Publication WO99/36544 incorporated herein by reference.

Vaccination by DNA Delivery

Expression constructs comprising modified NhhA proteins of the invention may be administered to humans to prophylactically and/or therapeutically treat the host. In this regard, expression constructs may encode one or more modified NhhA peptides, polypeptides, fragments or derivatives of these, collectively referred to as "immunogenic agents".

Expression constructs also include gene therapy constructs, which employ specialized gene therapy vectors such as vaccinia, and viral vectors useful in gene therapy. The latter include adenovirus and adenovirus-associated viruses (AAV) such as described in Franceschi et al., 2000, J. Cell Biochem. 78:476, Braun-Falco et al., 1999, Gene Ther. 6:432, retroviral and lentiviral vectors such as described in Buchshacher et al., 2000, Blood 95:2499 and vectors derived from herpes simplex virus and cytomegalovirus. A general review of gene therapy vectors and delivery methods may be found in Robbins et al., 1998, Trends in Biotech. 16:35. An exemplary reference which describes a number of vectors potentially suitable for gene therapy using *Neisseria* proteins, and methods of delivery, is International Publication WO99/36544 incorporated herein by reference.

The immunogenic agents of the invention may be expressed by attenuated viral hosts. By "attenuated viral hosts" is meant viral vectors that are either naturally, or have been rendered, substantially avirulent. A virus may be rendered substantially avirulent by any suitable physical (e.g., heat treatment) or chemical means (e.g., formaldehyde treatment). By "substantially avirulent" is meant a virus whose infectivity has been destroyed. Ideally, the infectivity of the virus is destroyed without affecting the proteins that carry the immunogenicity of the virus. From the foregoing, it will be appreciated that attenuated viral hosts may comprise live viruses or inactivated viruses.

Attenuated viral hosts which may be useful in a vaccine according to the invention may comprise viral vectors inclusive of adenovirus, cytomegalovirus and preferably pox viruses such as vaccinia (see for example Paoletti and Panicali, U.S. Pat. No. 4,603,112 which is incorporated herein by reference) and attenuated *Salmonella* strains (see for example Stocker, U.S. Pat. No. 4,550,081 which is herein incorporated by reference). Live vaccines are particularly advantageous because they lead to a prolonged stimulus that can confer substantially long-lasting immunity. Another reference which describes a variety of viral vectors potentially suitable for immunization using *Neisseria* proteins, and methods of delivery, is International Publication WO99/36544 incorporated herein by reference.

Multivalent vaccines can be prepared from one or more microorganisms that express different epitopes of *N. meningitidis* (e.g., other surface proteins or epitopes of *N. meningitidis*). In addition, epitopes of other pathogenic microorganisms can be incorporated into the vaccine.

In a preferred embodiment, this will involve the construction of a recombinant vaccinia virus to express a nucleic acid sequence according to the invention. Upon introduction into a host, the recombinant vaccinia virus expresses the immunogenic agent, and thereby elicits a host CTL response. For example, reference may be made to U.S. Pat. No. 4,722,848, incorporated herein by reference, which describes vaccinia vectors and methods useful in immunization protocols.

A wide variety of other vectors useful for therapeutic administration or immunization with the immunogenic agents of the invention will be apparent to those skilled in the art from the present disclosure.

In a further embodiment, the nucleotide sequence may be used as a vaccine in the form of a "naked DNA" vaccine as is known in the art. For example, an expression vector of the invention may be introduced into a mammal, where it causes production of a polypeptide in vivo, against which the host mounts an immune response as for example described in Barry, M. et al., (1995, *Nature,* 377:632-635) which is hereby incorporated herein by reference.

Detection Kits

The present invention also provides kits for the detection of *N. meningitidis* in a biological sample. These will contain one or more particular agents described above depending upon the nature of the test method employed. In this regard, the kits may include one or more of a polypeptide, fragment, variant, derivative, antibody, antibody fragment or nucleic acid according to the invention. The kits may also optionally include appropriate reagents for detection of labels, positive and negative controls, washing solutions, dilution buffers and the like. For example, a nucleic acid-based detection kit may include (i) a nucleic acid according to the invention (which may be used as a positive control), (ii) an oligonucleotide primer according to the invention, and optionally a DNA polymerase, DNA ligase etc depending on the nucleic acid amplification technique employed.

Preparation of Immunoreactive Fragments

The invention also extends to a method of identifying an immunoreactive fragment of a polypeptide, variant or derivatives according to the invention. This method essentially comprises generating a fragment of the polypeptide, variant or derivative, administering the fragment to a mammal; and detecting an immune response in the mammal. Such response will include production of elements which specifically bind *N. meningitidis* and/or said polypeptide, variant or derivative, and/or a protective effect against *N. meningitidis* infection.

Prior to testing a particular fragment for immunoreactivity in the above method, a variety of predictive methods may be used to deduce whether a particular fragment can be used to obtain an antibody that cross-reacts with the native antigen. These predictive methods may be based on amino-terminal or carboxy-terminal sequence as for example described in Chapter 11.14 of Ausubel et al., supra. Alternatively, these predictive methods may be based on predictions of hydrophilicity as for example described by Kyte & Doolittle 1982, J. Mol. Biol. 157 105 and Hopp & Woods, 1983, Mol. Immunol. 20 483) which are incorporated by reference herein, or predictions of secondary structure as for example described by Choo & Fasman, 1978, Ann. Rev. Biochem. 47 251), which is incorporated herein by reference.

In addition, "epitope mapping" uses monoclonal antibodies of the invention to identify cross-reactive epitopes by first testing their ability to provide cross-protection, followed by identifying the epitope recognized by said antibodies. An exemplary method is provided in Coligan et al., CURRENT PROTOCOLS IN IMMUNOLOGY, supra.

Generally, peptide fragments consisting of 10 to 15 residues provide optimal results. Peptides as small as 6 or as large as 20 residues have worked successfully. Such peptide fragments may then be chemically coupled to a carrier molecule such as keyhole limpet hemocyanin (KLH) or bovine serum albumin (BSA) as for example described in Sections 11.14 and 11.15 of Ausubel et al., supra).

It will also be appreciated that peptides may be synthetically circularized, as for example described in Hoogerhout et al., 1995, Infect. Immun. 63 3473, which is herein incorporated by reference.

The peptides may be used to immunize an animal as for example discussed above. Antibody titers against the native or parent polypeptide from which the peptide was selected may then be determined by, for example, radioimmunoassay or ELISA as for instance described in Sections 11.16 and 114 of Ausubel et al., supra.

Antibodies may then be purified from a relevant biological fluid of the animal by ammonium sulfate fractionation or by chromatography as is well known in the art. Exemplary protocols for antibody purification are given in Sections 10.11 and 11.13 of Ausubel et al., supra, which are herein incorporated by reference.

Immunoreactivity of the antibody against the native or parent polypeptide may be determined by any relevant procedure such as, for example, Western blot.

Functional Blockers

The wild-type NhhA/HiaNm polypeptides disclosed in WO99/31132 are believed to have adhesin properties. They in fact have some similarity to adhesins of *Haemophilus influenzae* which are surface antigens. Specifically they are approximately 67% homologous to the Hia protein of *H. influenzae* (Barenkamp & St. Geme III, 1996, Molecular Microbiology 19 1215), and 74% homologous to the Hsf protein of *H. influenzae* (St. Geme III, J. et al, 1996, Journal of Bacteriology 178 6281; and U.S. Pat. No. 5,646,259). For these comparisons, a gap weight of 3, and length weight of 0.01 was used using the GAP program (Deveraux, 1984, supra). Thus, interruption of the function of these polypeptides would be of significant therapeutic benefit since they would prevent *N. meningitidis* bacteria from adhering to and invading cells. Interruption of the function may be effected in several ways.

For example, moieties such as chemical reagents or polypeptides which block receptors on the cell surface which interact with a polypeptides of the invention may be administered. These compete with the infective organism for receptor sites. Such moieties may comprise for example polypeptides of the invention, in particular fragments, or functional equivalents of these as well as mimetics.

The term "mimetics" is used herein to refer to chemicals that are designed to resemble particular functional regions of the proteins or peptides. Anti-idiotypic antibodies raised against the above-described antibodies which block the binding of the bacteria to a cell surface may also be used. Alternatively, moieties which interact with the receptor binding sites in the polypeptides of the invention may effectively prevent infection of a cell by *N. meningitidis*. Such moieties may comprise blocking antibodies, peptides or other chemical reagents.

All such moieties, pharmaceutical compositions in which they are combined with pharmaceutically acceptable carriers and methods of treating patients suffering from *N. meningitidis* infection by administration of such moieties or compositions form a further aspect of the invention.

The polypeptides of the invention may be used in the screening of compounds for their use in the above methods. For example, polypeptides of the invention may be combined with a label and exposed to a cell culture in the presence of a reagent under test. The ability of reagent to inhibit the binding of the labeled polypeptide to the cell surface can then be observed. In such a screen, the labeled polypeptides may be used directly on an organism such as *E. coli*. Alternatively, *N. meningitidis* itself may be engineered to express a modified and detectable form of the polypeptide. The use of engineered *N. meningitidis* strains in this method is preferred as it is more likely that the tertiary structure of the protein will resemble more closely that expressed in wild-type bacteria.

In order that the invention may be readily understood and put into practical effect, particular preferred embodiments will now be described by way of the following non-limiting examples.

EXAMPLE 1

Identification of Constant and Variable Regions of NhhA Polypeptides

The present inventors have elucidated NhhA amino acid sequences which are conserved and/or non-conserved between ten (10) strains of *N. meningitidis*. The non-conserved regions are subdivided into four variable regions (V1, V2, V3 and V4) and the conserved regions are subdivided into C1, C2, C3, C4 and C5 (as shown in FIG. 1 and Table 1; SEQ ID NOS:1-11). The corresponding nucleotide sequence comparison is shown in FIG. 2 (SEQ ID NOS:12-22).

EXAMPLE 2

PMC 21 NhhA Polypeptide Over-Expression

The NhhA protein encoded by the nhhA gene of *N. meningitidis* strain PMC21 was over expressed by making an expression construct wherein the nhhA gene is operably linked to a promoter.

The following oligonucleotide primers were used to amplify an N. meningitidis PMC21 strain nhhA nucleic acid open reading frame by PCR:—

```
                                            (SEQ ID NO 40)
HOMP5':  5'-CAA TTA ACG GCC GAA TAA AAG GAA GCC
         GAT ATG AAC AAA ATA TAC CGC ATC-3';
         which contains an EagI restriction site
         (underlined) and the sequence encoding the
         first 7 (seven) amino acids of NhhA (bold
         type)

(SEQ ID NO 41)
HOMP3'AN 5'-TGG AAT CCA TGG AAT CGC CAC CCT TCC
         CTT C-3';
         which contains an NcoI restriction site
         (underlined) and the reverse complement
         of sequence 48-61 nucleotides past the end
         of the nhhA open reading frame of strain
         ¢3 (bold type)
```

The amplification product contained restriction sites which were subsequently digested with EagI and NcoI restriction endonucleases.

The plasmid used for subcloning was pCO14K, which plasmid contains a porA promoter upstream of the gene encoding the strongly expressed Class 1 outer membrane protein of N. meningitidis together with flanking sequence of N. meningitidis strain 2996 and a selectable kanamycin resistance gene as described by Rouppe van der Voort, et al., Infect Immun 1996 64:2745.

The digested amplification product was then ligated into EagI and NcoI restriction endonuclease-digested pCO14K. This ligation resulted in the replacement of the majority of the porA open reading frame with the nhhA amplification product (FIG. 3). This created a recombinant nucleic acid expression construct (open reading frame shown in SEQ ID NO:12) which encodes a polypeptide of 591 amino acids as shown in SEQ ID NO:1.

This places expression of the nhhA nucleic acid of the invention under the control of the strong porA promoter. Translation begins at the ATG codon beginning at position 31 of HOMP5'. In order to prevent formation of a fusion between the porA and nhhA, the HOMP5' sequence contains a TAA stop codon prior to the initiating ATG described above.

The resulting plasmid, pIP52(PMC21), was linearized by restriction digestion and used to transform N. meningitidis strain 7G2 using the method described by Janik et al, 1976, Journal of Clinical Microbiology 4 71. Transformants were selected by overnight incubation at 37° C. in 5% $CO_2$ on solid media containing 100 μg/ml kanamycin. Kanamycin resistant colonies were selected, subcultured overnight and screened for over-expression of NhhA polypeptide by separating total cell proteins electrophoretically on 10% SDS-PAGE followed by transfer to nitrocellulose membrane using a Semi-Dry Blotter (BioRad). The membrane was then incubated sequentially with rabbit anti-NhhA sera (as described in International Publication WO99/31132) and alkaline-phosphatase conjugated anti-Rabbit IgG (Sigma) before colorimetric detection with NBT/BCIP (Sigma). One clone was isolated which expressed NhhA polypeptide at a higher level compared with the parental strain (FIG. 11). Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14A; SEQ ID NO:33).

The plasmid construct pIP52(PMC21) may be transformed into any transformation-competent strain of N. meningitidis.

EXAMPLE 3

H41 NhhA Polypeptide Over-Expression

The NhhA protein encoded by the nhhA gene of N. meningitidis strain H41 was over expressed using the same methods as described in Example 2. This created a recombinant nucleic acid expression construct (open reading frame shown in SEQ ID NO:13) which encodes a polypeptide of 591 amino acids as shown in SEQ ID NO:2. In this example the resulting plasmid pIP52(H41) was linearized, and transformed into N. meningitidis strain 7G2. Kanamycin resistant colonies were analysed and one was chosen which when examined by Western immunoblot, demonstrated overexpression of NhhA. (FIG. 11). Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14B; SEQ ID NO:34).

This strategy may be employed to create expression constructs containing the wild-type nhhA sequence of other N. meningitidis strains.

EXAMPLE 4

NhhA Deletion Mutant Construction Using Convenient Restriction Site

For ease of reference, the amino acid sequence of the NhhA polypeptide encoded by the nhhA nucleic acid of strain PMC21 is shown in SEQ ID NO 1. The present inventors created a deletion mutant version of wild-type PMC21 nhhA, in which the most variable region between strains was deleted. An amplification product encoding amino acids 1-54 of the wild-type PMC21 NhhA polypeptide was generated by PCR amplification from nhhA nucleic acid template using the following primers:

```
                                            (SEQ ID NO 40)
HOMP5':  5'-CAA TTA ACG GCC GAA TAA AAG GAA GCC
         GAT ATG AAC AAA ATA TAC CGC ATC-3';
         which is the same oligonucleotide used to
         create the overexpression construct pIP52.

(SEQ ID NO 42)
NH3'BG:  5'-GGT CAG ATC TGT TTC ATT GTT AGC ACT
         TGC-3';
         which contains a BglII restriction site
         (underlined) and the reverse complement
         of sequence encoding amino acids 134,
         (double underlined) and 49-54 of wild-type
         PMC21 NhhA (bold type).
```

The resulting amplification product included an EagI and BglII restriction endonuclease sites. pIP52(PMC21) includes a single EagI site 20 bp upstream of the start of the nhhA open reading frame (ORF) and a single BglII site located within the ORF (see FIG. 3B). Therefore, pIP52(PMC21) and the amplification product were subjected to restriction endonuclease digestion with EagI and BglII, ligated and used to transform competent DH5a strain E. coli bacteria; this replaces the EagI/BglII fragment of pIP52(PMC21) with the PCR product. This created a recombinant nucleic acid expression construct (open reading frame shown in FIG 5B; SEQ ID NO:28) which encodes a polypeptide of 512 amino acids as shown in FIG 5A (SEQ ID NO:23). This amino acid sequence includes amino acids 1-54 and 134-592 of the wild-type sequence, and thereby deletes the majority of the V1 region, all of the V2 and C2 regions, and part of the C3 region of the wild-type PMC21 NhhA polypeptide.

This plasmid was linearised by restriction digestion and transformed in to *N. meningitidis* strain 7G2. Using methods as described in Example 1, one clone was isolated which overexpresses the truncated PMC21 NhhA (FIG. 11).

Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14C; SEQ ID NO:35). To confirm the presence of a cleavable signal sequence and to confirm the identity of the over expressed protein, outer membrane proteins were semi-purified by isolating the fraction that is insoluble in the detergent sarkosyl.

The isolated membrane proteins were separated electrophoretically before transfer to Nylon membrane. The position of the over expressed protein was revealed by Coomassie stain. This region of the membrane was excised and the protein was N-terminal sequenced. The first eleven amino acids of this protein were XXETDLTSVGT (SEQ ID NO:52) which corresponds to amino acid residues 52 to 62 (inclusive) of the amino acid sequence predicted to be expressed by the over expression construct as defined in this example.

This is an example of a deletion using existing restriction sites within the polynucleotide sequence. This construct may be transformed into any transformation competent *N. meningitidis*.

EXAMPLE 5

NhhA Deletion Mutant Construction Using Convenient Restriction Site

An expression construct containing the wild-type nhhA sequence of H41 was made as described in Example 2. The resulting expression construct was named pIP52(H41). A deletion mutant was made, using the strategy outlined in this example. In this instance the oligonucleotide primers used were:

```
                                         (SEQ ID NO: 40)
HOMP5': 5'-CAA TTA ACG GCC GAA TAA AAG GAA GCC
        GAT ATG AAC AAA ATA TAC CGC ATC-3';
        which is the same oligonucleotide used to
        create the overexpression construct pIP52

(SEQ ID NO 43)
NH3'STU: 5'-GAT CAG GCC TGT ATC TTC ATC GGT AGC
         ATT-3';
         which contains a StuI restriction site
         (underlined) and the reverse complement
         of sequence encoding amino acids 134,
         (double underlined) and 49-54 of wild-type
         H41 NhhA (bold type).
```

The resulting amplification product contains single EagI and StuI restriction endonuclease sites. The expression construct pIP52(H41) contains these restriction sites. Therefore, pIP52(H41) and the amplification product were subjected to restriction endonuclease digestion with EagI and StuI, ligated and used to transform competent DH5α strain *E. coli* bacteria; this ligation replaces the EagI/StuI fragment of pIP52 (H41) with the PCR product. This created a recombinant nucleic acid expression construct (open reading frame shown in FIG. 6B and SEQ ID NO:29) which encodes a polypeptide of 513 amino acids as shown in FIG. 6A and SEQ ID NO:24. This amino acid sequence includes amino acids 1-54 and 134-593 of the wild-type sequence, and thereby deletes the majority of the V1 region, all of the V2 and C2 regions, and part of the C3 region of the wild-type H41 NhhA polypeptide.

This plasmid was linearised by restriction digestion and transformed in to *N. meningitidis* strain 7G2. Using methods as described in Example 1, one clone was isolated which overexpresses the truncated H41 NhhA (FIG. 11).

Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14D; SEQ ID NO:36).

In this example, a construct was made containing the C1 and C5 regions, and all other regions deleted (see FIG. 5A).

The following oligonucleotide primers were used in PCR reactions to amplify DNA corresponding to region C1 (see FIG. 1) from chromosomal DNA of strain PMC21:

```
                                      (SEQ ID NO: 40)
HOMP5': 5'-CAA TTA ACG GCC GAA TAA AAG GAA GCC
        GAT ATG AAC AAA ATA TAC CGC ATC-3';
        which is the same oligonucleotide used to
        create the over-expression construct
        pIP52(PMC21)

(SEQ ID NO 44)
SO-C:   5'-GAC GAA ATC AAC GTT CTT AGC ACT TGC
        CTG AAC CGT TGC-3';
        which sequence is the reverse complement
        of sequence encoding amino acids 237-241
        at the start of the C5 region (underlined)
        and amino acids 45-52 at the end of the
        C1 region (bold type) of wild-type NhhA of
        strain PMC21.
```

The amplification product of this reaction is HOMP5'/SO-C.

The following oligonucleotide primers were used in PCR reactions to amplify C5 from chromosomal DNA of strain PMC21:

```
                                      (SEQ ID NO 45)
SO-D:   5'-AAC GTT GAT TTC GTC CGC ACT TAC-3';
        which encodes amino acids 237-244 at the
        start of C5 (underlined indicates reverse
        complement of Primer SO-C), (SEQ ID NO 41)
HO3'AN: 5'-TGG AAT CCA TGG AAT CGC CAC CCT TCC
        CTT C-3';
        which is the same primer used in the
        construction of pIP52.
```

The amplification product of this reaction is SO-D/HO3'AN.

The amplification products HOMP5'/SO-C and SO-D/HO3'AN were purified from an agarose gel following separation by electrophoresis, were mixed, and subjected to further amplification using primers HOMP5' and HO3'AN. The resulting amplification product encodes amino acids 1-52 and 337-591 of wild-type NhhA of PMC21. This amplification product was subjected to restriction digestion with EagI and NcoI, and cloned into pCO14K, as described in Example 1. This recombinant molecule contains regions C1 and C5, thus deleting regions V1 to 4 and C2 to 4. The nucleotide sequence of the open reading frame is shown in FIG. 7B and SEQ ID NO:30, and the predicted polypeptide sequence derived from this nucleotide sequence is shown in FIG. 7A and SEQ ID NO:25.

This plasmid was linearized by restriction digestion and transformed in to *N. meningitidis* strain 7G2. Using methods as described in Example 2, one clone was isolated which overexpresses the truncated PMC21 NhhA.

Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14E; SEQ ID NO:37).

This plasmid may be transformed into any transformation competent strain of *N. meningitidis*.

EXAMPLE 7

NhhA Deletion Mutant Construction Using Splice-Overlap PCR

It will be appreciated that a similar strategy can be used to create recombinant polynucleotides encoding various regions of NhhA. A construct can be made comprising regions C1, C4, V4 and C5 using the following strategy (see FIG. 5B):

The C1 region is amplified using oligonucleotide primers:

```
                                       (SEQ ID NO: 40)
HOMP5': 5'-CAA TTA ACG GCC GAA TAA AAG GAA GCC
        GAT ATG AAC AAA ATA TAC CGC ATC-3';

(SEQ ID NO: 46)
SO-E:   5'-AAC GCT TGC CGC ACG CTT AGC ACT TGC
        CTG CAA CGT TGC-3';
        which encodes the reverse complement of
        amino acids 211-215 at the start of the C4
        region (underlined) and at the end of the
        C1 region (bold type) of strain PMC21.
```

The amplification product of this reaction is HOMP5'/SO-E.

The following oligonucleotide primers are used in PCR reactions to amplify the region C4-V4-C5 from chromosomal DNA of strain PMC21:

```
                                       (SEQ ID NO: 47)
SO-F:   5'-CGT GCG GCA AGC GTT AAA GAC GTA-3';
        which encodes amino acids 211-218 at the
        start of C4 (underlined indicates reverse
        complement of Primer SO-E), (SEQ ID NO: 41)
HO3'AN: 5'-TGG AAT CCA TGG AAT CGC CAC CCT TCC
        CTT C-3'.
```

The amplification product of this reaction is SO-F/HOMP3'.

The amplification products HOMP5'/SO-E and SO-F/HO3'AN will be purified from agarose gel following separation by electrophoresis, and will be mixed, and subjected to further amplification using primers HOMP5' and HO3'AN. The resulting product encodes amino acids 1-52 and 211-591 of wild-type NhhA of PMC21. This amplification product will be subjected to restriction digestion with EagI and NcoI, and cloned into pCO14K. This recombinant molecule contains regions C1, C4, V4 and C5 thus deleting regions V1-3 and C2-3. The nucleotide sequence of the open reading frame is shown in FIG. 8B and SEQ ID NO:31, and the predicted polypeptide sequence derived from this nucleotide sequence is shown in FIG. 8A and SEQ ID NO:26. Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14F; SEQ ID NO:38).

EXAMPLE 8

NhhA Deletion Mutant Construction Using Splice-Overlap PCR

It will be appreciated that a similar strategy can be used to create recombinant polynucleotides encoding various regions of NhhA. A construct can be made comprising regions C1, C2, C3, C4, and C5 using the following strategy (see FIG. 5C):

C1 and C2 will be amplified using oligonucleotide primers:

```
                                       (SEQ ID NO: 40)
HOMP5': 5'-CAA TTA ACG GCC GAA TAA AAG GAA GCC
        GAT ATG AAC AAA ATA TAC CGC ATC-3';

(SEQ ID NO: 48)
SO-G:   5'-CAG CGA GTA GGT GAA TTG TTT GAT TTT
        CAG GTT GTC GCC GGC TTT GAG GGT GTT
        AGC ACT TGC CTG AAC CGT-3';
        which encodes the reverse complement of
        amino acids 125-129 at the start of the C3
        region (underlined), all of the C2 region
        (amino acids 109-120, bold and double
        underlined) and the end of the C1 region
        (amino acids 46-52, bold type) of strain
        PMC21.
```

The amplification product of this reaction is HOMP5'/SO-G.

The C3 and part of C4 regions will be amplified using the following oligonucleotide primers:

```
                                       (SEQ ID NO 49)
SO-H:   5'-TTC ACC TAC TCG CTG AAA AAA GAC-3';
        which encodes amino acids 125-132 at the
        start of C3 (underlined indicates reverse
        complement of Primer SO-G)

(SEQ ID NO: 50)
SO-I:   5'-GCC AGC GTT TAA TAC GTC TTT AAC GCT
        TGC CGC ACG ATC GGT CAA AGT CGA ACC AAT-3';
        which encodes the reverse complement of
        amino acids 182-88 at the end of C3 (under-
        lined) and amino acids 211-222 of C4 (bold
        type).
```

The amplification product of this reaction is SO-H/SO-I.

The amplification products HOMP5'/SO-G and SO-H/SO-I are purified from agarose gel following separation by electrophoresis, mixed and subjected to further amplification using primers HOMP5' and SO-I to yield a product encoding amino acids 1-52, 103-114, 125-188, and 211-222, i.e. regions C1, C2, C3 and part of C4. The amplification product of this reaction is HOMP5'/SO-I.

The C5 and part of C4 regions are amplified using the following oligonucleotide primers:

```
                                       (SEQ ID NO: 51)
SO-J:   5' GTA TTA AAC GCT GGC TGG AAC ATT AAA
        GGC GTT AAA AAC GTT GAT TTC GTC CGC
        ACT-3';
        which encodes amino acids 218-229 of C4
        (underlined), and amino acids 237-243 of
        C5 (bold type) of wild-type NhhA of strain
        PMC21. (Bold underlined type indicates re-
        verse complement of SO-I)

(SEQ ID NO: 41)
HO3'AN: 5'-TGG AAT CCA TGG AAT CGC CAC CCT TCC
        CTT C-3'.
```

The amplification product of this reaction is SO-J/HO3'AN.

The amplification products HOMP5'/SO-I and SO-J/HO3'AN will be purified from agarose gel following separation by electrophoresis, and will be mixed, and subjected to further amplification using primers HOMP5' and HO3'AN. The resulting product encodes amino acids 1-52, 103-114, 125-188, 211-229, and 237-591 of wild-type NhhA of strain PMC21. The resulting product will be subjected to restriction digestion with EagI and NcoI, and cloned into pCO14K. This recombinant molecule contains regions C1, C2, C3, C4 and C5, thus deleting regions V1, V2, V3, and V4. The nucleotide sequence of the open reading frame is shown in FIG. 9B and SEQ ID NO:32, and the predicted polypeptide sequence derived from this nucleotide sequence is shown in FIG. 9A and SEQ ID NO: 27. Analysis of the predicted amino acid sequence using the computer program SIGCLEAVE (part of the eGCG suite of available from the Australian National Genomic Information Service {ANGIS}) indicates that the first 51 amino acids will be cleaved to produce the mature polypeptide (FIG. 14G; SEQ ID NO:39).

This construct can be transformed into any transformation competent strain of *N. meningitidis*.

EXAMPLE 9

Purification of Over Expressed NhhA Polypeptides

Recombinant NhhA polypeptide as described in the previous Examples may be isolated by the following procedure. Bacteria are grown overnight (12-14 hours) at 37° C. in an atmosphere of 5% $CO_2$. (In this example, media was BHI agar supplemented with Leventhal's base. Other growth media are well known to those skilled in the art). Bacteria from ten 25 mL agar plates were collected and suspended in 25 mL 10 mM Tris adjusted to ph 8.0 with HCl. An equal volume of 10 mM Tris (pH 8.0) containing 2% sarkosyl was added and the mixture mixed gently for 1 hour at 4° C. This was centrifuged at 100,000×g for seventy minutes at 20° C. and the supernatant discarded. The pellet was resuspended in 25 mL 10 mM Tris (PH 8.0) containing 1% sarkosyl by passing through a 25 gauge needle. This was centrifuged at 100,000×g for seventy minutes at 20° C. and the supernatant discarded. The pellet was resuspended in 10 mL 10 mM Tris (pH 8.0) by passing through a 25 gauge needle. This fraction contains the sarkosyl insoluble components of the cell, and is enriched for outer membrane proteins. (An additional step may be incorporated to remove residual sarkosyl detergent, whereby the protein solution is dialysed for four cycles of 4-8 hours against 100-1000 volumes of, for example, 10 mM Tris.Cl pH 8.0 or PBS (phosphate buffered saline) at 4° C.

Having determined the concentration of protein in the suspension by absorbance at wavelength of 280 nm, or by using a BCA kit (Pierce), approximately 1 mL of solution containing 10 mg of protein in a solution containing 1% SDS (sodium lauryl sulphate), 2% β-mercaptoethanol was separated on 1.5 mm thick 6% SDS-PAGE in the BioRad mini-protean II apparatus. The high molecular weight NhhA was eluted from the gel using the BioRad "mini Whole gel Eluter". Approximately 10% of each eluted fraction was checked by SDS-PAGE separation followed by Coomassie staining. Fractions containing NhhA essentially free of other proteins were pooled. This procedure was carried out to isolate over expressed mature NhhA as described in Example 2 (SEQ ID NO:1), over expressed BglII deletion mature NhhA as described in Example 4 (SEQ ID NO:23) and over expressed NhhA deletion mutant as described in Example 6 (SEQ ID NO:25). Isolated protein is shown in FIG. 12.

EXAMPLE 10

Immunogenicity of Purified NhhA Deletion Mutant Polypeptides

Mice were inoculated with purified wild-type NhhA polypeptides and deletion mutants as described in the previous Examples. In one group, each Balb/C mouse was inoculated subcutaneously with approximately 130 μg PMC21 NhhA with MPL+TDM™ adjuvant (obtained from Sigma-Aldrich) on day 0, 115 μg on day 14. In a second group, each mouse was inoculated with approximately 120 μg protein with MPL+TDM™ adjuvant (obtained from Sigma-Aldrich) at day 0 and 190 μg at day 14. In a third group, each mouse was inoculated with approximately 260 μg protein with MPL+TDM™ adjuvant (obtained from Sigma-Aldrich) at day 0 and 1240 μg at day 14. Blood samples were taken at day 21 and serum was extracted. These sera were tested for the presence of antibodies recognising full length PMC 21 NhhA by Western immunoblot (FIG. 13). OMC preparations (5 mg) of P6 (overexpresses PMC21 NhhA) and Strain 2A (NhhA expression abolished) were separated by 6% SDS-PAGE using the BioRad Mini Protean II electrophoresis apparatus. The proteins were transferred to nitrocellulose electrophoretically, and the filter was cut into 3 mm strips then blocked in 5% skim milk in PBS. Mouse sera was diluted to 1:1000 and 1:10000 in 5% skim milk powder and incubated with the nitrocellulose strips. Antibody binding was detected using alkaline-phosphatase conjugated anti-mouse IgG (Sigma) before colorimetric detection with NBT/BCIP (Sigma). As can be seen from FIG. 13, it is possible to elicit an immune response against the full length mature PMC21 NhhA polypeptide by inoculation with NhhA deletion mutants or with full length mature NhhA polypeptides.

EXAMPLE 11

Expression of Deletion Mutant Polypeptide in *E. coli*

In addition to expression of the mutant polypeptides of the invention in *N. meningitidis*, they may also be expressed in *E. coli* bacteria. Any of the recombinant nhhA deletion mutants of Examples 4-8 may be used as template for PCR amplification. Oligonucleotide primers used may be as described in International Publication WO99/31132 (such as SEQ ID NO 24 and SEQ ID NO 25 of that document). The amplification product may be restriction digested with BamHI/HindIII enzymes and ligated with BamHI/HindIII restriction digested plasmid pMALC2 (New England BioLabs), and the resultant plasmid transformed into competent *E. coli* strain DH5α. The resulting strain can be induced to express high levels of recombinant protein using conditions recommended by the manufacturer of pMALC2. The resulting recombinant protein is a fusion of maltose binding protein and the deletion mutant NhhA polypeptide of the invention. This may be semi-purified by separation on SDS-PAGE followed by electroelution using the Mini-Gel Electro-eluter (BioRad) according to manufacturers instructions. The semi-purified fusion protein may then be dialysed against PBS, before digestion with the protease enzyme Factor Xa. to cleave the maltose binding protein moiety from the recombinant NhhA protein. The recombinant NhhA protein may be purified by standard methods, as for example described by R. K. Scopes, Protein Purification (Springer-Verlag, New York, N.Y. USA, 1993).

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

TABLE 1

| | C1 | V1 | C2 | V2 | C3 | V3 | C4 | V4 | C5 |
|---|---|---|---|---|---|---|---|---|---|
| Consensus SEQ ID NO: 11 | 1-50 | 51-108 | 109-120 | 121-134 | 135-198 | 199-220 | 221-239 | 240-248 | 249-604 |
| PMC21 SEQ ID NO: 1 | 1-50 | 51-108 | 109-120 | 121-124 | 125-188 | 189-210 | 211-229 | 230-236 | 237-591 |
| H41 SEQ ID NO: 2 | 1-50 | 51-102 | 103-114 | 115-124 | 125-188 | 189-210 | 211-229 | 230-236 | 237-591 |
| P20 SEQ ID NO: 3 | 1-50 | 51-105 | 106-117 | 118-121 | 122-185 | 186-205 | 206-224 | 225-234 | 235-589 |
| EG327 SEQ ID NO: 4 | 1-50 | 51-104 | 105-116 | 117-126 | 127-190 | 191-212 | 213-231 | 232-238 | 239-594 |
| EG329 SEQ ID NO: 5 | 1-50 | 51-108 | 109-120 | 121-124 | 125-188 | 189-210 | 211-229 | 230-236 | 237-591 |
| H38 SEQ ID NO: 6 | 1-50 | 51-105 | 106-117 | 118-131 | 132-195 | 196-217 | 218-236 | 237-243 | 244-599 |
| H15 SEQ ID NO: 7 | 1-50 | 51-104 | 105-116 | 117-130 | 131-194 | 195-216 | 217-235 | 236-242 | 243-598 |
| BZ10 SEQ ID NO: 8 | 1-50 | 51-104 | 105-116 | 117-130 | 131-194 | 195-216 | 217-235 | 236-242 | 243-598 |
| BZ198 SEQ ID NO: 9 | 1-50 | 51-104 | 105-116 | 117-126 | 127-190 | 191-212 | 213-231 | 232-238 | 239-594 |
| Z2491 SEQ ID NO: 10 | 1-50 | 51-102 | 103-114 | 115-124 | 125-188 | 189-208 | 209-227 | 228-236 | 237-592 |

TABLE 2

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

We claim:

1. An isolated protein comprising:
   (A) one or more conserved regions of an NhhA polypeptide which one or more conserved regions respectively consist of any of the following amino acid sequences selected from the group consisting of:
   (i) residues 1 to 50 of SEQ ID NO:11;
   (ii) residues 109 to120 of SEQ ID NO:11;
   (iii) residues 135 to198 of SEQ ID NO:11;
   (iv) residues 221 to 239 of SEQ ID NO:11; and
   (v) residues 249 to 604 of SEQ ID NO:11; and
   (B) one or more variable regions of an NhhA polypeptide, the one or more variable regions respectively consisting of any of the following amino acid sequences selected from the group consisting of:
   (a) residues 121 to134 of SEQ ID NO:11;
   (b) residues 199 to 220 of SEQ ID NO:11; and
   (c) residues 240 to 248 of SEQ ID NO:11;
   wherein a variable region of residues 51-108 of SEQ ID NO:11 or a fragment consisting of at least six amino acids thereof is absent;
   wherein the isolated protein is capable of eliciting an immune response against a plurality of strains of *Neisseria meningitidis*.

2. An isolated protein consisting of two or more contiguous conserved regions of an NhhA polypeptide, the two or more conserved regions respectively consisting of-an any of the following amino acid sequences selected from the group consisting of:
   (i) residues 1 to 50 of SEQ ID NO:11;
   (ii) residues 109 to120 of SEQ ID NO:11;
   (iii) residues 135 to198 of SEQ ID NO:11;
   (iv) residues 221 to 239 of SEQ ID NO:11; and
   (v) residues 249 to 604 of SEQ ID NO:11;
   wherein the isolated protein is capable of eliciting an immune response against a plurality of strains of *Neisseria meningitidis*.

3. The isolated protein of claim 1, wherein the protein is a deletion mutant of the NhhA polypeptide.

4. The isolated protein of claim 2, wherein the protein is a deletion mutant of the NhhA polypeptide.

5. The isolated protein of claim 1, wherein the conserved region amino acid sequence is selected from the group consisting of:
   (I) residues 1 to 50 of SEQ ID NO:1;
   (II) residues 1 to 50 of SEQ ID NO:2;
   (III) residues 1 to 50 of SEQ ID NO:3;
   (IV) residues 1 to 50 of SEQ ID NO:4;
   (V) residues 1 to 50 of SEQ ID NO:5;
   (VI) residues 1 to 50 of SEQ ID NO:6;
   (VII) residues 1 to 50 of SEQ ID NO:7;
   (VIII) residues 1 to 50 of SEQ ID NO:8;
   (IX) residues 1 to 50 of SEQ ID NO:9;
   (X) residues 1 to 50 of SEQ ID NO:10;
   (XI) residues 109 to 120 of SEQ ID NO:1;
   (XII) residues 103 to 114 of SEQ ID NO:2;
   (XIII) residues 106 to 117 of SEQ ID NO:3;
   (XIV) residues 105 to 116 of SEQ ID NO:4;
   (XV) residues 109 to 120 of SEQ ID NO:5;
   (XVI) residues 106 to 117 of SEQ ID NO:6;
   (XVII) residues 105 to 116 of SEQ ID NO:7;
   (XVIII) residues 105 to 116 of SEQ ID NO:8;
   (XIX) residues 105 to 116 of SEQ ID NO:9;
   (XX) residues 103 to 114 of SEQ ID NO:10;
   (XXI) residues 125 to 188 of SEQ ID NO:1;
   (XXII) residues 125 to 188 of SEQ ID NO:2;
   (XXIII) residues 122 to 185 of SEQ ID NO:3;
   (XXIV) residues 127 to 190 of SEQ ID NO:4;
   (XXV) residues 125 to 188 of SEQ ID NO:5;
   (XXVI) residues 132 to 195 of SEQ ID NO:6;
   (XXVII) residues 131 to 194 of SEQ ID NO:7;
   (XXVIII) residues 131 to 194 of SEQ ID NO:8;
   (XXIX) residues 127 to 190 of SEQ ID NO:9;
   (XXX) residues 125 to 188 of SEQ ID NO:10;
   (XXXI) residues 211 to 229 of SEQ ID NO:1;
   (XXXII) residues 211 to 229 of SEQ ID NO:2;
   (XXXIII) residues 206 to 224 of SEQ ID NO:3;
   (XXXIV) residues 213 to 231 of SEQ ID NO:4;
   (XXXV) residues 211 to 229 of SEQ ID NO:5;
   (XXXVI) residues 218 to 236 of SEQ ID NO:6;
   (XXXVII) residues 217 to 235 of SEQ ID NO:7;
   (XXXVIII) residues 217 to 235 of SEQ ID NO:8;
   (XXXIX) residues 213 to 231 of SEQ ID NO:9;
   (XL) residues 209 to 227 of SEQ ID NO:10;
   (XLI) residues 237 to 591 of SEQ ID NO:1;
   (XLII) residues 237 to 592 of SEQ ID NO:2;
   (XLIII) residues 235 to 589 of SEQ ID NO:3;
   (XLIV) residues 239 to 594 of SEQ ID NO:4;
   (XLV) residues 237 to 591 of SEQ ID NO:5;
   (XLVI) residues 244 to 599 of SEQ ID NO:6;
   (XLVII) residues 243 to 598 of SEQ ID NO:7;
   (XLVIII) residues 243 to 598 of SEQ ID NO:8.

(XLIX) residues 239 to 594 of SEQ ID NO:9; and
(L) residues 237 to 592 of SEQ ID NO:10.

6. The isolated protein of claim 2, wherein the conserved region amino acid sequence is selected from the group consisting of:
(I) residues 1 to 50 of SEQ ID NO:1;
(II) residues 1 to 50 of SEQ ID NO:2;
(III) residues 1 to 50 of SEQ ID NO:3;
(IV) residues 1 to 50 of SEQ ID NO:4;
(V) residues 1 to 50 of SEQ ID NO:5;
(VI) residues 1 to 50 of SEQ ID NO:6;
(VII) residues 1 to 50 of SEQ ID NO:7;
(VIII) residues 1 to 50 of SEQ ID NO:8;
(IX) residues 1 to 50 of SEQ ID NO:9;
(X) residues 1 to 50 of SEQ ID NO:10;
(XI) residues 109 to 120 of SEQ ID NO:1;
(XII) residues 103 to 114 of SEQ ID NO:2;
(XIII) residues 106 to 117 of SEQ ID NO:3;
(XIV) residues 105 to 116 of SEQ ID NO:4;
(XV) residues 109 to 120 of SEQ ID NO:5;
(XVI) residues 106 to 117 of SEQ ID NO:6;
(XVII) residues 105 to 116 of SEQ ID NO:7;
(XVIII) residues 105 to 116 of SEQ ID NO:8;
(XIX) residues 105 to 116 of SEQ ID NO:9;
(XX) residues 103 to 114 of SEQ ID NO:10;
(XXI) residues 125 to 188 of SEQ ID NO:1;
(XXII) residues 125 to 188 of SEQ ID NO:2;
(XXII) residues 122 to 185 of SEQ ID NO:3;
(XXIV) residues 127 to 190 of SEQ ID NO:4;
(XXV) residues 125 to 188 of SEQ ID NO:5;
(XXVI) residues 132 to 195 of SEQ ID NO:6;
(XXVII) residues 131 to 194 of SEQ ID NO:7;
(XXVIII) residues 131 to 194 of SEQ ID NO:8;
(XXIX) residues 127 to 190 of SEQ ID NO:9;
(XXX) residues 125 to 188 of SEQ ID NO:10;
(XXXI) residues 211 to 229 of SEQ ID NO:1;
(XXXII) residues 211 to 229 of SEQ ID NO:2;
(XXXIII) residues 206 to 224 of SEQ ID NO:3;
(XXXIV) residues 213 to 231 of SEQ ID NO:4;
(XXXV) residues 211 to 229 of SEQ ID NO:5;
(XXXVI) residues 218 to 236 of SEQ ID NO:6;
(XXXVII) residues 217 to 235 of SEQ ID NO:7;
(XXXVIII) residues 217 to 235 of SEQ ID NO:8;
(XXXIX) residues 213 to 231 of SEQ ID NO:9;
(XL) residues 209 to 227 of SEQ ID NO:10;
(XLI) residues 237 to 591 of SEQ ID NO:1;
(XLII) residues 237 to 592 of SEQ ID NO:2;
(XLIII) residues 235 to 589 of SEQ ID NO:3;
(XLIV) residues 239 to 594 of SEQ ID NO:4;
(XLV) residues 237 to 591 of SEQ ID NO:5;
(XLVI) residues 244 to 599 of SEQ ID NO:6;
(XLVII) residues 243 to 598 of SEQ ID NO:7;
(XLVIII) residues 243 to 598 of SEQ ID NO:8.
(XLIX) residues 239 to 594 of SEQ ID NO:9; and
(L) residues 237 to 592 of SEQ ID NO:10.

7. The isolated protein of claim 1, wherein the variable region amino acid sequence is selected from the group consisting of:
(AA) residues 121 to 124 of SEQ ID NO:1;
(AB) residues 115 to 124 of SEQ ID NO:2;
(AC) residues 118 to 121 of SEQ ID NO:3;
(AD) residues 117 to 126 of SEQ ID NO:4;
(AE) residues 121 to 124 of SEQ ID NO:5;
(AF) residues 118 to 131 of SEQ ID NO:6;
(AG) residues 117 to 130 of SEQ ID NO:7;
(AH) residues 117 to 130 of SEQ ID NO:8;
(AI) residues 117 to 126 of SEQ ID NO:9;
(AJ) residues 115 to 124 of SEQ ID NO:10;
(BA) residues 189 to 210 of SEQ ID NO:1;
(BB) residues 189 to 210 of SEQ ID NO:2;
(BC) residues 186 to 205 of SEQ ID NO:3;
(BD) residues 191 to 212 of SEQ ID NO:4;
(BE) residues 189 to 210 of SEQ ID NO:5;
(BF) residues 196 to 217 of SEQ ID NO:6;
(BG) residues 195 to 216 of SEQ ID NO:7;
(BH) residues 195 to 216 of SEQ ID NO:8;
(BI) residues 191 to 212 of SEQ ID NO:9;
(BJ) residues 189 to 208 of SEQ ID NO:10;
(CA) residues 230 to 236 of SEQ ID NO:1;
(CB) residues 230 to 236 of SEQ ID NO:2;
(CC) residues 225 to 234 of SEQ ID NO:3;
(CD) residues 232 to 238 of SEQ ID NO:4;
(CE) residues 230 to 236 of SEQ ID NO:5;
(CF) residues 237 to 243 of SEQ ID NO:6;
(CG) residues 236 to 242 of SEQ ID NO:7;
(CH) residues 236 to 242 of SEQ ID NO:8;
(CI) residues 232 to 238 of SEQ ID NO:9; and
(CJ) residues 228 to 236 of SEQ ID NO:10.

8. The isolated protein of claim 1, comprising any of the following amino acid sequences selected from the group consisting of: SEQ ID NO:24; SEQ ID NO:26; SEQ ID NO:33; SEQ ID NO:36 and SEQ ID NO:38.

9. The isolated protein of claim 2, comprising any of the following amino acid sequences selected from the group consisting of SEQ ID NO:25; SEQ ID NO:27 and SEQ ID NO:39.

10. A pharmaceutical composition comprising one or more isolated proteins according to claim 1 and a pharmaceutically acceptable carrier, diluent or excipient.

11. A pharmaceutical composition comprising one or more isolated proteins according to claim 2 and a pharmaceutically acceptable carrier, diluent or excipient.

12. A method of therapeutically treating an *N. meningitidis* infection in a mammal including administering a pharmaceutically effective amount of the pharmaceutical composition of claim 10 to the mammal to thereby therapeutically treat said *N. meningitidis* infection.

13. A method of therapeutically treating an *Neisseria meningitidis* infection in a mammal including administering a pharmaceutically effective amount of the pharmaceutical composition of claim 11 to the mammal to thereby therapeutically treat the *Neisseria meningitidis* infection.

14. The method of claim 12, wherein administering the pharmaceutically effective amount of the pharmaceutical composition elicits an immune response to *Neisseria meningitidis*.

15. The method of claim 12, wherein the mammal is a human.

16. The method of claim 13, wherein the mammal is a human.

* * * * *

```
                        SEQUENCE LISTING

<160> NUMBER OF SEQ ID NOS: 52

<210> SEQ ID NO 1
<211> LENGTH: 591
<212> TYPE: PRT
<213> ORGANISM: Neisseria meningitidis

<400> SEQUENCE: 1

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
```

```
            115                 120                 125
Leu Lys Lys Asp Leu Thr Asp Leu Thr Ser Val Gly Thr Glu Lys Leu
    130                 135                 140
Ser Phe Ser Ala Asn Gly Asn Lys Val Asn Ile Thr Ser Asp Thr Lys
145                 150                 155                 160
Gly Leu Asn Phe Ala Lys Glu Thr Ala Gly Thr Asn Gly Asp Thr Thr
                165                 170                 175
Val His Leu Asn Gly Ile Gly Ser Thr Leu Thr Asp Thr Leu Leu Asn
            180                 185                 190
Thr Gly Ala Thr Thr Asn Val Thr Asn Asp Asn Val Thr Asp Asp Glu
        195                 200                 205
Lys Lys Arg Ala Ala Ser Val Lys Asp Val Leu Asn Ala Gly Trp Asn
    210                 215                 220
Ile Lys Gly Val Lys Pro Gly Thr Thr Ala Ser Asp Asn Val Asp Phe
225                 230                 235                 240
Val Arg Thr Tyr Asp Thr Val Glu Phe Leu Ser Ala Asp Thr Lys Thr
                245                 250                 255
Thr Thr Val Asn Val Glu Ser Lys Asp Asn Gly Lys Lys Thr Glu Val
            260                 265                 270
Lys Ile Gly Ala Lys Thr Ser Val Ile Lys Glu Lys Asp Gly Lys Leu
        275                 280                 285
Val Thr Gly Lys Asp Lys Gly Glu Asn Gly Ser Ser Thr Asp Glu Gly
    290                 295                 300
Glu Gly Leu Val Thr Ala Lys Glu Val Ile Asp Ala Val Asn Lys Ala
305                 310                 315                 320
Gly Trp Arg Met Lys Thr Thr Thr Ala Asn Gly Gln Thr Gly Gln Ala
                325                 330                 335
Asp Lys Phe Glu Thr Val Thr Ser Gly Thr Asn Val Thr Phe Ala Ser
            340                 345                 350
Gly Lys Gly Thr Thr Ala Thr Val Ser Lys Asp Gln Gly Asn Ile
        355                 360                 365
Thr Val Met Tyr Asp Val Asn Val Gly Asp Ala Leu Asn Val Asn Gln
    370                 375                 380
Leu Gln Asn Ser Gly Trp Asn Leu Asp Ser Lys Ala Val Ala Gly Ser
385                 390                 395                 400
Ser Gly Lys Val Ile Ser Gly Asn Val Ser Pro Ser Lys Gly Lys Met
                405                 410                 415
Asp Glu Thr Val Asn Ile Asn Ala Gly Asn Asn Ile Glu Ile Thr Arg
            420                 425                 430
Asn Gly Lys Asn Ile Asp Ile Ala Thr Ser Met Thr Pro Gln Phe Ser
        435                 440                 445
Ser Val Ser Leu Gly Ala Gly Ala Asp Ala Pro Thr Leu Ser Val Asp
    450                 455                 460
Gly Asp Ala Leu Asn Val Gly Ser Lys Lys Asp Asn Lys Pro Val Arg
465                 470                 475                 480
Ile Thr Asn Val Ala Pro Gly Val Lys Glu Gly Asp Val Thr Asn Val
                485                 490                 495
Ala Gln Leu Lys Gly Val Ala Gln Asn Leu Asn Asn Arg Ile Asp Asn
            500                 505                 510
Val Asp Gly Asn Ala Arg Ala Gly Ile Ala Gln Ala Ile Ala Thr Ala
        515                 520                 525
Gly Leu Val Gln Ala Tyr Leu Pro Gly Lys Ser Met Met Ala Ile Gly
    530                 535                 540
```

-continued

```
Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 2
<211> LENGTH: 592
<212> TYPE: PRT
<213> ORGANISM: Neisseria meningitidis

<400> SEQUENCE: 2

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Asn Ala Thr Asp Glu Asp Glu Glu Glu Leu Glu Ser Val Gln
50                  55                  60

Arg Ser Val Val Gly Ser Ile Gln Ala Ser Met Gly Gly Ser Val Glu
65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Glu Thr Glu Lys Leu
130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Met Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335
```

-continued

Asp Lys Phe Glu Thr Val Thr Ser Gly Thr Lys Val Thr Phe Ala Ser
             340                 345                 350

Gly Asn Gly Thr Thr Ala Thr Val Ser Lys Asp Asp Gln Gly Asn Ile
             355                 360                 365

Thr Val Lys Tyr Asp Val Asn Val Gly Asp Ala Leu Asn Val Asn Gln
             370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
             405                 410                 415

Asp Glu Thr Val Asn Ile Asn Ala Gly Asn Asn Ile Glu Ile Thr Arg
             420                 425                 430

Asn Gly Lys Asn Ile Asp Ile Ala Thr Ser Met Thr Pro Gln Phe Ser
             435                 440                 445

Ser Val Ser Leu Gly Ala Gly Ala Asp Ala Pro Thr Leu Ser Val Asp
             450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
             485                 490                 495

Val Ala Gln Leu Lys Gly Val Ala Gln Asn Leu Asn Asn Arg Ile Asp
             500                 505                 510

Asn Val Asn Gly Asn Ala Arg Ala Gly Ile Ala Gln Ala Ile Ala Thr
             515                 520                 525

Ala Gly Leu Val Gln Ala Tyr Leu Pro Gly Lys Ser Met Met Ala Ile
             530                 535                 540

Gly Gly Gly Thr Tyr Leu Gly Glu Ala Gly Tyr Ala Ile Gly Tyr Ser
545                 550                 555                 560

Ser Ile Ser Ala Gly Gly Asn Trp Ile Ile Lys Gly Thr Ala Ser Gly
             565                 570                 575

Asn Ser Arg Gly His Phe Gly Ala Ser Ala Ser Val Gly Tyr Gln Trp
             580                 585                 590

<210> SEQ ID NO 3
<211> LENGTH: 589
<212> TYPE: PRT
<213> ORGANISM: Neisseria meningitidis

<400> SEQUENCE: 3

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
             20                  25                  30

Thr Val Ala Thr Ala Val Leu Ala Thr Leu Ser Ala Thr Val Gln
             35                  40                  45

Ala Asn Ala Thr Asp Thr Asp Glu Asp Glu Leu Glu Ser Val Ala
             50                  55                  60

Arg Ser Ala Leu Val Leu Gln Phe Met Ile Asp Lys Glu Gly Asn Gly
65                  70                  75                  80

Glu Ile Glu Ser Thr Gly Asp Ile Gly Trp Ser Ile Tyr Tyr Asp Asp
             85                  90                  95

His Asn Thr Leu His Gly Ala Thr Val Thr Leu Lys Ala Gly Asp Asn
             100                 105                 110

Leu Lys Ile Lys Gln Ser Gly Lys Asp Phe Thr Tyr Ser Leu Lys Lys
             115                 120                 125

-continued

```
Glu Leu Lys Asp Leu Thr Ser Val Glu Thr Glu Lys Leu Ser Phe Gly
130                 135                 140

Ala Asn Gly Asn Lys Val Asn Ile Thr Ser Asp Thr Lys Gly Leu Asn
145                 150                 155                 160

Phe Ala Lys Glu Thr Ala Gly Thr Asn Gly Asp Pro Thr Val His Leu
                165                 170                 175

Asn Gly Ile Gly Ser Thr Leu Thr Asp Thr Leu Ala Gly Ser Ser Ala
                180                 185                 190

Ser His Val Asp Ala Gly Asn Gln Ser Thr His Tyr Thr Arg Ala Ala
            195                 200                 205

Ser Ile Lys Asp Val Leu Asn Ala Gly Trp Asn Ile Lys Gly Val Lys
210                 215                 220

Thr Gly Ser Thr Thr Gly Gln Ser Glu Asn Val Asp Phe Val Arg Thr
225                 230                 235                 240

Tyr Asp Thr Val Glu Phe Leu Ser Ala Asp Thr Lys Thr Thr Thr Val
                245                 250                 255

Asn Val Glu Ser Lys Asp Asn Gly Lys Arg Thr Glu Val Lys Ile Gly
                260                 265                 270

Ala Lys Thr Ser Val Ile Lys Glu Lys Asp Gly Lys Leu Val Thr Gly
            275                 280                 285

Lys Gly Lys Gly Glu Asn Gly Ser Ser Thr Asp Glu Gly Glu Gly Leu
290                 295                 300

Val Thr Ala Lys Glu Val Ile Asp Ala Val Asn Lys Ala Gly Trp Arg
305                 310                 315                 320

Met Lys Thr Thr Thr Ala Asn Gly Gln Thr Gly Gln Ala Asp Lys Phe
                325                 330                 335

Glu Thr Val Thr Ser Gly Thr Lys Val Thr Phe Ala Ser Gly Asn Gly
                340                 345                 350

Thr Thr Ala Thr Val Ser Lys Asp Asp Gln Gly Asn Ile Thr Val Lys
            355                 360                 365

Tyr Asp Val Asn Val Gly Asp Ala Leu Asn Val Asn Gln Leu Gln Asn
            370                 375                 380

Ser Gly Trp Asn Leu Asp Ser Lys Ala Val Ala Gly Ser Ser Gly Lys
385                 390                 395                 400

Val Ile Ser Gly Asn Val Ser Pro Ser Lys Gly Lys Met Asp Glu Thr
                405                 410                 415

Val Asn Ile Asn Ala Gly Asn Asn Ile Glu Ile Thr Arg Asn Gly Lys
                420                 425                 430

Asn Ile Asp Ile Ala Thr Ser Met Thr Pro Gln Phe Ser Ser Val Ser
            435                 440                 445

Leu Gly Ala Gly Ala Asp Ala Pro Thr Leu Ser Val Asp Asp Glu Gly
450                 455                 460

Ala Leu Asn Val Gly Ser Lys Asp Ala Asn Lys Pro Val Arg Ile Thr
465                 470                 475                 480

Asn Val Ala Pro Gly Val Lys Glu Gly Asp Val Thr Asn Val Ala Gln
                485                 490                 495

Leu Lys Gly Val Ala Gln Asn Leu Asn Asn Arg Ile Asp Asn Val Asn
            500                 505                 510

Gly Asn Ala Arg Ala Gly Ile Ala Gln Ala Ile Ala Thr Ala Gly Leu
            515                 520                 525

Ala Gln Ala Tyr Leu Pro Gly Lys Ser Met Met Ala Ile Gly Gly Gly
        530                 535                 540

Thr Tyr Leu Gly Glu Ala Gly Tyr Ala Ile Gly Tyr Ser Ser Ile Ser
545                 550                 555                 560
```

Asp Thr Gly Asn Trp Val Ile Lys Gly Thr Ala Ser Gly Asn Ser Arg
                565                 570                 575

Gly His Phe Gly Thr Ser Ala Ser Val Gly Tyr Gln Trp
            580                 585

<210> SEQ ID NO 4
<211> LENGTH: 594
<212> TYPE: PRT
<213> ORGANISM: Neisseria meningitidis

<400> SEQUENCE: 4

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Ala Thr Ala Val Leu Ala Thr Leu Phe Ala Thr Val Gln
        35                  40                  45

Ala Ser Thr Thr Asp Asp Asp Leu Tyr Leu Glu Pro Val Gln Arg
    50                  55                  60

Thr Ala Val Val Leu Ser Phe Arg Ser Asp Lys Glu Gly Thr Gly Glu
65                  70                  75                  80

Lys Glu Val Thr Glu Asp Ser Asn Trp Gly Val Tyr Phe Asp Lys Lys
                85                  90                  95

Gly Val Leu Thr Ala Gly Thr Ile Thr Leu Lys Ala Gly Asp Asn Leu
            100                 105                 110

Lys Ile Lys Gln Asn Thr Asn Glu Asn Thr Asn Ala Ser Ser Phe Thr
        115                 120                 125

Tyr Ser Leu Lys Lys Asp Leu Thr Asp Leu Thr Ser Val Gly Thr Glu
    130                 135                 140

Lys Leu Ser Phe Ser Ala Asn Ser Asn Lys Val Asn Ile Thr Ser Asp
145                 150                 155                 160

Thr Lys Gly Leu Asn Phe Ala Lys Lys Thr Ala Glu Thr Asn Gly Asp
                165                 170                 175

Thr Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Arg Thr
            260                 265                 270

Glu Val Lys Ile Gly Ala Lys Thr Ser Val Ile Lys Glu Lys Asp Gly
        275                 280                 285

Lys Leu Val Thr Gly Lys Asp Lys Gly Glu Asn Asp Ser Ser Thr Asp
    290                 295                 300

Lys Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
                325                 330                 335

Gln Ala Asp Lys Phe Glu Thr Val Thr Ser Gly Thr Asn Val Thr Phe
            340                 345                 350

```
Ala Ser Gly Lys Gly Thr Thr Ala Thr Val Ser Lys Asp Asp Gln Gly
            355                 360                 365

Asn Ile Thr Val Met Tyr Asp Val Asn Val Gly Asp Ala Leu Asn Val
        370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
            420                 425                 430

Thr Arg Asn Gly Lys Asn Ile Asp Ile Ala Thr Ser Met Thr Pro Gln
        435                 440                 445

Phe Ser Ser Val Ser Leu Gly Ala Gly Ala Asp Ala Pro Thr Leu Ser
    450                 455                 460

Val Asp Asp Glu Gly Ala Leu Asn Val Gly Ser Lys Asp Ala Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn His
            500                 505                 510

Ile Asp Asn Val Asp Gly Asn Ala Arg Ala Gly Ile Ala Gln Ala Ile
        515                 520                 525

Ala Thr Ala Gly Leu Val Gln Ala Tyr Leu Pro Gly Lys Ser Met Met
    530                 535                 540

Ala Ile Gly Gly Gly Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 5
<211> LENGTH: 591
<212> TYPE: PRT
<213> ORGANISM: Neisseria meningitidis

<400> SEQUENCE: 5

Met Asn Glu Ile Leu Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Ser Ala Asn Asn Glu Glu Gln Glu Glu Asp Leu Tyr Leu Asp Pro
        50                  55                  60

Val Leu Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
            115                 120                 125
```

```
Leu Lys Lys Asp Leu Thr Asp Leu Thr Ser Val Gly Thr Glu Lys Leu
    130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                    165                 170                 175

Val His Leu Asn Gly Ile Gly Ser Thr Leu Thr Asp Thr Leu Leu Asn
                180                 185                 190

Thr Gly Ala Thr Thr Asn Val Thr Asn Asp Asn Val Thr Asp Asp Glu
            195                 200                 205

Lys Lys Arg Ala Ala Ser Val Lys Asp Val Leu Asn Ala Gly Trp Asn
210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
                260                 265                 270

Lys Ile Gly Ala Lys Thr Ser Val Ile Lys Glu Lys Asp Gly Lys Leu
            275                 280                 285

Val Thr Gly Lys Asp Lys Gly Glu Asn Gly Ser Ser Thr Asp Glu Gly
        290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
                340                 345                 350

Gly Lys Gly Thr Thr Ala Thr Val Ser Lys Asp Asp Gln Gly Asn Ile
            355                 360                 365

Thr Val Met Tyr Asp Val Asn Val Gly Asp Ala Leu Asn Val Asn Gln
370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
                420                 425                 430

Asn Gly Lys Asn Ile Asp Ile Ala Thr Ser Met Thr Pro Gln Phe Ser
            435                 440                 445

Ser Val Ser Leu Gly Ala Gly Ala Asp Ala Pro Thr Leu Ser Val Asp
        450                 455                 460

Gly Asp Ala Leu Asn Val Gly Ser Lys Lys Asn Lys Pro Val Arg
465                 470                 475                 480

Ile Thr Asn Val Ala Pro Gly Val Lys Glu Asp Val Thr Asn Val
                485                 490                 495

Ala Gln Leu Lys Gly Val Ala Gln Asn Leu Asn Asn Arg Ile Asp Asn
                500                 505                 510

Val Asp Gly Asn Ala Arg Ala Gly Ile Ala Gln Ala Ile Ala Thr Ala
            515                 520                 525

Gly Leu Val Gln Ala Tyr Leu Pro Gly Lys Ser Met Met Ala Ile Gly
        530                 535                 540

Gly Gly Thr Tyr Arg Gly Glu Ala Gly Tyr Ala Ile Gly Tyr Ser Ser
545                 550                 555                 560
```

```
Ile Ser Asp Gly Gly Asn Trp Ile Ile Lys Gly Thr Ala Ser Gly Asn
            565                 570                 575

Ser Arg Gly His Phe Gly Ala Ser Ala Ser Val Gly Tyr Gln Trp
            580                 585                 590

<210> SEQ ID NO 6
<211> LENGTH: 599
<212> TYPE: PRT
<213> ORGANISM: Neisseria meningitidis

<400> SEQUENCE: 6

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Asn Ala Thr Asp Glu Asp Glu Glu Glu Leu Glu Pro Val Val
    50                  55                  60

Arg Ser Ala Leu Val Leu Gln Phe Met Ile Asp Lys Glu Gly Asn Gly
65                  70                  75                  80

Glu Asn Glu Ser Thr Gly Asn Ile Gly Trp Ser Ile Tyr Tyr Asp Asn
                85                  90                  95

His Asn Thr Leu His Gly Ala Thr Val Thr Leu Lys Ala Gly Asp Asn
            100                 105                 110

Leu Lys Ile Lys Gln Asn Thr Asn Lys Asn Thr Asn Glu Asn Thr Asn
        115                 120                 125

Asp Ser Ser Phe Thr Tyr Ser Leu Lys Lys Asp Leu Thr Asp Leu Thr
    130                 135                 140

Ser Val Glu Thr Glu Lys Leu Ser Phe Gly Ala Asn Gly Asn Lys Val
145                 150                 155                 160

Asn Ile Thr Ser Asp Thr Lys Gly Leu Asn Phe Ala Lys Glu Thr Ala
                165                 170                 175

Gly Thr Asn Gly Asp Thr Thr Val His Leu Asn Gly Ile Gly Ser Thr
            180                 185                 190

Leu Thr Asp Thr Leu Leu Asn Thr Gly Ala Thr Thr Asn Val Thr Asn
        195                 200                 205

Asp Asn Val Thr Asp Lys Lys Lys Arg Ala Ala Ser Val Lys Asp
    210                 215                 220

Val Leu Asn Ala Gly Trp Asn Ile Lys Gly Val Lys Pro Gly Thr Thr
225                 230                 235                 240

Ala Ser Asp Asn Val Asp Phe Val His Thr Tyr Asp Thr Val Glu Phe
                245                 250                 255

Leu Ser Ala Asp Thr Lys Thr Thr Val Asn Val Glu Ser Lys Asp
            260                 265                 270

Asn Gly Lys Arg Thr Glu Val Lys Ile Gly Ala Lys Thr Ser Val Ile
        275                 280                 285

Lys Glu Lys Asp Gly Lys Leu Val Thr Gly Lys Gly Lys Gly Glu Asn
    290                 295                 300

Gly Ser Ser Thr Asp Glu Gly Glu Gly Leu Val Thr Ala Lys Glu Val
305                 310                 315                 320

Ile Asp Ala Val Asn Lys Ala Gly Trp Arg Met Lys Thr Thr Thr Ala
                325                 330                 335

Asn Gly Gln Thr Gly Gln Ala Asp Lys Phe Glu Thr Val Thr Ser Gly
            340                 345                 350
```

Thr Asn Val Thr Phe Ala Ser Gly Lys Gly Thr Thr Ala Thr Val Ser
            355                 360                 365

Lys Asp Asp Gln Gly Asn Ile Thr Val Lys Tyr Asp Val Asn Val Gly
            370                 375                 380

Asp Ala Leu Asn Val Asn Gln Leu Gln Asn Ser Gly Trp Asn Leu Asp
385                 390                 395                 400

Ser Lys Ala Val Ala Gly Ser Ser Gly Lys Val Ile Ser Gly Asn Val
            405                 410                 415

Ser Pro Ser Lys Gly Lys Met Asp Glu Thr Val Asn Ile Asn Ala Gly
            420                 425                 430

Asn Asn Ile Glu Ile Thr Arg Asn Gly Lys Asn Ile Asp Ile Ala Thr
            435                 440                 445

Ser Met Thr Pro Gln Phe Ser Ser Val Ser Leu Gly Ala Gly Ala Asp
            450                 455                 460

Ala Pro Thr Leu Ser Val Asp Asp Lys Gly Ala Leu Asn Val Gly Ser
465                 470                 475                 480

Lys Asp Ala Asn Lys Pro Val Arg Ile Thr Asn Val Ala Pro Gly Val
            485                 490                 495

Lys Glu Gly Asp Val Thr Asn Val Ala Gln Leu Lys Gly Val Ala Gln
            500                 505                 510

Asn Leu Asn Asn Arg Ile Asp Asn Val Asp Gly Asn Ala Arg Ala Gly
            515                 520                 525

Ile Ala Gln Ala Ile Ala Thr Ala Gly Leu Val Gln Ala Tyr Leu Pro
            530                 535                 540

Gly Lys Ser Met Met Ala Ile Gly Gly Gly Thr Tyr Arg Gly Glu Ala
545                 550                 555                 560

Gly Tyr Ala Ile Gly Tyr Ser Ser Ile Ser Asp Gly Gly Asn Trp Ile
            565                 570                 575

Ile Lys Gly Thr Ala Ser Gly Asn Ser Arg Gly His Phe Gly Ala Ser
            580                 585                 590

Ala Ser Val Gly Tyr Gln Trp
            595

<210> SEQ ID NO 7
<211> LENGTH: 598
<212> TYPE: PRT
<213> ORGANISM: Neisseria meningitidis

<400> SEQUENCE: 7

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
            35                  40                  45

Ala Asn Ala Thr Asp Asp Asp Leu Tyr Leu Glu Pro Val Gln Arg
            50                  55                  60

Thr Ala Val Val Leu Ser Phe Arg Ser Asp Lys Glu Gly Thr Gly Glu
65                  70                  75                  80

Lys Glu Gly Thr Glu Asp Ser Asn Trp Ala Val Tyr Phe Asp Glu Lys
            85                  90                  95

Arg Val Leu Lys Ala Gly Ala Ile Thr Leu Lys Ala Gly Asp Asn Leu
            100                 105                 110

Lys Ile Lys Gln Asn Thr Asn Glu Asn Thr Asn Glu Asn Thr Asn Asp
            115                 120                 125

```
Ser Ser Phe Thr Tyr Ser Leu Lys Lys Asp Leu Thr Asp Leu Thr Ser
    130                 135                 140

Val Glu Thr Glu Lys Leu Ser Phe Gly Ala Asn Gly Asn Lys Val Asn
145                 150                 155                 160

Ile Thr Ser Asp Thr Lys Gly Leu Asn Phe Ala Lys Glu Thr Ala Gly
                165                 170                 175

Thr Asn Gly Asp Pro Thr Val His Leu Asn Gly Ile Gly Ser Thr Leu
            180                 185                 190

Thr Asp Thr Leu Leu Asn Thr Gly Ala Thr Thr Asn Val Thr Asn Asp
        195                 200                 205

Asn Val Thr Asp Asp Glu Lys Lys Arg Ala Ala Ser Val Lys Asp Val
    210                 215                 220

Leu Asn Ala Gly Trp Asn Ile Lys Gly Val Lys Pro Gly Thr Thr Ala
225                 230                 235                 240

Ser Asp Asn Val Asp Phe Val Arg Thr Tyr Asp Thr Val Glu Phe Leu
                245                 250                 255

Ser Ala Asp Thr Lys Thr Thr Thr Val Asn Val Glu Ser Lys Asp Asn
            260                 265                 270

Gly Lys Lys Thr Glu Val Lys Ile Gly Ala Lys Thr Ser Val Ile Lys
        275                 280                 285

Glu Lys Asp Gly Lys Leu Val Thr Gly Lys Gly Lys Asp Glu Asn Gly
    290                 295                 300

Ser Ser Thr Asp Glu Gly Glu Gly Leu Val Thr Ala Lys Glu Val Ile
305                 310                 315                 320

Asp Ala Val Asn Lys Ala Gly Trp Arg Met Lys Thr Thr Thr Ala Asn
                325                 330                 335

Gly Gln Thr Gly Gln Ala Asp Lys Phe Glu Thr Val Thr Ser Gly Thr
            340                 345                 350

Lys Val Thr Phe Ala Ser Gly Asn Gly Thr Thr Ala Thr Val Ser Lys
        355                 360                 365

Asp Asp Gln Gly Asn Ile Thr Val Lys Tyr Asp Val Asn Val Gly Asp
    370                 375                 380

Ala Leu Asn Val Asn Gln Leu Gln Asn Ser Gly Trp Asn Leu Asp Ser
385                 390                 395                 400

Lys Ala Val Ala Gly Ser Ser Gly Lys Val Ile Ser Gly Asn Val Ser
                405                 410                 415

Pro Ser Lys Gly Lys Met Asp Glu Thr Val Asn Ile Asn Ala Gly Asn
            420                 425                 430

Asn Ile Glu Ile Thr Arg Asn Gly Lys Asn Ile Asp Ile Ala Thr Ser
        435                 440                 445

Met Thr Pro Gln Phe Ser Ser Val Ser Leu Gly Ala Gly Ala Asp Ala
    450                 455                 460

Pro Thr Leu Ser Val Asp Asp Glu Gly Ala Leu Asn Val Gly Ser Lys
465                 470                 475                 480

Asp Ala Asn Lys Pro Val Arg Ile Thr Asn Val Ala Pro Gly Val Lys
                485                 490                 495

Glu Gly Asp Val Thr Asn Val Ala Gln Leu Lys Gly Val Ala Gln Asn
            500                 505                 510

Leu Asn Asn Arg Ile Asp Asn Val Asp Gly Asn Ala Arg Ala Gly Ile
        515                 520                 525

Ala Gln Ala Ile Ala Thr Ala Gly Leu Ala Gln Ala Tyr Leu Pro Gly
    530                 535                 540

Lys Ser Met Met Ala Ile Gly Gly Gly Thr Tyr Arg Gly Glu Ala Gly
```

```
                545                 550                 555                 560
Tyr Ala Ile Gly Tyr Ser Ser Ile Ser Asp Thr Gly Asn Trp Val Ile
                565                 570                 575

Lys Gly Thr Ala Ser Gly Asn Ser Arg Gly His Phe Gly Ala Ser Ala
                580                 585                 590

Ser Val Gly Tyr Gln Trp
                595

<210> SEQ ID NO 8
<211> LENGTH: 598
<212> TYPE: PRT
<213> ORGANISM: Neisseria meningitidis

<400> SEQUENCE: 8

Met Asn Lys Ile Ser Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Ala Thr Ala Val Leu Ala Thr Leu Leu Phe Ala Thr Val Gln
            35                  40                  45

Ala Asn Ala Thr Asp Asp Asp Asp Leu Tyr Leu Glu Pro Val Gln Arg
        50                  55                  60

Thr Ala Val Val Leu Ser Phe Arg Ser Asp Lys Glu Gly Thr Gly Glu
65                  70                  75                  80

Lys Glu Gly Thr Glu Asp Ser Asn Trp Ala Val Tyr Phe Asp Glu Lys
                85                  90                  95

Arg Val Leu Lys Ala Gly Ala Ile Thr Leu Lys Ala Gly Asp Asn Leu
                100                 105                 110

Lys Ile Lys Gln Asn Thr Asn Glu Asn Thr Asn Glu Asn Thr Asn Asp
            115                 120                 125

Ser Ser Phe Thr Tyr Ser Leu Lys Lys Asp Leu Thr Asp Leu Thr Ser
        130                 135                 140

Val Glu Thr Glu Lys Leu Ser Phe Gly Ala Asn Gly Asn Lys Val Asn
145                 150                 155                 160

Ile Thr Ser Asp Thr Lys Gly Leu Asn Phe Ala Lys Glu Thr Ala Gly
                165                 170                 175

Thr Asn Gly Asp Pro Thr Val His Leu Asn Gly Ile Gly Ser Thr Leu
                180                 185                 190

Thr Asp Thr Leu Leu Asn Thr Gly Ala Thr Thr Asn Val Thr Asn Asp
            195                 200                 205

Asn Val Thr Asp Asp Glu Lys Lys Arg Ala Ala Ser Val Lys Asp Val
        210                 215                 220

Leu Asn Ala Gly Trp Asn Ile Lys Gly Val Lys Pro Gly Thr Thr Ala
225                 230                 235                 240

Ser Asp Asn Val Asp Phe Val Arg Thr Tyr Asp Thr Val Glu Phe Leu
                245                 250                 255

Ser Ala Asp Thr Lys Thr Thr Thr Val Asn Val Glu Ser Lys Asp Asn
                260                 265                 270

Gly Lys Arg Thr Glu Val Lys Ile Gly Ala Lys Thr Ser Val Ile Lys
            275                 280                 285

Glu Lys Asp Gly Lys Leu Val Thr Gly Lys Gly Lys Gly Glu Asn Gly
        290                 295                 300

Ser Ser Thr Asp Glu Gly Glu Gly Leu Val Thr Ala Lys Glu Val Ile
305                 310                 315                 320

Asp Ala Val Asn Lys Ala Gly Trp Arg Met Lys Thr Thr Thr Ala Asn
```

```
                325                 330                 335
Gly Gln Thr Gly Gln Ala Asp Lys Phe Glu Thr Val Thr Ser Gly Thr
            340                 345                 350
Lys Val Thr Phe Ala Ser Gly Asn Gly Thr Thr Ala Thr Val Ser Lys
            355                 360                 365
Asp Gln Gly Asn Ile Thr Val Lys Tyr Asp Val Asn Val Gly Asp
        370                 375                 380
Ala Leu Asn Val Asn Gln Leu Gln Asn Ser Gly Trp Asn Leu Asp Ser
385                 390                 395                 400
Lys Ala Val Ala Gly Ser Ser Gly Lys Val Ile Ser Gly Asn Val Ser
                405                 410                 415
Pro Ser Lys Gly Lys Met Asp Glu Thr Val Asn Ile Asn Ala Gly Asn
            420                 425                 430
Asn Ile Glu Ile Thr Arg Asn Gly Lys Asn Ile Asp Ile Ala Thr Ser
        435                 440                 445
Met Thr Pro Gln Phe Ser Ser Val Ser Leu Gly Ala Gly Ala Asp Ala
    450                 455                 460
Pro Thr Leu Ser Val Asp Asp Glu Gly Ala Leu Asn Val Gly Ser Lys
465                 470                 475                 480
Asp Ala Asn Lys Pro Val Arg Ile Thr Asn Val Ala Pro Gly Val Lys
                485                 490                 495
Glu Gly Asp Val Thr Asn Val Ala Gln Leu Lys Gly Val Ala Gln Asn
            500                 505                 510
Leu Asn Asn Arg Ile Asp Asn Val Asp Gly Asn Ala Arg Ala Gly Ile
        515                 520                 525
Ala Gln Ala Ile Ala Thr Ala Gly Leu Ala Gln Ala Tyr Leu Pro Gly
    530                 535                 540
Lys Ser Met Met Ala Ile Gly Gly Gly Thr Tyr Arg Gly Glu Ala Gly
545                 550                 555                 560
Tyr Ala Ile Gly Tyr Ser Ser Ile Ser Asp Thr Gly Asn Trp Val Ile
                565                 570                 575
Lys Gly Thr Ala Ser Gly Asn Ser Arg Gly His Phe Gly Thr Ser Ala
            580                 585                 590
Ser Val Gly Tyr Gln Trp
        595

<210> SEQ ID NO 9
<211> LENGTH: 594
<212> TYPE: PRT
<213> ORGANISM: Neisseria meningitidis

<400> SEQUENCE: 9

Met Asn Lys Ile Tyr Arg Ile Ile Trp Asn Ser Ala Leu Asn Ala Trp
1               5                   10                  15
Val Val Ser Glu Leu Thr Arg Asn His Thr Lys Arg Ala Ser Ala
            20                  25                  30
Thr Val Ala Thr Ala Val Leu Ala Thr Leu Leu Phe Ala Thr Val Gln
        35                  40                  45
Ala Asn Ala Thr Asp Asp Asp Leu Tyr Leu Glu Pro Val Gln Arg
    50                  55                  60
Thr Ala Val Val Leu Ser Phe Arg Ser Asp Lys Glu Gly Thr Gly Glu
65                  70                  75                  80
Lys Glu Gly Thr Glu Asp Ser Asn Trp Ala Val Tyr Phe Asp Glu Lys
                85                  90                  95
Arg Val Leu Lys Ala Gly Ala Ile Thr Leu Lys Ala Gly Asp Asn Leu
```

```
              100                 105                 110
Lys Ile Lys Gln Asn Thr Asn Glu Asn Thr Asn Asp Ser Ser Phe Thr
            115                 120                 125
Tyr Ser Leu Lys Lys Asp Leu Thr Asp Leu Thr Ser Val Glu Thr Glu
            130                 135                 140
Lys Leu Ser Phe Gly Ala Asn Gly Asn Lys Val Asn Ile Thr Ser Asp
145                 150                 155                 160
Thr Lys Gly Leu Asn Phe Ala Lys Glu Thr Ala Gly Thr Asn Gly Asp
                165                 170                 175
Pro Thr Val His Leu Asn Gly Ile Gly Ser Thr Leu Thr Asp Thr Leu
            180                 185                 190
Leu Asn Thr Gly Ala Thr Thr Asn Val Thr Asn Asp Asn Val Thr Asp
            195                 200                 205
Asp Glu Lys Lys Arg Ala Ala Ser Val Lys Asp Val Leu Asn Ala Gly
            210                 215                 220
Trp Asn Ile Lys Gly Val Lys Pro Gly Thr Thr Ala Ser Asp Asn Val
225                 230                 235                 240
Asp Phe Val Arg Thr Tyr Asp Thr Val Glu Phe Leu Ser Ala Asp Thr
                245                 250                 255
Lys Thr Thr Thr Val Asn Val Glu Ser Lys Asp Asn Gly Lys Lys Thr
            260                 265                 270
Glu Val Lys Ile Gly Ala Lys Thr Ser Val Ile Lys Glu Lys Asp Gly
            275                 280                 285
Lys Leu Val Thr Gly Lys Gly Lys Asp Glu Asn Gly Ser Ser Thr Asp
            290                 295                 300
Glu Gly Glu Gly Leu Val Thr Ala Lys Glu Val Ile Asp Ala Val Asn
305                 310                 315                 320
Lys Ala Gly Trp Arg Met Lys Thr Thr Thr Ala Asn Gly Gln Thr Gly
                325                 330                 335
Gln Ala Asp Lys Phe Glu Thr Val Thr Ser Gly Thr Asn Val Thr Phe
            340                 345                 350
Ala Ser Gly Lys Gly Thr Thr Ala Thr Val Ser Lys Asp Asp Gln Gly
            355                 360                 365
Asn Ile Thr Val Lys Tyr Asp Val Asn Val Gly Asp Ala Leu Asn Val
            370                 375                 380
Asn Gln Leu Gln Asn Ser Gly Trp Asn Leu Asp Ser Lys Ala Val Ala
385                 390                 395                 400
Gly Ser Ser Gly Lys Val Ile Ser Gly Asn Val Ser Pro Ser Lys Gly
                405                 410                 415
Lys Met Asp Glu Thr Val Asn Ile Asn Ala Gly Asn Asn Ile Glu Ile
            420                 425                 430
Thr Arg Asn Gly Lys Asn Ile Asp Ile Ala Thr Ser Met Ala Pro Gln
            435                 440                 445
Phe Ser Ser Val Ser Leu Gly Ala Gly Ala Asp Ala Pro Thr Leu Ser
            450                 455                 460
Val Asp Asp Glu Gly Ala Leu Asn Val Gly Ser Lys Asp Thr Asn Lys
465                 470                 475                 480
Pro Val Arg Ile Thr Asn Val Ala Pro Gly Val Lys Glu Gly Asp Val
                485                 490                 495
Thr Asn Val Ala Gln Leu Lys Gly Val Ala Gln Asn Leu Asn Asn Arg
            500                 505                 510
Ile Asp Asn Val Asp Gly Asn Ala Arg Ala Gly Ile Ala Gln Ala Ile
            515                 520                 525
```

-continued

```
Ala Thr Ala Gly Leu Val Gln Ala Tyr Leu Pro Gly Lys Ser Met Met
        530                 535                 540

Ala Ile Gly Gly Asp Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 10
<211> LENGTH: 592
<212> TYPE: PRT
<213> ORGANISM: Neisseria meningitidis

<400> SEQUENCE: 10

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Asn Ala Thr Asp Glu Asp Glu Glu Glu Leu Glu Ser Val Gln
50                  55                  60

Arg Ser Val Val Gly Ser Ile Gln Ala Ser Met Glu Gly Ser Gly Glu
65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Glu Thr Glu Lys Leu
130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
            180                 185                 190

Ser Ser Ala Ser His Val Asp Ala Gly Asn Gln Ser Thr His Tyr Thr
        195                 200                 205

Arg Ala Ala Ser Ile Lys Asp Val Leu Asn Ala Gly Trp Asn Ile Lys
210                 215                 220

Gly Val Lys Thr Gly Ser Thr Thr Gly Gln Ser Glu Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Arg Thr Glu Val
            260                 265                 270

Lys Ile Gly Ala Lys Thr Ser Val Ile Lys Lys Asp Gly Lys Leu
        275                 280                 285

Val Thr Gly Lys Gly Lys Gly Glu Asn Gly Ser Ser Thr Asp Glu Gly
290                 295                 300

Glu Gly Leu Val Thr Ala Lys Glu Val Ile Asp Ala Val Asn Lys Ala
```

```
                305                 310                 315                 320
Gly Trp Arg Met Lys Thr Thr Thr Ala Asn Gly Gln Thr Gly Gln Ala
                    325                 330                 335

Asp Lys Phe Glu Thr Val Thr Ser Gly Thr Asn Val Thr Phe Ala Ser
                    340                 345                 350

Gly Lys Gly Thr Thr Ala Thr Val Ser Lys Asp Asp Gln Gly Asn Ile
                    355                 360                 365

Thr Val Met Tyr Asp Val Asn Val Gly Asp Ala Leu Asn Val Asn Gln
                    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                    405                 410                 415

Asp Glu Thr Val Asn Ile Asn Ala Gly Asn Asn Ile Glu Ile Ser Arg
                    420                 425                 430

Asn Gly Lys Asn Ile Asp Ile Ala Thr Ser Met Ala Pro Gln Phe Ser
                    435                 440                 445

Ser Val Ser Leu Gly Ala Gly Ala Asp Ala Pro Thr Leu Ser Val Asp
                    450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
                    485                 490                 495

Val Ala Gln Leu Lys Gly Val Ala Gln Asn Leu Asn Asn Arg Ile Asp
                    500                 505                 510

Asn Val Asp Gly Asn Ala Arg Ala Gly Ile Ala Gln Ala Ile Ala Thr
                    515                 520                 525

Ala Gly Leu Val Gln Ala Tyr Leu Pro Gly Lys Ser Met Met Ala Ile
                    530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
                    565                 570                 575

Asn Ser Arg Gly His Phe Gly Ala Ser Ala Ser Val Gly Tyr Gln Trp
                    580                 585                 590

<210> SEQ ID NO 11
<211> LENGTH: 604
<212> TYPE: PRT
<213> ORGANISM: Neisseria meningitidis
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
```

```
<222> LOCATION: (50)..(61)
<223> OTHER INFORMATION: Xaa can be any naturally occurring amino acid
<220> FEATURE:
<221> NAME/KEY: misc_feature
<222> LOCATION: (63)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (68)..(70)
<223> OTHER INFORMATION: Xaa can be any naturally occurring amino acid
<220> FEATURE:
<221> NAME/KEY: misc_feature
<222> LOCATION: (72)..(78)
<223> OTHER INFORMATION: Xaa can be any naturally occurring amino acid
<220> FEATURE:
<221> NAME/KEY: misc_feature
<222> LOCATION: (81)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (86)..(108)
<223> OTHER INFORMATION: Xaa can be any naturally occurring amino acid
<220> FEATURE:
<221> NAME/KEY: misc_feature
<222> LOCATION: (121)..(134)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (144)..(145)
<223> OTHER INFORMATION: Xaa can be any naturally occurring amino acid
<220> FEATURE:
<221> NAME/KEY: misc_feature
<222> LOCATION: (147)..(148)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (160)..(161)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
```

```
<222> LOCATION: (201)..(204)
<223> OTHER INFORMATION: Xaa can be any naturally occurring amino acid
<220> FEATURE:
<221> NAME/KEY: misc_feature
<222> LOCATION: (206)..(214)
<223> OTHER INFORMATION: Xaa can be any naturally occurring amino acid
<220> FEATURE:
<221> NAME/KEY: misc_feature
<222> LOCATION: (216)..(220)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (244)..(248)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (310)..(310)
<223> OTHER INFORMATION: Xaa can be any naturally occurring amino acid
<220> FEATURE:
<221> NAME/KEY: misc_feature
<222> LOCATION: (315)..(315)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (366)..(366)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (443)..(443)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (477)..(479)
<223> OTHER INFORMATION: Xaa can be any naturally occurring amino acid
<220> FEATURE:
<221> NAME/KEY: misc_feature
<222> LOCATION: (487)..(488)
<223> OTHER INFORMATION: Xaa can be any naturally occurring amino acid
<220> FEATURE:
<221> NAME/KEY: misc_feature
```

-continued

```
<222> LOCATION: (522)..(522)
<223> OTHER INFORMATION: Xaa can be any naturally occurring amino acid
<220> FEATURE:
<221> NAME/KEY: misc_feature
<222> LOCATION: (527)..(527)
<223> OTHER INFORMATION: Xaa can be any naturally occurring amino acid
<220> FEATURE:
<221> NAME/KEY: misc_feature
<222> LOCATION: (544)..(544)
<223> OTHER INFORMATION: Xaa can be any naturally occurring amino acid
<220> FEATURE:
<221> NAME/KEY: misc_feature
<222> LOCATION: (559)..(559)
<223> OTHER INFORMATION: Xaa can be any naturally occurring amino acid
<220> FEATURE:
<221> NAME/KEY: misc_feature
<222> LOCATION: (562)..(562)
<223> OTHER INFORMATION: Xaa can be any naturally occurring amino acid
<220> FEATURE:
<221> NAME/KEY: misc_feature
<222> LOCATION: (576)..(577)
<223> OTHER INFORMATION: Xaa can be any naturally occurring amino acid
<220> FEATURE:
<221> NAME/KEY: misc_feature
<222> LOCATION: (581)..(581)
<223> OTHER INFORMATION: Xaa can be any naturally occurring amino acid
<220> FEATURE:
<221> NAME/KEY: misc_feature
<222> LOCATION: (596)..(596)
<223> OTHER INFORMATION: Xaa can be any naturally occurring amino acid

<400> SEQUENCE: 11

Met Asn Xaa Ile Xaa Arg Ile Ile Trp Asn Ser Ala Leu Asn Ala Trp
1               5                   10                  15

Val Xaa Val Ser Glu Leu Thr Arg Asn His Thr Lys Arg Ala Ser Ala
            20                  25                  30

Thr Val Xaa Thr Ala Val Leu Ala Thr Leu Leu Xaa Ala Thr Val Gln
        35                  40                  45

Ala Xaa Xaa Xaa Xaa Xaa Xaa Xaa Xaa Xaa Xaa Xaa Xaa Leu Xaa Xaa
    50                  55                  60

Val Xaa Arg Xaa Xaa Xaa Val Xaa Xaa Xaa Xaa Xaa Xaa Xaa Glu Gly
65                  70                  75                  80

Xaa Xaa Glu Xaa Glu Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Thr Leu Lys Ala
            100                 105                 110

Gly Asp Asn Leu Lys Ile Lys Gln Xaa Xaa Xaa Xaa Xaa Xaa Xaa
        115                 120                 125

Xaa Xaa Xaa Xaa Xaa Xaa Phe Thr Tyr Ser Leu Lys Lys Xaa Leu Xaa
130                 135                 140

Xaa Leu Xaa Xaa Val Xaa Thr Glu Lys Leu Ser Phe Xaa Ala Asn Xaa
145                 150                 155                 160

Xaa Lys Val Asn Ile Xaa Ser Asp Thr Lys Gly Leu Asn Phe Ala Lys
                165                 170                 175

Xaa Thr Ala Xaa Thr Asn Gly Asp Xaa Thr Val His Leu Asn Gly Ile
            180                 185                 190

Gly Ser Thr Leu Thr Asp Xaa Leu Xaa Xaa Xaa Xaa Ala Xaa Xaa Xaa
        195                 200                 205

Xaa Xaa Xaa Xaa Xaa Xaa Thr Xaa Xaa Xaa Xaa Arg Ala Ala Ser
210                 215                 220

Xaa Lys Asp Val Leu Asn Ala Gly Trp Asn Ile Lys Gly Val Lys Xaa
225                 230                 235                 240

Gly Xaa Thr Xaa Xaa Xaa Xaa Xaa Asn Val Asp Phe Val Xaa Thr Tyr
                245                 250                 255
```

Asp Thr Val Glu Phe Leu Ser Ala Asp Thr Lys Thr Thr Val Asn
        260                 265                 270

Val Glu Ser Lys Asp Asn Gly Lys Xaa Thr Glu Val Lys Ile Gly Ala
    275                 280                 285

Lys Thr Ser Val Ile Lys Glu Lys Asp Gly Lys Leu Val Thr Gly Lys
    290                 295                 300

Xaa Lys Xaa Glu Asn Xaa Ser Ser Thr Asp Xaa Gly Glu Gly Leu Val
305                 310                 315                 320

Thr Ala Lys Glu Val Ile Asp Ala Val Asn Lys Ala Gly Trp Arg Met
                325                 330                 335

Lys Thr Thr Ala Asn Gly Gln Thr Gly Gln Ala Asp Lys Phe Glu
                340                 345                 350

Thr Val Thr Ser Gly Thr Xaa Val Thr Phe Ala Ser Gly Xaa Gly Thr
                355                 360                 365

Thr Ala Thr Val Ser Lys Asp Asp Gln Gly Asn Ile Thr Val Xaa Tyr
        370                 375                 380

Asp Val Asn Val Gly Asp Ala Leu Asn Val Asn Gln Leu Gln Asn Ser
385                 390                 395                 400

Gly Trp Asn Leu Asp Ser Lys Ala Val Ala Gly Ser Ser Gly Lys Val
                405                 410                 415

Ile Ser Gly Asn Val Ser Pro Ser Lys Gly Lys Met Asp Glu Thr Val
                420                 425                 430

Asn Ile Asn Ala Gly Asn Asn Ile Glu Ile Xaa Arg Asn Gly Lys Asn
            435                 440                 445

Ile Asp Ile Ala Thr Ser Met Xaa Pro Gln Phe Ser Ser Val Ser Leu
        450                 455                 460

Gly Ala Gly Ala Asp Ala Pro Thr Leu Ser Val Asp Xaa Xaa Xaa Ala
465                 470                 475                 480

Leu Asn Val Gly Ser Lys Xaa Xaa Asn Lys Pro Val Arg Ile Thr Asn
                485                 490                 495

Val Ala Pro Gly Val Lys Glu Gly Asp Val Thr Asn Val Ala Gln Leu
            500                 505                 510

Lys Gly Val Ala Gln Asn Leu Asn Asn Xaa Ile Asp Asn Val Xaa Gly
        515                 520                 525

Asn Ala Arg Ala Gly Ile Ala Gln Ala Ile Ala Thr Ala Gly Leu Xaa
530                 535                 540

Gln Ala Tyr Leu Pro Gly Lys Ser Met Met Ala Ile Gly Gly Xaa Thr
        545                 550                 555                 560

Tyr Xaa Gly Glu Ala Gly Tyr Ala Ile Gly Tyr Ser Ser Ile Ser Xaa
            565                 570                 575

Xaa Gly Asn Trp Xaa Ile Lys Gly Thr Ala Ser Gly Asn Ser Arg Gly
                580                 585                 590

His Phe Gly Xaa Ser Ala Ser Val Gly Tyr Gln Trp
            595                 600

<210> SEQ ID NO 12
<211> LENGTH: 1776
<212> TYPE: DNA
<213> ORGANISM: Neisseria meningitidis

<400> SEQUENCE: 12
atgaacaaaa taccgcat catttggaat agtgccctca atgcatgggt cgtcgtatcc       60
gagctcacac gcaaccacac caaacgcgcc tccgcaaccg tgaagaccgc cgtattggcg     120
actctgttgt ttgcaacggt tcaggcaagt gctaacaatg aagagcaaga agaagattta    180

```
tatttagacc cgtacaacg cactgttgcc gtgttgatag tcaattccga taaagaaggc    240
acgggagaaa aagaaaaagt agaagaaaat tcagattggg cagtatattt caacgagaaa    300
ggagtactaa cagccagaga atcaccctc aaagccggcg acaacctgaa atcaaacaa     360 aacggcacaa acttcaccta ctcgctgaaa aaagacctca cagatctgac cagtgttgga    420
actgaaaaat tatcgtttag cgcaaacggc aataaagtca acatcacaag cgacaccaaa    480
ggcttgaatt ttgcgaaaga aacggctggg acgaacggcg acaccacggt tcatctgaac    540
ggtattggtt cgactttgac cgatacgctg ctgaataccg gagcgaccac aaacgtaacc    600
aacgacaacg ttaccgatga cgagaaaaaa cgtgcggcaa gcgttaaaga cgtattaaac    660
gctggctgga acattaaagg cgttaaaccc ggtacaacag cttccgataa cgttgatttc    720
gtccgcactt acgacacagt cgagttcttg agcgcagata cgaaaacaac gactgttaat    780
gtggaaagca aagacaacgg caagaaaacc gaagttaaaa tcggtgcgaa gacttctgtt    840
attaaagaaa aagacggtaa gttggttact ggtaaagaca aaggcgagaa tggttcttct    900
acagacgaag gcgaaggctt agtgactgca aaagaagtga ttgatgcagt aaacaaggct    960
ggttggagaa tgaaaacaac aaccgctaat ggtcaaacag gtcaagctga caagtttgaa   1020
accgttacat caggcacaaa tgtaaccttt gctagtggta aggtacaac tgcgactgta    1080 agtaaagatg atcaaggcaa catcactgtt atgtatgatg taaatgtcgg cgatgcccta   1140
aacgtcaatc agctgcaaaa cagcggttgg aatttggatt ccaaagcggt tgcaggttct   1200
tcgggcaaag tcatcagcgg caatgtttcg ccgagcaagg gaaagatgga tgaaaccgtc   1260
aacattaatg ccggcaacaa catcgagatt acccgcaacg gtaaaaatat cgacatcgcc   1320
acttcgatga ccccgcagtt ttccagcgtt tcgctcggcg cggggcgga tgcgcccact    1380 ttgagcgtgg atggggacgc attgaatgtc ggcagcaaga aggacaacaa acccgtccgc   1440
attaccaatg tcgccccggg cgttaaagag ggggatgtta caaacgtcgc acaacttaaa   1500
ggcgtggcgc aaaacttgaa caaccgcatc gacaatgtgg acggcaacgc gcgtgcgggc   1560
atcgcccaag cgattgcaac cgcaggtctg gttcaggcgt atttgcccgg caagagtatg   1620
atggcgatcg gcggcggcac ttatcgcggc gaagccggtt acgccatcgg ctactccagt   1680
atttccgacg gcgaaattg gattatcaaa ggcacggctt ccggcaattc gcgcggccat    1740
ttcggtgctt ccgcatctgt cggttatcag tggtaa                              1776
```

<210> SEQ ID NO 13
<211> LENGTH: 1779
<212> TYPE: DNA
<213> ORGANISM: Neisseria meningitidis

<400> SEQUENCE: 13

```
atgaacaaaa tataccgcat catttggaat agtgccctca atgcctgggt cgccgtatcc     60
gagctcacac gcaaccacac caaacgcgcc tccgcaaccg tgaagaccgc cgtattggcg    120
acactgttgt ttgcaacggt tcaggcgaat gctaccgatg aagatgaaga agaagagtta    180
gaatccgtac aacgctctgt cgtagggagc attcaagcca gtatggaagg cagcgtcgaa    240
ttggaaacga tatcattatc aatgactaac gacagcaagg aatttgtaga cccatacata    300
gtagttaccc tcaaagccgg cgacaacctg aaaatcaaac aaaacaccaa tgaaaacacc    360
aatgccagta gcttcaccta ctcgctgaaa aaagacctca caggcctgat caatgttgaa    420
actgaaaaat tatcgtttgg cgcaaacggc aagaaagtca acatcataag cgacaccaaa    480
ggcttgaatt tcgcgaaaga aacggctggg acgaacggcg acaccacggt tcatctgaac    540
```

```
ggtatcggtt cgactttgac cgatatgctg ctgaataccg gagcgaccac aaacgtaacc    600
aacgacaacg ttaccgatga cgagaaaaaa cgtgcggcaa gcgttaaaga cgtattaaac    660
gcaggctgga acattaaagg cgttaaaccc ggtacaacag cttccgataa cgttgatttc    720
gtccgcactt acgacacagt cgagttcttg agcgcagata cgaaaacaac gactgttaat    780
gtggaaagca agacaacgg caagaaaacc gaagttaaaa tcggtgcgaa gacttctgtt    840
attaaagaaa aagacggtaa gttggttact ggtaaaggca aggcgagaa tggttcttct    900 acagacgaag gcgaaggctt agtgactgca aagaagtga ttgatgcagt aaacaaggct    960
ggttggagaa tgaaaacaac aaccgctaat ggtcaaacag gtcaagctga caagtttgaa    1020
accgttacat caggcacaaa agtaaccttt gctagtggta atggtacaac tgcgactgta    1080
agtaaagatg atcaaggcaa catcactgtt aagtatgatg taaatgtcgg cgatgcccta    1140
aacgtcaatc agctgcaaaa cagcggttgg aatttggatt ccaaagcggt tgcaggttct    1200
tcgggcaaag tcatcagcgg caatgtttcg ccgagcaagg gaaagatgga tgaaaccgtc    1260
aacattaatg ccggcaacaa catcgagatt acccgcaacg gcaaaaatat cgacatcgcc    1320
acttcgatga ccccgcaatt ttccagcgtt tcgctcggcg cggggggcgga tgcgcccact    1380 ttaagcgtgg atgacgaggg cgcgttgaat gtcggcagca aggatgccaa caaacccgtc    1440
cgcattacca atgtcgcccc gggcgttaaa gagggggatg ttacaaacgt cgcgcaactt    1500
aaaggtgtgg cgcaaaactt gaacaaccgc atcgacaatg tgaacggcaa cgcgcgtgcg    1560
ggcatcgccc aagcgattgc aaccgcaggt ctggttcagg cgtatctgcc cggcaagagt    1620
atgatggcga tcggcggcgg cacttatctc ggcgaagccg ttatgccat cggctactca    1680 agcatttccg ccggcggaaa ttggattatc aaaggcacgg cttccggcaa ttcgcgcggc    1740
catttcggtg cttccgcatc tgtcggttat cagtggtaa                         1779
```

<210> SEQ ID NO 14
<211> LENGTH: 1770
<212> TYPE: DNA
<213> ORGANISM: Neisseria meningitidis

<400> SEQUENCE: 14

```
atgaacaaaa tataccgcat catttggaat agtgccctca atgcctgggt agtcgtatcc     60
gagctcacac gcaaccacac caaacgcgcc tccgcaaccg tggcgaccgc cgtattggcg    120
acactgctgt ccgcaacggt tcaggcgaat gctaccgata ccgatgaaga tgaagagtta    180
gaatccgtag cacgctctgc tctggtgttg caattcatga tcgataaaga aggcaatgga    240
gaaatcgaat ctacaggaga tataggttgg agtatatatt acgacgatca caacactcta    300
cacggcgcaa ccgttaccct caaagccggc gacaacctga aaatcaaaca aagcggcaaa    360 gacttcaccct actcgctgaa aaagagctg aaagacctga ccagtgttga aactgaaaaa    420
ttatcgtttg gcgcaaacgg taataaagtc aacatcacaa gcgacaccaa aggcttgaat    480
tttgcgaaag aaacggctgg gacgaacggc gaccccacgg ttcatctgaa cggtatcggt    540
tcgactttga ccgatacgct tgcgggttct tctgcttctc acgttgatgc gggtaaccaa    600
agtacacatt acactcgtgc agcaagtatt aaggatgtgt tgaatgcggg ttggaatatt    660
aagggtgtta aaactggctc aacaactggt caatcagaaa atgtcgattt cgtccgcact    720
tacgacacag tcgagttctt gagcgcagat acgaaaacaa cgactgttaa tgtggaaagc    780
aaagacaacg gcaagagaac cgaagttaaa atcggtgcga agacttctgt tattaaagaa    840
aaagacggta agttggttac tggtaaaggc aaaggcgaga atggttcttc tacagacgaa    900
```

```
ggcgaaggct tagtgactgc aaaagaagtg attgatgcag taaacaaggc tggttggaga    960
atgaaaacaa caaccgctaa tggtcaaaca ggtcaagctg acaagtttga aaccgttaca   1020
tcaggcacaa aagtaaccct tgctagtggt aatggtacaa ctgcgactgt aagtaaagat   1080
gatcaaggca acatcactgt taagtatgat gtaaatgtcg gcgatgccct aaacgtcaat   1140
cagctgcaaa acagcggttg gaatttggat tccaaagcgg ttgcaggttc ttcgggcaaa   1200
gtcatcagcg gcaatgtttc gccgagcaag ggaaagatgg atgaaaccgt caacattaat   1260
gccggcaaca acatcgagat tacccgcaac ggcaaaaata tcgacatcgc cacttcgatg   1320
accccgcaat tttccagcgt ttcgctcggc gcggggcgg atgcgcccac tttaagcgtg   1380
gatgacgagg gcgcgttgaa tgtcggcagc aaggatgcca acaaacccgt ccgcattacc   1440
aatgtcgccc cgggcgttaa agaggggat gttacaaacg tcgcacaact taaaggtgtg   1500
gcgcaaaact tgaacaaccg catcgacaat gtgaacggca acgcgcgcgc gggtatcgcc   1560
caagcgattg caaccgcagg tttggctcag gcctatttgc ccggcaagag tatgatggcg   1620
atcggcggcg gtacttatct cggcgaagcc ggttacgcca tcggctactc gagcatttct   1680
gacactggga attgggttat caagggcacg gcttccggca attcgcgcgg tcatttcggt   1740
acttccgcat ctgtcggtta tcagtggtaa                                    1770
```

<210> SEQ ID NO 15
<211> LENGTH: 1785
<212> TYPE: DNA
<213> ORGANISM: Neisseria meningitidis

<400> SEQUENCE: 15

```
atgaacaaaa taccgcat catttggaat agtgccctca atgcctgggt cgccgtatcc      60
gagctcacac gcaaccacac caaacgcgcc tccgcaaccg tggcgaccgc cgtattggcg    120
acactgttgt ttgcaacggt tcaggcgagt actaccgatg acgacgattt atatttagaa    180
cccgtacaac gcactgctgt cgtgttgagc ttccgttccg ataaagaagg cacgggagaa    240
aaagaagtta cagaagattc aaattgggga gtatatttcg acaagaaagg agtactaaca    300
gccggaacaa tcaccctcaa agccggcgac aacctgaaaa tcaaacaaaa caccaatgaa    360
aacaccaatg ccagtagctt cacctactcg ctgaaaaaag acctcacaga tctgaccagt    420
gttggaactg aaaaattatc gtttagcgca acagcaata aagtcaacat cacaagcgac    480
accaaaggct tgaatttcgc gaaaaaaacg gctgagacca acggcgacac cacggttcat    540
ctgaacggta tcggttcgac tttgaccgat acgctgctga ataccggagc gaccacaaac    600
gtaaccaacg acaacgttac cgatgacgag aaaaaacgtg cggcaagcgt taaagacgta    660
ttaaacgcag gctggaacat taaaggcgtt aaacccggta caacagcttc cgataacgtt    720
gatttcgtcc gcacttacga cacagtcgag ttcttgagcg cagatacgaa acaacgact    780
gttaatgtgg aaagcaaaga caaggcaag agaaccgaag ttaaaatcgg tgcgaagact    840
tctgttatca agaaaaaga cggtaagttg ttactggta aagacaaagg cgagaatgat    900
tcttctacag acaaaggcga aggcttagtg actgcaaaag aagtgattga tgcagtaaac    960
aaggctggtt ggagaatgaa aacaacaacc gctaatggtc aaacaggtca agctgacaag   1020
tttgaaaccg ttcatcagg cacaaatgta accttttgcta gtggtaaagg tacaactgcg   1080
actgtaagta aagatgatca aggcaacatc actgttatgt atgatgtaaa tgtcggcgat   1140
gccctaaacg tcaatcagct gcaaaacagc ggttggaatt tggattccaa agcggttgca   1200
ggttcttcgg gcaaagtcat cagcggcaat gtttcgccga gcaagggaaa gatggatgaa   1260
```

```
accgtcaaca ttaatgccgg caacaacatc gagattaccc gcaacggcaa aaatatcgac   1320
atcgccactt cgatgacccc gcaattttcc agcgtttcgc tcggcgcggg ggcggatgcg   1380
cccactttaa gcgtggatga cgagggcgcg ttgaatgtcg gcagcaagga tgccaacaaa   1440
cccgtccgca ttaccaatgt cgccccgggc gttaagagg gggatgttac aaacgtcgca   1500
caacttaaag gcgtggcgca aaacttgaac aaccacatcg acaatgtgga cggcaacgcg   1560
cgtgcgggca tcgcccaagc gattgcaacc gcaggtctgg ttcaggcgta tctgcccggc   1620
aagagtatga tggcgatcgg cggcggcact tatcgcggcg aagccggtta tgccatcggc   1680
tactcaagca tttccgacgg cggaaattgg attatcaaag gcacggcttc cggcaattcg   1740
cgcggccatt tcggtgcttc cgcatctgtc ggttatcagt ggtaa                   1785
```

```
<210> SEQ ID NO 16
<211> LENGTH: 1776
<212> TYPE: DNA
<213> ORGANISM: Neisseria meningitidis

<400> SEQUENCE: 16
atgaacgaaa tattgcgcat catttggaat agcgccctca atgcctgggt cgttgtatcc     60
gagctcacac gcaaccacac caaacgcgcc tccgcaaccg tgaagaccgc cgtattggcg    120
actctgttgt ttgcaacggt tcaggcaagt gctaacaatg aagagcaaga agaagattta    180
tatttagacc ccgtgctacg cactgttgcc gtgttgatag tcaattccga taagaaggc     240 acgggagaaa aagaaaaagt agaagaaaat tcagattggg cagtatattt caacgagaaa    300
ggagtactaa cagccagaga aatcaccctc aaagccggcg acaacctgaa atcaaacaa     360 aacggcacaa acttcaccta ctcgctgaaa aaagacctca cagatctgac cagtgttgga    420
actgaaaaat tatcgtttag cgcaaacggc aataaagtca acatcacaag cgacaccaaa    480
ggcttgaatt ttgcgaaaga aacggctggg acgaacggcg acaccacggt tcatctgaac    540
ggtattggtt cgactttgac cgatacgctg ctgaataccg gagcgaccac aaacgtaacc    600
aacgacaacg ttaccgatga cgagaaaaaa cgtgcggcaa gcgttaaaga cgtattaaac    660
gctggctgga acattaaagg cgttaaaccc ggtacaacag cttccgataa cgttgatttc    720
gtccgcactt acgacacagt cgagttcttg agcgcagata cgaaaacaac gactgttaat    780
gtggaaagca aagacaacgg caagaaaacc gaagttaaaa tcggtgcgaa gacttctgtt    840
attaaagaaa aagacggtaa gttggttact ggtaaagaca aaggcgagaa tggttcttct    900
acagacgaag gcgaaggctt agtgactgca aaagaagtga ttgatgcagt aaacaaggct    960
ggttggagaa tgaaaacaac aaccgctaat ggtcaaacag gtcaagctga caagtttgaa   1020
accgttacat caggcacaaa tgtaaccttt gctagtggta aaggtacaac tgcgactgta   1080
agtaaagatg atcaaggcaa catcactgtt atgtatgatg taaatgtcgg cgatgcccta   1140
aacgtcaatc agctgcaaaa cagcggttgg aatttggatt ccaaagcggt tgcaggttct   1200
tcgggcaaag tcatcagcgg caatgttttc ccgagcaagg aaagatgga tgaaaccgtc   1260 aacattaatg ccggcaacaa catcgagatt acccgcaacg gtaaaaatat cgacatcgcc   1320
acttcgatga ccccgcagtt ttccagcgtt tcgctcggcg cggggcgga tgcgcccact   1380 ttgagcgtgg atggggacgc attgaatgtc ggcagcaaga aggacaacaa acccgtccgc   1440
attaccaatg tcgccccggg cgttaagagg gggatgttac aaacgtcgc acaacttaaa   1500 ggcgtggcgc aaaacttgaa caaccgcatc gacaatgtgg acggcaacgc gcgtgcgggc   1560
atcgcccaag cgattgcaac cgcaggtctg gttcaggcgt atttgcccgg caagagtatg   1620
```

-continued atggcgatcg gcggcggcac ttatcgcggc gaagccggtt acgccatcgg ctactccagt 1680
atttccgacg gcggaaattg gattatcaaa ggcacggctt ccggcaattc gcgcggccat 1740
ttcggtgctt ccgcatctgt cggttatcag tggtaa 1776

<210> SEQ ID NO 17
<211> LENGTH: 1800
<212> TYPE: DNA
<213> ORGANISM: Neisseria meningitidis

<400> SEQUENCE: 17
atgaacaaaa tataccgcat catttggaat agtgccctca atgcctgggt cgccgtatcc 60
gagctcacac gcaaccacac caaacgcgcc tccgcaaccg tgaagaccgc cgtattggcg 120
acgctgttgt ttgcaacggt tcaggcgaat gctaccgatg aagatgaaga agaagagtta 180
gaacccgtag tacgctctgc tctggtgttg caattcatga tcgataaaga aggcaatgga 240
gaaaacgaat ctacaggaaa tataggttgg agtatatatt acgacaatca caacactcta 300
cacggcgcaa ccgttaccct caaagccggc gacaacctga aaatcaaaca aaacaccaat 360
aaaaacacca atgaaaacac caatgacagt agcttcacct actcgctgaa aaaagacctc 420
acagatctga ccagtgttga aactgaaaaa ttatcgtttg gcgcaaacgg caataaagtc 480
aacatcacaa gcgacaccaa aggcttgaat ttcgcgaaag aaacggctgg gacgaacggc 540
gacaccacgg ttcatctgaa cggtattggt tcgactttga ccgatacgct gctgaatacc 600
ggagcgacca caaacgtaac caacgacaac gttaccgatg acaagaaaaa acgtgcggca 660
agcgttaaag acgtattaaa cgcaggctgg aacattaaag gcgttaaacc cggtacaaca 720
gcttccgata acgttgattt cgtccacact tacgacacag tcgagttctt gagcgcagat 780
acgaaaacaa cgactgttaa tgtggaaagc aaagacaacg gcaagagaac cgaagttaaa 840
atcggtgcga agacttctgt tattaaagaa aaagacggta agttggttac tggtaaaggc 900
aaaggcgaga atggttcttc tacagacgaa ggcgaaggct tagtgactgc aaaagaagtg 960
attgatgcag taaacaaggc tggttggaga atgaaaacaa caaccgctaa tggtcaaaca 1020
ggtcaagctg acaagtttga aaccgttaca tcaggcacaa atgtaacctt tgctagtggt 1080
aaaggtacaa ctgcgactgt aagtaaagat gatcaaggca acatcactgt taagtatgat 1140
gtaaatgtcg gcgatgccct aaacgtcaat cagctgcaaa acagcggttg gaatttggat 1200
tccaaagcgg ttgcaggttc ttcgggcaaa gtcatcagcg gcaatgtttc gccgagcaag 1260
ggaaagatgg atgaaaccgt caacattaat gccggcaaca acatcgagat tacccgcaac 1320
ggtaaaaata tcgacatcgc cacttcgatg accccgcagt tttccagcgt ttcgctcggc 1380
gcgggggcgg atgcgcccac tttgagcgtg gatgacaagg gcgcgttgaa tgtcggcagc 1440
aaggatgcca acaaacccgt ccgcattacc aatgtcgccc cgggcgttaa agagggggat 1500
gttacaaacg tcgcacaact taaaggcgtg gcgcaaaact tgaacaaccg catcgacaat 1560
gtggacggca acgcgcgtgc gggcatcgcc caagcgattg caaccgcagg tctggttcag 1620
gcgtatctgc ccggcaagag tatgatggcg atcggcggcg gcacttatcg cggcgaagcc 1680
ggttacgcca tcggctactc cagtatttcc gacggcggaa attggattat caaaggcacg 1740
gcttccggca attcgcgcgg tcatttcggt gcttccgcat ctgtcggtta tcagtggtaa 1800

<210> SEQ ID NO 18
<211> LENGTH: 1797
<212> TYPE: DNA
<213> ORGANISM: Neisseria meningitidis

<400> SEQUENCE: 18

```
atgaacaaaa tataccgcat catttggaat agtgccctca atgcctgggt cgtcgtatcc      60
gagctcacac gcaaccacac caaacgcgcc tccgcaaccg tggcgaccgc cgtattggcg     120
acactgttgt ttgcaacggt tcaggcgaat gctaccgatg acgacgattt atatttagaa     180
cccgtacaac gcactgctgt cgtgttgagc ttccgttccg ataaagaagg cacgggagaa     240
aaagaaggta cagaagattc aaattgggca gtatatttcg acgagaaaag agtactaaaa     300
gccggagcaa tcaccctcaa agccggcgac aacctgaaaa tcaaacaaaa caccaatgaa     360
aacaccaatg aaaacaccaa tgacagtagc ttcacctact ccctgaaaaa agacctcaca     420
gatctgacca gtgttgaaac tgaaaaatta tcgtttggcg caaacggtaa taaagtcaac     480
atcacaagcg acaccaaagg cttgaatttt gcgaaagaaa cggctgggac gaacggcgac     540
cccacggttc atctgaacgg tatcggttcg actttgaccg atacgctgct gaataccgga     600
gcgaccacaa acgtaaccaa cgacaacgtt accgatgacg agaaaaaacg tgcggcaagc     660
gttaaagacg tattaaacgc aggctggaac attaaaggcg ttaaacccgg tacaacagct     720
tccgataacg ttgatttcgt ccgcacttac gacacagtcg agttcttgag cgcagatacg     780
aaaacaacga ctgttaatgt ggaaagcaaa gacaacggca agaaaaccga gttaaaatc      840
ggtgcgaaga cttctgttat taagaaaaa gacggtaagt tggttactgg taaaggcaaa     900
gacgagaatg gttcttctac agacgaaggc gaaggcttag tgactgcaaa agaagtgatt     960
gatgcagtaa acaaggctgg ttggagaatg aaaacaacaa ccgctaatgg tcaaacaggt    1020
caagctgaca agtttgaaac cgttacatca ggcacaaaag taaccttttgc tagtggtaat    1080
ggtacaactg cgactgtaag taaagatgat caaggcaaca tcactgttaa gtatgatgta    1140
aatgtcggcg atgccctaaa cgtcaatcag ctgcaaaaca gcggttggaa tttggattcc    1200
aaagcggttg caggttcttc gggcaaagtc atcagcggca atgtttcgcc gagcaaggga    1260
aagatggatg aaaccgtcaa cattaatgcc ggcaacaaca tcgagattac ccgcaacggc    1320
aaaaatatcg acatcgccac ttcgatgacc ccgcaatttt ccagcgtttc gctcggcgcg    1380
ggggcggatg cgcccacttt aagcgtggat gacgagggcg cgttgaatgt cggcagcaag    1440
gatgccaaca aacccgtccg cattaccaat gtcgccccgg gcgttaaaga gggggatgtt    1500
acaaacgtcg cacaacttaa aggtgtggcg caaaacttga caaccgcat cgacaatgtg     1560
gacggcaacg cgcgcgcggg tatcgcccaa gcgattgcaa ccgcaggttt ggctcaggcg    1620
tatttgcccg gcaagagtat gatggcgatc ggcggcggta cttatcgcgg cgaagccggt    1680
tacgccatcg gctactcgag catttctgac actgggaatt gggttatcaa gggcacggct    1740
tccggcaatt cgcgcggcca tttcggtgct tccgcatctg tcggttatca gtggtaa      1797
```

<210> SEQ ID NO 19
<211> LENGTH: 1797
<212> TYPE: DNA
<213> ORGANISM: Neisseria meningitidis

<400> SEQUENCE: 19

```
atgaacaaaa tatcccgcat catttggaat agtgccctca atgcctgggt cgtcgtatcc      60
gagctcacac gcaaccacac caaacgcgcc tccgcaaccg tggcgaccgc cgtattggcg     120
acactgttgt ttgcaacggt tcaggcgaat gctaccgatg acgacgattt atatttagaa     180
cccgtacaac gcactgctgt cgtgttgagc ttccgttccg ataaagaagg cacgggagaa     240
aaagaaggta cagaagattc aaattgggca gtatatttcg acgagaaaag agtactaaaa     300
```

```
gccggagcaa tcaccctcaa agccggcgac aacctgaaaa tcaaacaaaa caccaatgaa    360
aacaccaatg aaaacaccaa tgacagtagc ttcacctact ccctgaaaaa agacctcaca    420
gatctgacca gtgttgaaac tgaaaaatta tcgtttggcg caaacggtaa taaagtcaac    480
atcacaagcg acaccaaagg cttgaatttt gcgaaagaaa cggctgggac gaacggcgac    540
cccacggttc atctgaacgg tatcggttcg actttgaccg atacgctgct gaataccgga    600
gcgaccacaa acgtaaccaa cgacaacgtt accgatgacg agaaaaaacg tgcggcaagc    660
gttaaagacg tattaaacgc aggctggaac attaaaggcg ttaaacccgg tacaacagct    720
tccgataacg tcgatttcgt ccgcacttac gacacagtcg agttcttgag cgcagatacg    780
aaaacaacga ctgttaatgt ggaaagcaaa gacaacggca agagaaccga agttaaaatc    840
ggtgcgaaga cttctgttat aaagaaaaaa gacggtaagt tggttactgg taaaggcaaa    900
ggcgagaatg gttcttctac agacgaaggc gaaggcttag tgactgcaaa agaagtgatt    960
gatgcagtaa acaaggctgg ttggagaatg aaaacaacaa ccgctaatgg tcaaacaggt   1020
caagctgaca gtttgaaaac cgttacatca ggcacaaaag taacctttgc tagtggtaat   1080
ggtacaactg cgactgtaag taaagatgat caaggcaaca tcactgttaa gtatgatgta   1140
aatgtcggcg atgccctaaa cgtcaatcag ctgcaaaaca gcggttggaa tttggattcc   1200
aaagcggttg caggttcttc gggcaaagtc atcagcggca atgtttcgcc gagcaaggga   1260
aagatggatg aaaccgtcaa cattaatgcc ggcaacaaca tcgagattac ccgcaacggc   1320
aaaaatatcg acatcgccac ttcgatgacc ccgcaatttt ccagcgtttc gctcggcgcg   1380
ggggcggatg cgcccacttt aagcgtggat gacgagggcg cgttgaatgt cggcagcaag   1440
gatgccaaca aacccgtccg cattaccaat gtcgccccgg gcgttaaaga gggggatgtt   1500
acaaacgtcg cacaacttaa aggtgtggcg caaaacttga caaccgcatc gacaatgtg   1560 gacggcaacg cgcgcgcggg tatcgcccaa gcgattgcaa ccgcaggttt ggctcaggcc   1620
tatttgcccg gcaagagtat gatggcgatc ggcggcggta cttatcgcgg cgaagccggt   1680
tacgccatcg gctactcgag catttctgac actgggaatt gggttatcaa gggcacggct   1740
tccggcaatt cgcgcggtca tttcggtact tccgcatctg tcggttatca gtggtaa     1797

<210> SEQ ID NO 20
<211> LENGTH: 1785
<212> TYPE: DNA
<213> ORGANISM: Neisseria meningitidis

<400> SEQUENCE: 20
atgaacaaaa tataccgcat catttggaat agtgccctca atgcctgggt cgtcgtatcc     60
gagctcacac gcaaccacac caaacgcgcc tccgcaaccg tggcgaccgc cgtattggcg    120
acactgttgt ttgcaacggt tcaggcgaat gctaccgatg acgacgattt atatttagaa    180
cccgtacaac gcactgctgt cgtgttgagc ttccgttccg ataaagaagg cacgggagaa    240
aaagaaggta cagaagattc aaattgggca gtatatttcg acgagaaaag agtactaaaa    300
gccggagcaa tcaccctcaa agccggcgac aacctgaaaa tcaaacaaaa caccaatgaa    360
aacaccaatg acagtagctt cacctactcc ctgaaaaaag acctcacaga tctgaccagt    420
gttgaaactg aaaaattatc gtttggcgca acggtaata aagtcaacat cacaagcgac    480
accaaaggct tgaattttgc gaaagaaacg ctgggacga acggcgaccc cacggttcat    540
ctgaacggta tcggttcgac tttgaccgat acgctgctga ataccggagc gaccacaaac    600
gtaaccaacg acaacgttac cgatgacgag aaaaaacgtg cggcaagcgt taaagacgta    660
```

```
ttaaacgcag gctggaacat taaaggcgtt aaacccggta caacagcttc cgataacgtt      720
gatttcgtcc gcacttacga cacagtcgag ttcttgagcg cagatacgaa acaacgact      780 gttaatgtgg aaagcaaaga caacggcaag aaaaccgaag ttaaaatcgg tgcgaagact     840
tctgttatta agaaaaaga cggtaagttg gttactggta aaggcaaaga cgagaatggt      900
tcttctacag acgaaggcga aggcttagtg actgcaaaag aagtgattga tgcagtaaac     960
aaggctggtt ggagaatgaa acaacaacc gctaatggtc aaacaggtca agctgacaag      1020
tttgaaaccg ttacatcagg cacaaatgta acctttgcta gtggtaaagg tacaactgcg     1080
actgtaagta aagatgatca aggcaacatc actgttaagt atgatgtaaa tgtcggcgat     1140
gccctaaacg tcaatcagct gcaaaacagc ggttggaatt tggattccaa agcggttgca     1200
ggttcttcgg gcaaagtcat cagcggcaat gtttcgccga gcaagggaaa gatggatgaa     1260
accgtcaaca ttaatgccgg caacaacatc gagattaccc gcaacggtaa aaatatcgac     1320
atcgccactt cgatggcgcc gcagttttcc agctttcgc tcggtgcggg gcggatgcg       1380 cccactttga gcgtggatga cgagggcgcg ttgaatgtcg gcagcaagga taccaacaaa     1440
cccgtccgca ttaccaatgt cgccccgggc gttaaagagg gggatgttac aaacgtcgca     1500
caacttaaag gcgtggcgca aaacttgaac aaccgcatcg acaatgtgga cggcaacgcg     1560
cgtgcgggca tcgcccaagc gattgcaacc gcaggtctag ttcaggcgta tctgcccggc     1620
aagagtatga tggcgatcgg cggcgacact tatcgcggcg aagccggtta cgccatcggc     1680
tactcaagta tttccgacgg cggaaattgg attatcaaag gcacggcttc cggcaattcg     1740
cgcggccatt tcggtgcttc cgcatctgtc ggttatcaat ggtaa                     1785

<210> SEQ ID NO 21
<211> LENGTH: 1779
<212> TYPE: DNA
<213> ORGANISM: Neisseria meningitidis

<400> SEQUENCE: 21
atgaacaaaa tataccgcat catttggaat agtgccctca atgcctgggt cgccgtatcc     60
gagctcacac gcaaccacac caaacgcgcc tccgcaaccg tgaagaccgc cgtattggcg     120
acactgttgt ttgcaacggt tcaggcgaat gctaccgatg aagatgaaga agaagagtta     180
gaatccgtac aacgctctgt cgtagggagc attcaagcca gtatggaagg cagcggcgaa     240
ttggaaacga tatcattatc aatgactaac gacagcaagg aatttgtaga cccatacata     300
gtagttaccc tcaaagccgg cgacaacctg aaaatcaaac aaaacaccaa tgaaaacacc     360
aatgccagta gcttcaccta ctcgctgaaa aaagacctca caggcctgat caatgttgaa     420
actgaaaaat tatcgtttgg cgcaaacggc aagaaagtca acatcataag cgacaccaaa     480
ggcttgaatt tcgcgaaaga aacggctggg acgaacggcg acaccacggt tcatctgaac     540
ggtatcggtt cgactttgac cgatacgctt gcgggttctt ctgcttctca cgttgatgcg     600
ggtaaccaaa gtacacatta cactcgtgca gcaagtatta aggatgtgtt gaatgcgggt     660
tggaatatta agggtgttaa aactggctca acaactggtc aatcagaaaa tgtcgatttc     720
gtccgcactt acgacacagt cgagttcttg agcgcagata cgaaaacaac gactgttaat     780
gtggaaagca agacaacgg caagagaacc gaagttaaaa tcggtgcgaa gacttctgtt    840
attaaagaaa aagacggtaa gttggttact ggtaaaggca aaggcgagaa tggttcttct     900
acagacgaag gcgaaggctt agtgactgca aagaagtga ttgatgcagt aaacaaggct      960
ggttggagaa tgaaaacaac aaccgctaat ggtcaaacag gtcaagctga caagtttgaa    1020
```

```
accgttacat caggcacaaa tgtaaccttt gctagtggta aaggtacaac tgcgactgta    1080
agtaaagatg atcaaggcaa catcactgtt atgtatgatg taaatgtcgg cgatgcccta    1140
aacgtcaatc agctgcaaaa cagcggttgg aatttggatt ccaaagcggt tgcaggttct    1200
tcgggcaaag tcatcagcgg caatgtttcg ccgagcaagg gaaagatgga tgaaaccgtc    1260
aacattaatg ccggcaacaa catcgagatt agccgcaacg gtaaaaatat cgacatcgcc    1320
acttcgatgg cgccgcagtt ttccagcgtt tcgctcggcg cggggggcaga tgcgcccact    1380 ttaagcgtgg atgacgaggg cgcgttgaat gtcggcagca aggatgccaa caaacccgtc    1440
cgcattacca atgtcgcccc gggcgttaaa gagggggatg ttacaaacgt cgcacaactt    1500
aaaggcgtgg cgcaaaactt gaacaaccgc atcgacaatg tggacggcaa cgcgcgtgcg    1560
ggcatcgccc aagcgattgc aaccgcaggt ctggttcagg cgtatctgcc cggcaagagt    1620
atgatggcga tcggcggcgg cacttatcgc ggcgaagccg gttacgccat cggctactcc    1680
agtatttccg acggcggaaa ttggattatc aaaggcacgg cttccggcaa ttcgcgcggc    1740
catttcggtg cttccgcatc tgtcggttat cagtggtaa                          1779
```

<210> SEQ ID NO 22
<211> LENGTH: 1815
<212> TYPE: DNA
<213> ORGANISM: Neisseria meningitidis
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (103)..(104)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t

```
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (160)..(162)
<223> OTHER INFORMATION: n is a, c, g, or t
<220> FEATURE:
<221> NAME/KEY: misc_feature
<222> LOCATION: (165)..(174)
<223> OTHER INFORMATION: n is a, c, g, or t
<220> FEATURE:
<221> NAME/KEY: misc_feature
<222> LOCATION: (177)..(179)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (189)..(190)
<223> OTHER INFORMATION: n is a, c, g, or t
<220> FEATURE:
<221> NAME/KEY: misc_feature
<222> LOCATION: (195)..(197)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (206)..(210)
<223> OTHER INFORMATION: n is a, c, g, or t
<220> FEATURE:
<221> NAME/KEY: misc_feature
<222> LOCATION: (212)..(220)
<223> OTHER INFORMATION: n is a, c, g, or t
<220> FEATURE:
<221> NAME/KEY: misc_feature
<222> LOCATION: (222)..(227)
<223> OTHER INFORMATION: n is a, c, g, or t
<220> FEATURE:
<221> NAME/KEY: misc_feature
<222> LOCATION: (229)..(230)
<223> OTHER INFORMATION: n is a, c, g, or t
<220> FEATURE:
<221> NAME/KEY: misc_feature
<222> LOCATION: (233)..(234)
<223> OTHER INFORMATION: n is a, c, g, or t
<220> FEATURE:
<221> NAME/KEY: misc_feature
<222> LOCATION: (242)..(243)
<223> OTHER INFORMATION: n is a, c, g, or t
<220> FEATURE:
<221> NAME/KEY: misc_feature
<222> LOCATION: (245)..(246)
<223> OTHER INFORMATION: n is a, c, g, or t
<220> FEATURE:
<221> NAME/KEY: misc_feature
<222> LOCATION: (250)..(252)
<223> OTHER INFORMATION: n is a, c, g, or t
<220> FEATURE:
<221> NAME/KEY: misc_feature
<222> LOCATION: (256)..(260)
<223> OTHER INFORMATION: n is a, c, g, or t
```

-continued

```
<220> FEATURE:
<221> NAME/KEY: misc_feature
<222> LOCATION: (262)..(286)
<223> OTHER INFORMATION: n is a, c, g, or t
<220> FEATURE:
<221> NAME/KEY: misc_feature
<222> LOCATION: (288)..(322)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (364)..(401)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (434)..(435)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (478)..(478)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (497)..(497)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
```

```
<220> FEATURE:
<221> NAME/KEY: misc_feature
<222> LOCATION: (539)..(539)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (600)..(602)
<223> OTHER INFORMATION: n is a, c, g, or t
<220> FEATURE:
<221> NAME/KEY: misc_feature
<222> LOCATION: (604)..(605)
<223> OTHER INFORMATION: n is a, c, g, or t
<220> FEATURE:
<221> NAME/KEY: misc_feature
<222> LOCATION: (607)..(607)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (615)..(616)
<223> OTHER INFORMATION: n is a, c, g, or t
<220> FEATURE:
<221> NAME/KEY: misc_feature
<222> LOCATION: (618)..(624)
<223> OTHER INFORMATION: n is a, c, g, or t
<220> FEATURE:
<221> NAME/KEY: misc_feature
<222> LOCATION: (626)..(628)
<223> OTHER INFORMATION: n is a, c, g, or t
<220> FEATURE:
<221> NAME/KEY: misc_feature
<222> LOCATION: (630)..(634)
<223> OTHER INFORMATION: n is a, c, g, or t
<220> FEATURE:
<221> NAME/KEY: misc_feature
<222> LOCATION: (637)..(637)
<223> OTHER INFORMATION: n is a, c, g, or t
<220> FEATURE:
<221> NAME/KEY: misc_feature
<222> LOCATION: (639)..(641)
<223> OTHER INFORMATION: n is a, c, g, or t
<220> FEATURE:
<221> NAME/KEY: misc_feature
<222> LOCATION: (645)..(646)
<223> OTHER INFORMATION: n is a, c, g, or t
<220> FEATURE:
<221> NAME/KEY: misc_feature
<222> LOCATION: (649)..(649)
<223> OTHER INFORMATION: n is a, c, g, or t
<220> FEATURE:
<221> NAME/KEY: misc_feature
<222> LOCATION: (652)..(657)
<223> OTHER INFORMATION: n is a, c, g, or t
<220> FEATURE:
<221> NAME/KEY: misc_feature
<222> LOCATION: (659)..(660)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
```

-continued

```
<220> FEATURE:
<221> NAME/KEY: misc_feature
<222> LOCATION: (672)..(673)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (723)..(724)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (733)..(738)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
```

```
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (842)..(842)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t
<220> FEATURE:
<221> NAME/KEY: misc_feature
<222> LOCATION: (914)..(914)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (929)..(929)
<223> OTHER INFORMATION: n is a, c, g, or t
<220> FEATURE:
<221> NAME/KEY: misc_feature
<222> LOCATION: (943)..(943)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1328)..(1328)
<223> OTHER INFORMATION: n is a, c, g, or t
<220> FEATURE:
<221> NAME/KEY: misc_feature
<222> LOCATION: (1338)..(1338)
<223> OTHER INFORMATION: n is a, c, g, or t
<220> FEATURE:
<221> NAME/KEY: misc_feature
<222> LOCATION: (1366)..(1366)
<223> OTHER INFORMATION: n is a, c, g, or t
<220> FEATURE:
<221> NAME/KEY: misc_feature
<222> LOCATION: (1368)..(1368)
<223> OTHER INFORMATION: n is a, c, g, or t
<220> FEATURE:
<221> NAME/KEY: misc_feature
<222> LOCATION: (1374)..(1374)
<223> OTHER INFORMATION: n is a, c, g, or t
<220> FEATURE:
<221> NAME/KEY: misc_feature
<222> LOCATION: (1395)..(1395)
<223> OTHER INFORMATION: n is a, c, g, or t
<220> FEATURE:
<221> NAME/KEY: misc_feature
<222> LOCATION: (1404)..(1404)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1429)..(1433)
<223> OTHER INFORMATION: n is a, c, g, or t
<220> FEATURE:
<221> NAME/KEY: misc_feature
<222> LOCATION: (1436)..(1436)
<223> OTHER INFORMATION: n is a, c, g, or t
```

-continued

```
<220> FEATURE:
<221> NAME/KEY: misc_feature
<222> LOCATION: (1440)..(1440)
<223> OTHER INFORMATION: n is a, c, g, or t
<220> FEATURE:
<221> NAME/KEY: misc_feature
<222> LOCATION: (1459)..(1459)
<223> OTHER INFORMATION: n is a, c, g, or t
<220> FEATURE:
<221> NAME/KEY: misc_feature
<222> LOCATION: (1461)..(1463)
<223> OTHER INFORMATION: n is a, c, g, or t
<220> FEATURE:
<221> NAME/KEY: misc_feature
<222> LOCATION: (1530)..(1530)
<223> OTHER INFORMATION: n is a, c, g, or t
<220> FEATURE:
<221> NAME/KEY: misc_feature
<222> LOCATION: (1542)..(1542)
<223> OTHER INFORMATION: n is a, c, g, or t
<220> FEATURE:
<221> NAME/KEY: misc_feature
<222> LOCATION: (1565)..(1565)
<223> OTHER INFORMATION: n is a, c, g, or t
<220> FEATURE:
<221> NAME/KEY: misc_feature
<222> LOCATION: (1579)..(1579)
<223> OTHER INFORMATION: n is a, c, g, or t
<220> FEATURE:
<221> NAME/KEY: misc_feature
<222> LOCATION: (1593)..(1593)
<223> OTHER INFORMATION: n is a, c, g, or t
<220> FEATURE:
<221> NAME/KEY: misc_feature
<222> LOCATION: (1599)..(1599)
<223> OTHER INFORMATION: n is a, c, g, or t
<220> FEATURE:
<221> NAME/KEY: misc_feature
<222> LOCATION: (1627)..(1627)
<223> OTHER INFORMATION: n is a, c, g, or t
<220> FEATURE:
<221> NAME/KEY: misc_feature
<222> LOCATION: (1629)..(1629)
<223> OTHER INFORMATION: n is a, c, g, or t
<220> FEATURE:
<221> NAME/KEY: misc_feature
<222> LOCATION: (1631)..(1631)
<223> OTHER INFORMATION: n is a, c, g, or t
<220> FEATURE:
<221> NAME/KEY: misc_feature
<222> LOCATION: (1638)..(1638)
<223> OTHER INFORMATION: n is a, c, g, or t
<220> FEATURE:
<221> NAME/KEY: misc_feature
<222> LOCATION: (1642)..(1642)
<223> OTHER INFORMATION: n is a, c, g, or t
<220> FEATURE:
<221> NAME/KEY: misc_feature
<222> LOCATION: (1676)..(1677)
<223> OTHER INFORMATION: n is a, c, g, or t
<220> FEATURE:
<221> NAME/KEY: misc_feature
<222> LOCATION: (1685)..(1685)
<223> OTHER INFORMATION: n is a, c, g, or t
<220> FEATURE:
<221> NAME/KEY: misc_feature
<222> LOCATION: (1701)..(1701)
<223> OTHER INFORMATION: n is a, c, g, or t
<220> FEATURE:
<221> NAME/KEY: misc_feature
<222> LOCATION: (1716)..(1716)
<223> OTHER INFORMATION: n is a, c, g, or t
<220> FEATURE:
<221> NAME/KEY: misc_feature
<222> LOCATION: (1719)..(1719)
<223> OTHER INFORMATION: n is a, c, g, or t
<220> FEATURE:
<221> NAME/KEY: misc_feature
<222> LOCATION: (1725)..(1725)
<223> OTHER INFORMATION: n is a, c, g, or t
```

```
<220> FEATURE:
<221> NAME/KEY: misc_feature
<222> LOCATION: (1727)..(1727)
<223> OTHER INFORMATION: n is a, c, g, or t
<220> FEATURE:
<221> NAME/KEY: misc_feature
<222> LOCATION: (1729)..(1731)
<223> OTHER INFORMATION: n is a, c, g, or t
<220> FEATURE:
<221> NAME/KEY: misc_feature
<222> LOCATION: (1734)..(1734)
<223> OTHER INFORMATION: n is a, c, g, or t
<220> FEATURE:
<221> NAME/KEY: misc_feature
<222> LOCATION: (1741)..(1741)
<223> OTHER INFORMATION: n is a, c, g, or t
<220> FEATURE:
<221> NAME/KEY: misc_feature
<222> LOCATION: (1749)..(1749)
<223> OTHER INFORMATION: n is a, c, g, or t
<220> FEATURE:
<221> NAME/KEY: misc_feature
<222> LOCATION: (1776)..(1776)
<223> OTHER INFORMATION: n is a, c, g, or t
<220> FEATURE:
<221> NAME/KEY: misc_feature
<222> LOCATION: (1786)..(1786)
<223> OTHER INFORMATION: n is a, c, g, or t
<220> FEATURE:
<221> NAME/KEY: misc_feature
<222> LOCATION: (1809)..(1809)
<223> OTHER INFORMATION: n is a, c, g, or t

<400> SEQUENCE: 22
atgaacnaaa tatnncgcat catttggaat agngccctca atgcntgggt ngnngtatcc      60
gagctcacac gcaaccacac caaacgcgcc tccgcaaccg tgnngaccgc cgtattggcg     120
acnctgntgt nngcaacggt tcaggcnant nctancnatn nngannnnnn nnnngannna     180
nanttagann ccgtnnnacg cnctgnnnnn gnnnnnnnnn tnnnnnncnn tanngaaggc     240
anngnngaan nngaannnnn annnnnnnnn nnnnnnnnnn nnnnnnannn nnnnnnnnnn     300
nnnnnnnnnn nnnnnnnnnn nntnaccctc aaagccggcg acaacctgaa aatcaaacaa     360
ancnnnnnnn nnnnnnnnnn nnnnnnnnnn nnnnnnnnnn ncttcaccta ctcnctgaaa     420
aaaganctna nagnnctgan cantgttgna actgaaaaat tatcgtttng cgcaaacngn     480
aanaaagtca acatcanaag cgacaccaaa ggcttgaatt tngcgaaana aacggctgng     540
acnaacggcg acnccacggt tcatctgaac ggtatnggtt cgactttgac cgatangctn     600
nngnntncnn nngcnncnnn nnnngnnncn nnnnacnann ntacnnatna cnnnnnnann     660
cgtgcngcaa gnnttaanga ngtnttnaan gcnggntgga anattaangg ngttaaancn     720
ggnncaacan ctnnnnnntc nganaangtn gatttcgtcc ncacttacga cacagtcgag     780
ttcttgagcg cagatacgaa acaacgact gttaatgtgg aaagcaaaga caacggcaag     840
anaaccgaag ttaaaatcgg tgcgaagact tctgttatna agaaaaaga cggtaagttg     900 gttactggta aagncaaagn cgagaatgnt tcttctacag acnaaggcga aggcttagtg     960
actgcaaaag aagtgattga tgcagtaaac aaggctggtt ggagaatgaa acaacaacc    1020 gctaatggtc aaacaggtca agctgacaag tttgaaaccg ttacatcagg cacaaangta    1080
acctttgcta gtggtaanngg tacaactgcg actgtaagta aagatgatca aggcaacatc    1140
actgttangt atgatgtaaa tgtcggcgat gccctaaacg tcaatcagct gcaaacagc     1200 ggttggaatt tggattccaa agcggttgca ggttcttcgg gcaaagtcat cagcggcaat    1260
gtttcgccga gcaagggaaa gatggatgaa accgtcaaca ttaatgccgg caacaacatc    1320
gagattancc gcaacggnaa aaatatcgac atcgccactt cgatgncncc gcantttcc     1380
```

-continued

```
agcgtttcgc tcggngcggg ggcngatgcg cccacttttna gcgtggatnn nnnggncgcn   1440
ttgaatgtcg gcagcaagna nnncaacaaa cccgtccgca ttaccaatgt cgccccgggc   1500
gttaaagagg gggatgttac aaacgtcgcn caacttaaag gngtggcgca aaacttgaac   1560
aaccncatcg acaatgtgna cggcaacgcg cgngcgggna tcgcccaagc gattgcaacc   1620
gcaggtntng ntcaggcnta tntgcccggc aagagtatga tggcgatcgg cggcgnnact   1680
tatcncggcg aagccggtta ngccatcggc tactcnagna tttcngncnn nggnaattgg   1740
nttatcaang gcacggcttc cggcaattcg cgcggncatt tcggtncttc cgcatctgtc   1800
ggttatcant ggtaa                                                    1815
```

<210> SEQ ID NO 23
<211> LENGTH: 512
<212> TYPE: PRT
<213> ORGANISM: Neisseria meningitidis

<400> SEQUENCE: 23

```
Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Thr Asp Leu Thr Ser Val Gly Thr Glu Lys
    50                  55                  60

Leu Ser Phe Ser Ala Asn Gly Asn Lys Val Asn Ile Thr Ser Asp Thr
65                  70                  75                  80

Lys Gly Leu Asn Phe Ala Lys Glu Thr Ala Gly Thr Asn Gly Asp Thr
                85                  90                  95

Thr Val His Leu Asn Gly Ile Gly Ser Thr Leu Thr Asp Thr Leu Leu
            100                 105                 110

Asn Thr Gly Ala Thr Thr Asn Val Thr Asn Asp Asn Val Thr Asp Asp
        115                 120                 125

Glu Lys Lys Arg Ala Ala Ser Val Lys Asp Val Leu Asn Ala Gly Trp
    130                 135                 140

Asn Ile Lys Gly Val Lys Pro Gly Thr Thr Ala Ser Asp Asn Val Asp
145                 150                 155                 160

Phe Val Arg Thr Tyr Asp Thr Val Glu Phe Leu Ser Ala Asp Thr Lys
                165                 170                 175

Thr Thr Thr Val Asn Val Glu Ser Lys Asp Asn Gly Lys Lys Thr Glu
            180                 185                 190

Val Lys Ile Gly Ala Lys Thr Ser Val Ile Lys Glu Lys Asp Gly Lys
        195                 200                 205

Leu Val Thr Gly Lys Asp Lys Gly Glu Asn Gly Ser Ser Thr Asp Glu
    210                 215                 220

Gly Glu Gly Leu Val Thr Ala Lys Glu Val Ile Asp Ala Val Asn Lys
225                 230                 235                 240

Ala Gly Trp Arg Met Lys Thr Thr Thr Ala Asn Gly Gln Thr Gly Gln
                245                 250                 255

Ala Asp Lys Phe Glu Thr Val Thr Ser Gly Thr Asn Val Thr Phe Ala
            260                 265                 270

Ser Gly Lys Gly Thr Thr Ala Thr Val Ser Lys Asp Asp Gln Gly Asn
        275                 280                 285

Ile Thr Val Met Tyr Asp Val Asn Val Gly Asp Ala Leu Asn Val Asn
```

```
                290                 295                 300
Gln Leu Gln Asn Ser Gly Trp Asn Leu Asp Ser Lys Ala Val Ala Gly
305                 310                 315                 320

Ser Ser Gly Lys Val Ile Ser Gly Asn Val Ser Pro Ser Lys Gly Lys
                325                 330                 335

Met Asp Glu Thr Val Asn Ile Asn Ala Gly Asn Asn Ile Glu Ile Thr
            340                 345                 350

Arg Asn Gly Lys Asn Ile Asp Ile Ala Thr Ser Met Thr Pro Gln Phe
        355                 360                 365

Ser Ser Val Ser Leu Gly Ala Gly Ala Asp Ala Pro Thr Leu Ser Val
    370                 375                 380

Asp Gly Asp Ala Leu Asn Val Gly Ser Lys Lys Asp Asn Lys Pro Val
385                 390                 395                 400

Arg Ile Thr Asn Val Ala Pro Gly Val Lys Glu Gly Asp Val Thr Asn
                405                 410                 415

Val Ala Gln Leu Lys Gly Val Ala Gln Asn Leu Asn Asn Arg Ile Asp
            420                 425                 430

Asn Val Asp Gly Asn Ala Arg Ala Gly Ile Ala Gln Ala Ile Ala Thr
        435                 440                 445

Ala Gly Leu Val Gln Ala Tyr Leu Pro Gly Lys Ser Met Met Ala Ile
    450                 455                 460

Gly Gly Gly Thr Tyr Arg Gly Glu Ala Gly Tyr Ala Ile Gly Tyr Ser
465                 470                 475                 480

Ser Ile Ser Asp Gly Gly Asn Trp Ile Ile Lys Gly Thr Ala Ser Gly
                485                 490                 495

Asn Ser Arg Gly His Phe Gly Ala Ser Ala Ser Val Gly Tyr Gln Trp
            500                 505                 510

<210> SEQ ID NO 24
<211> LENGTH: 513
<212> TYPE: PRT
<213> ORGANISM: Neisseria meningitidis

<400> SEQUENCE: 24

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Asn Ala Thr Asp Glu Thr Gly Leu Ile Asn Val Glu Thr Glu Lys
    50                  55                  60

Leu Ser Phe Gly Ala Asn Gly Lys Lys Val Asn Ile Ile Ser Asp Thr
65                  70                  75                  80

Lys Gly Leu Asn Phe Ala Lys Glu Thr Ala Gly Thr Asn Gly Asp Thr
                85                  90                  95

Thr Val His Leu Asn Gly Ile Gly Ser Thr Leu Thr Asp Met Leu Leu
            100                 105                 110

Asn Thr Gly Ala Thr Thr Asn Val Thr Asn Asp Asn Val Thr Asp Asp
        115                 120                 125

Glu Lys Lys Arg Ala Ala Ser Val Lys Asp Val Leu Asn Ala Gly Trp
    130                 135                 140

Asn Ile Lys Gly Val Lys Pro Gly Thr Thr Ala Ser Asp Asn Val Asp
145                 150                 155                 160

Phe Val Arg Thr Tyr Asp Thr Val Glu Phe Leu Ser Ala Asp Thr Lys
```

```
                    165                 170                 175
Thr Thr Thr Val Asn Val Glu Ser Lys Asp Asn Gly Lys Lys Thr Glu
                180                 185                 190

Val Lys Ile Gly Ala Lys Thr Ser Val Ile Lys Glu Lys Asp Gly Lys
            195                 200                 205

Leu Val Thr Gly Lys Gly Lys Gly Glu Asn Gly Ser Ser Thr Asp Glu
        210                 215                 220

Gly Glu Gly Leu Val Thr Ala Lys Glu Val Ile Asp Ala Val Asn Lys
225                 230                 235                 240

Ala Gly Trp Arg Met Lys Thr Thr Ala Asn Gly Gln Thr Gly Gln
                245                 250                 255

Ala Asp Lys Phe Glu Thr Val Thr Ser Gly Thr Lys Val Thr Phe Ala
            260                 265                 270

Ser Gly Asn Gly Thr Thr Ala Thr Val Ser Lys Asp Asp Gln Gly Asn
        275                 280                 285

Ile Thr Val Lys Tyr Asp Val Asn Val Gly Asp Ala Leu Asn Val Asn
    290                 295                 300

Gln Leu Gln Asn Ser Gly Trp Asn Leu Asp Ser Lys Ala Val Ala Gly
305                 310                 315                 320

Ser Ser Gly Lys Val Ile Ser Gly Asn Val Ser Pro Ser Lys Gly Lys
                325                 330                 335

Met Asp Glu Thr Val Asn Ile Asn Ala Gly Asn Asn Ile Glu Ile Thr
            340                 345                 350

Arg Asn Gly Lys Asn Ile Asp Ile Ala Thr Ser Met Thr Pro Gln Phe
        355                 360                 365

Ser Ser Val Ser Leu Gly Ala Gly Ala Asp Ala Pro Thr Leu Ser Val
    370                 375                 380

Asp Asp Glu Gly Ala Leu Asn Val Gly Ser Lys Asp Ala Asn Lys Pro
385                 390                 395                 400

Val Arg Ile Thr Asn Val Ala Pro Gly Val Lys Glu Gly Asp Val Thr
                405                 410                 415

Asn Val Ala Gln Leu Lys Gly Val Ala Gln Asn Leu Asn Asn Arg Ile
            420                 425                 430

Asp Asn Val Asn Gly Asn Ala Arg Ala Gly Ile Ala Gln Ala Ile Ala
        435                 440                 445

Thr Ala Gly Leu Val Gln Ala Tyr Leu Pro Gly Lys Ser Met Met Ala
    450                 455                 460

Ile Gly Gly Gly Thr Tyr Leu Gly Glu Ala Gly Tyr Ala Ile Gly Tyr
465                 470                 475                 480

Ser Ser Ile Ser Ala Gly Gly Asn Trp Ile Ile Lys Gly Thr Ala Ser
                485                 490                 495

Gly Asn Ser Arg Gly His Phe Gly Ala Ser Ala Ser Val Gly Tyr Gln
            500                 505                 510

Trp

<210> SEQ ID NO 25
<211> LENGTH: 407
<212> TYPE: PRT
<213> ORGANISM: Neisseria meningitidis

<400> SEQUENCE: 25

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30
```

```
Thr Val Lys Thr Ala Val Leu Ala Thr Leu Phe Ala Thr Val Gln
        35                  40                  45

Ala Ser Ala Asn Asn Val Asp Phe Val Arg Thr Tyr Asp Thr Val Glu
50                  55                  60

Phe Leu Ser Ala Asp Thr Lys Thr Thr Thr Val Asn Val Glu Ser Lys
65                  70                  75                  80

Asp Asn Gly Lys Lys Thr Glu Val Lys Ile Gly Ala Lys Thr Ser Val
                85                  90                  95

Ile Lys Glu Lys Asp Gly Lys Leu Val Thr Gly Lys Asp Lys Gly Glu
            100                 105                 110

Asn Gly Ser Ser Thr Asp Glu Gly Gly Leu Val Thr Ala Lys Glu
        115                 120                 125

Val Ile Asp Ala Val Asn Lys Ala Gly Trp Arg Met Lys Thr Thr Thr
    130                 135                 140

Ala Asn Gly Gln Thr Gly Gln Ala Asp Lys Phe Glu Thr Val Thr Ser
145                 150                 155                 160

Gly Thr Asn Val Thr Phe Ala Ser Gly Lys Gly Thr Thr Ala Thr Val
                165                 170                 175

Ser Lys Asp Asp Gln Gly Asn Ile Thr Val Met Tyr Asp Val Asn Val
            180                 185                 190

Gly Asp Ala Leu Asn Val Asn Gln Leu Gln Asn Ser Gly Trp Asn Leu
        195                 200                 205

Asp Ser Lys Ala Val Ala Gly Ser Ser Gly Lys Val Ile Ser Gly Asn
    210                 215                 220

Val Ser Pro Ser Lys Gly Lys Met Asp Glu Thr Val Asn Ile Asn Ala
225                 230                 235                 240

Gly Asn Asn Ile Glu Ile Thr Arg Asn Gly Lys Asn Ile Asp Ile Ala
                245                 250                 255

Thr Ser Met Thr Pro Gln Phe Ser Ser Val Ser Leu Gly Ala Gly Ala
            260                 265                 270

Asp Ala Pro Thr Leu Ser Val Asp Gly Asp Ala Leu Asn Val Gly Ser
        275                 280                 285

Lys Lys Asp Asn Lys Pro Val Arg Ile Thr Asn Val Ala Pro Gly Val
    290                 295                 300

Lys Glu Gly Asp Val Thr Asn Val Ala Gln Leu Lys Gly Val Ala Gln
305                 310                 315                 320

Asn Leu Asn Asn Arg Ile Asp Asn Val Asp Gly Asn Ala Arg Ala Gly
                325                 330                 335

Ile Ala Gln Ala Ile Ala Thr Ala Gly Leu Val Gln Ala Tyr Leu Pro
            340                 345                 350

Gly Lys Ser Met Met Ala Ile Gly Gly Thr Tyr Arg Gly Glu Ala
        355                 360                 365

Gly Tyr Ala Ile Gly Tyr Ser Ser Ile Ser Asp Gly Gly Asn Trp Ile
    370                 375                 380

Ile Lys Gly Thr Ala Ser Gly Asn Ser Arg Gly His Phe Gly Ala Ser
385                 390                 395                 400

Ala Ser Val Gly Tyr Gln Trp
                405

<210> SEQ ID NO 26
<211> LENGTH: 433
<212> TYPE: PRT
<213> ORGANISM: Neisseria meningitidis

<400> SEQUENCE: 26
```

-continued

```
Met Asn Lys Ile Tyr Arg Ile Ile Trp Asn Ser Ala Leu Asn Ala Trp
 1               5                  10                  15

Val Val Val Ser Glu Leu Thr Arg Asn His Thr Lys Arg Ala Ser Ala
             20                  25                  30

Thr Val Lys Thr Ala Val Leu Ala Thr Leu Leu Phe Ala Thr Val Gln
         35                  40                  45

Ala Ser Ala Asn Arg Ala Ala Ser Val Lys Asp Val Leu Asn Ala Gly
     50                  55                  60

Trp Asn Ile Lys Gly Val Lys Pro Gly Thr Thr Ala Ser Asp Asn Val
 65                  70                  75                  80

Asp Phe Val Arg Thr Tyr Asp Thr Val Glu Phe Leu Ser Ala Asp Thr
                 85                  90                  95

Lys Thr Thr Thr Val Asn Val Glu Ser Lys Asp Asn Gly Lys Lys Thr
            100                 105                 110

Glu Val Lys Ile Gly Ala Lys Thr Ser Val Ile Lys Glu Lys Asp Gly
        115                 120                 125

Lys Leu Val Thr Gly Lys Asp Lys Gly Glu Asn Gly Ser Ser Thr Asp
    130                 135                 140

Glu Gly Glu Gly Leu Val Thr Ala Lys Glu Val Ile Asp Ala Val Asn
145                 150                 155                 160

Lys Ala Gly Trp Arg Met Lys Thr Thr Thr Ala Asn Gly Gln Thr Gly
                165                 170                 175

Gln Ala Asp Lys Phe Glu Thr Val Thr Ser Gly Thr Asn Val Thr Phe
            180                 185                 190

Ala Ser Gly Lys Gly Thr Thr Ala Thr Val Ser Lys Asp Asp Gln Gly
        195                 200                 205

Asn Ile Thr Val Met Tyr Asp Val Asn Val Gly Asp Ala Leu Asn Val
    210                 215                 220

Asn Gln Leu Gln Asn Ser Gly Trp Asn Leu Asp Ser Lys Ala Val Ala
225                 230                 235                 240

Gly Ser Ser Gly Lys Val Ile Ser Gly Asn Val Ser Pro Ser Lys Gly
                245                 250                 255

Lys Met Asp Glu Thr Val Asn Ile Asn Ala Gly Asn Asn Ile Glu Ile
            260                 265                 270

Thr Arg Asn Gly Lys Asn Ile Asp Ile Ala Thr Ser Met Thr Pro Gln
        275                 280                 285

Phe Ser Ser Val Ser Leu Gly Ala Gly Ala Asp Ala Pro Thr Leu Ser
    290                 295                 300

Val Asp Gly Asp Ala Leu Asn Val Gly Ser Lys Lys Asp Asn Lys Pro
305                 310                 315                 320

Val Arg Ile Thr Asn Val Ala Pro Gly Val Lys Glu Gly Asp Val Thr
                325                 330                 335

Asn Val Ala Gln Leu Lys Gly Val Ala Gln Asn Leu Asn Asn Arg Ile
            340                 345                 350

Asp Asn Val Asp Gly Asn Ala Arg Ala Gly Ile Ala Gln Ala Ile Ala
        355                 360                 365

Thr Ala Gly Leu Val Gln Ala Tyr Leu Pro Gly Lys Ser Met Met Ala
    370                 375                 380

Ile Gly Gly Gly Thr Tyr Arg Gly Glu Ala Gly Tyr Ala Ile Gly Tyr
385                 390                 395                 400

Ser Ser Ile Ser Asp Gly Gly Asn Trp Ile Ile Lys Gly Thr Ala Ser
                405                 410                 415

Gly Asn Ser Arg Gly His Phe Gly Ala Ser Ala Ser Val Gly Tyr Gln
```

```
                   420             425             430
Trp

<210> SEQ ID NO 27
<211> LENGTH: 502
<212> TYPE: PRT
<213> ORGANISM: Neisseria meningitidis

<400> SEQUENCE: 27

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Thr Leu Lys Ala Gly Asp Asn Leu Lys Ile Lys Gln
    50                  55                  60

Phe Thr Tyr Ser Leu Lys Lys Asp Leu Thr Asp Leu Thr Ser Val Gly
65                  70                  75                  80

Thr Glu Lys Leu Ser Phe Ser Ala Asn Gly Asn Lys Val Asn Ile Thr
                85                  90                  95

Ser Asp Thr Lys Gly Leu Asn Phe Ala Lys Glu Thr Ala Gly Thr Asn
            100                 105                 110

Gly Asp Thr Thr Val His Leu Asn Gly Ile Gly Ser Thr Leu Thr Asp
        115                 120                 125

Arg Ala Ala Ser Val Lys Asp Val Leu Asn Ala Gly Trp Asn Ile Lys
    130                 135                 140

Gly Val Lys Asn Val Asp Phe Val Arg Thr Tyr Asp Thr Val Glu Phe
145                 150                 155                 160

Leu Ser Ala Asp Thr Lys Thr Thr Thr Val Asn Val Glu Ser Lys Asp
                165                 170                 175

Asn Gly Lys Lys Thr Glu Val Lys Ile Gly Ala Lys Thr Ser Val Ile
            180                 185                 190

Lys Glu Lys Asp Gly Lys Leu Val Thr Gly Lys Asp Lys Gly Glu Asn
        195                 200                 205

Gly Ser Ser Thr Asp Glu Gly Glu Gly Leu Val Thr Ala Lys Glu Val
    210                 215                 220

Ile Asp Ala Val Asn Lys Ala Gly Trp Arg Met Lys Thr Thr Thr Ala
225                 230                 235                 240

Asn Gly Gln Thr Gly Gln Ala Asp Lys Phe Glu Thr Val Thr Ser Gly
                245                 250                 255

Thr Asn Val Thr Phe Ala Ser Gly Lys Gly Thr Thr Ala Thr Val Ser
            260                 265                 270

Lys Asp Asp Gln Gly Asn Ile Thr Val Met Tyr Asp Val Asn Val Gly
        275                 280                 285

Asp Ala Leu Asn Val Asn Gln Leu Gln Asn Ser Gly Trp Asn Leu Asp
    290                 295                 300

Ser Lys Ala Val Ala Gly Ser Ser Gly Lys Val Ile Ser Gly Asn Val
305                 310                 315                 320

Ser Pro Ser Lys Gly Lys Met Asp Glu Thr Val Asn Ile Asn Ala Gly
                325                 330                 335

Asn Asn Ile Glu Ile Thr Arg Asn Gly Lys Asn Ile Asp Ile Ala Thr
            340                 345                 350

Ser Met Thr Pro Gln Phe Ser Ser Val Ser Leu Gly Ala Gly Ala Asp
        355                 360                 365
```

```
Ala Pro Thr Leu Ser Val Asp Gly Asp Ala Leu Asn Val Gly Ser Lys
        370                 375                 380
Lys Asp Asn Lys Pro Val Arg Ile Thr Asn Val Ala Pro Gly Val Lys
385                 390                 395                 400
Glu Gly Asp Val Thr Asn Val Ala Gln Leu Lys Gly Val Ala Gln Asn
                405                 410                 415
Leu Asn Asn Arg Ile Asp Asn Val Asp Gly Asn Ala Arg Ala Gly Ile
            420                 425                 430
Ala Gln Ala Ile Ala Thr Ala Gly Leu Val Gln Ala Tyr Leu Pro Gly
        435                 440                 445
Lys Ser Met Met Ala Ile Gly Gly Gly Thr Tyr Arg Gly Glu Ala Gly
        450                 455                 460
Tyr Ala Ile Gly Tyr Ser Ser Ile Ser Asp Gly Gly Asn Trp Ile Ile
465                 470                 475                 480
Lys Gly Thr Ala Ser Gly Asn Ser Arg Gly His Phe Gly Ala Ser Ala
                485                 490                 495
Ser Val Gly Tyr Gln Trp
            500
```

<210> SEQ ID NO 28
<211> LENGTH: 1539
<212> TYPE: DNA
<213> ORGANISM: Neisseria meningitidis

<400> SEQUENCE: 28

```
atgaacaaaa tataccgcat catttggaat agtgccctca atgcatgggt cgtcgtatcc      60
gagctcacac gcaaccacac caaacgcgcc tccgcaaccg tgaagaccgc cgtattggcg     120
actctgttgt ttgcaacggt tcaggcaagt gctaacaatg aaacagatct gaccagtgtt     180
ggaactgaaa aattatcgtt tagcgcaaac ggcaataaag tcaacatcac aagcgacacc     240
aaaggcttga atttgcgaa agaaacggct gggacgaacg gcgacaccac ggttcatctg      300
aacggtattg gttcgacttt gaccgatacg ctgctgaata ccggagcgac cacaaacgta     360
accaacgaca acgttaccga tgacgagaaa aaacgtgcgg caagcgttaa agacgtatta     420
aacgctggct ggaacattaa aggcgttaaa cccggtacaa cagcttccga taacgttgat     480
ttcgtccgca cttacgacac agtcgagttc ttgagcgcag atacgaaaac aacgactgtt     540
aatgtggaaa gcaagacaa cggcaagaaa accgaagtta aaatcggtgc gaagacttct      600
gttattaaag aaaagacgg taagttggtt actggtaaag acaaaggcga gaatggttct     660
tctacagacg aaggcgaagg cttagtgact gcaaagaag tgattgatgc agtaaacaag      720
gctggttgga gaatgaaaac aacaaccgct aatggtcaaa caggtcaagc tgacaagttt     780
gaaaccgtta catcaggcac aaatgtaacc tttgctagtg gtaaaggtac aactgcgact     840
gtaagtaaag atgatcaagg caacatcact gttatgtatg atgtaaatgt cggcgatgcc     900
ctaaacgtca atcagctgca aaacagcggt tggaatttgg attccaaagc ggttgcaggt     960
tcttcgggca aagtcatcag cggcaatgtt tcgccgagca aggaaagat ggatgaaacc     1020
gtcaacatta tgccggcaa caacatcgag attacccgca acggtaaaaa tatcgacatc     1080
gccacttcga tgaccccgca gttttccagc gtttcgctcg gcgcggggc ggatgcgccc    1140
actttgagcg tggatgggga cgcattgaat gtcggcagca agaaggacaa caaacccgtc     1200
cgcattacca atgtcgcccc gggcgttaaa gagggggatg ttacaaacgt cgcacaactt     1260
aaaggcgtgg cgcaaaactt gaacaaccgc atcgacaatg tggacggcaa cgcgcgtgcg     1320
```

```
ggcatcgccc aagcgattgc aaccgcaggt ctggttcagg cgtatttgcc cggcaagagt      1380
atgatggcga tcggcggcgg cacttatcgc ggcgaagccg gttacgccat cggctactcc      1440
agtatttccg acggcggaaa ttggattatc aaaggcacgg cttccggcaa ttcgcgcggc      1500
catttcggtg cttccgcatc tgtcggttat cagtggtaa                             1539

<210> SEQ ID NO 29
<211> LENGTH: 1542
<212> TYPE: DNA
<213> ORGANISM: Neisseria meningitidis

<400> SEQUENCE: 29
atgaacaaaa tataccgcat catttggaat agtgccctca atgcctgggt cgccgtatcc        60
gagctcacac gcaaccacac caaacgcgcc tccgcaaccg tgaagaccgc cgtattggcg       120
acactgttgt ttgcaacggt tcaggcgaat gctaccgatg aaacaggcct gatcaatgtt       180
gaaactgaaa aattatcgtt tggcgcaaac ggcaagaaag tcaacatcat aagcgacacc       240
aaaggcttga atttcgcgaa agaaacggct gggacgaacg gcgacaccac ggttcatctg       300
aacggtatcg gttcgacttt gaccgatatg ctgctgaata ccggagcgac cacaaacgta       360
accaacgaca acgttaccga tgacgagaaa aaacgtgcgg caagcgttaa agacgtatta       420
aacgcaggct ggaacattaa aggcgttaaa cccggtacaa cagcttccga taacgttgat       480
ttcgtccgca cttacgacac agtcgagttc ttgagcgcag atacgaaaac aacgactgtt       540
aatgtggaaa gcaagacaa cggcaagaaa accgaagtta aaatcggtgc gaagacttct       600
gttattaaag aaaagacgg taagttggtt actggtaaag gcaaaggcga gaatggttct       660
tctacagacg aaggcgaagg cttagtgact gcaaaagaag tgattgatgc agtaaacaag       720
gctggttgga gaatgaaaac aacaaccgct aatggtcaaa caggtcaagc tgacaagttt       780
gaaaccgtta catcaggcac aaaagtaacc tttgctagtg gtaatggtac aactgcgact       840
gtaagtaaag atgatcaagg caacatcact gttaagtatg atgtaaatgt cggcgatgcc       900
ctaaacgtca atcagctgca aaacagcggt tggaatttgg attccaaagc ggttgcaggt       960
tcttcgggca aagtcatcag cggcaatgtt tcgccgagca agggaaagat ggatgaaacc      1020
gtcaacatta tgccggcaa caacatcgag attacccgca acggcaaaaa tatcgacatc      1080
gccacttcga tgaccccgca attttccagc gtttcgctcg gcgcggggc ggatgcgccc      1140 actttaagcg tggatgacga gggcgcgttg aatgtcggca gcaaggatgc caacaaaccc      1200
gtccgcatta ccaatgtcgc cccgggcgtt aaagaggggg atgttacaaa cgtcgcgcaa      1260
cttaaaggtg tggcgcaaaa cttgaacaac cgcatcgaca atgtgaacgg caacgcgcgt      1320 gcggcatcg cccaagcgat tgcaaccgca ggtctggttc aggcgtatct gcccggcaag      1380
agtatgatgg cgatcggcgg cggcacttat ctcggcgaag ccggttatgc catcggctac      1440
tcaagcattt ccgccggcgg aaattggatt atcaaaggca cggcttccgg caattcgcgc      1500
ggccatttcg gtgcttccgc atctgtcggt tatcagtggt aa                         1542

<210> SEQ ID NO 30
<211> LENGTH: 1224
<212> TYPE: DNA
<213> ORGANISM: Neisseria meningitidis

<400> SEQUENCE: 30
atgaacaaaa tataccgcat catttggaat agtgccctca atgcatgggt cgtcgtatcc        60
gagctcacac gcaaccacac caaacgcgcc tccgcaaccg tgaagaccgc cgtattggcg       120
```

```
actctgttgt tgcaacggt tcaggcaagt gctaacaacg ttgatttcgt ccgcacttac      180
gacacagtcg agttcttgag cgcagatacg aaaacaacga ctgttaatgt ggaaagcaaa      240
gacaacggca agaaaaccga agttaaaatc ggtgcgaaga cttctgttat taaagaaaaa      300
gacggtaagt tggttactgg taaagacaaa ggcgagaatg ttcttctac agacgaaggc       360 gaaggcttag tgactgcaaa agaagtgatt gatgcagtaa acaaggctgg ttggagaatg      420
aaaacaacaa ccgctaatgg tcaaacaggt caagctgaca gtttgaaaac cgttacatca      480
ggcacaaatg taacctttgc tagtggtaaa ggtacaactg cgactgtaag taaagatgat      540
caaggcaaca tcactgttat gtatgatgta aatgtcggcg atgccctaaa cgtcaatcag      600
ctgcaaaaca gcggttggaa tttggattcc aaagcggttg caggttcttc gggcaaagtc      660
atcagcggca atgtttcgcc gagcaaggga agatggatg aaaccgtcaa cattaatgcc       720
ggcaacaaca tcgagattac ccgcaacggt aaaaatatcg acatcgccac ttcgatgacc      780
ccgcagtttt ccagcgtttc gctcggcgcg gggcggatg cgcccacttt gagcgtggat       840
ggggacgcat tgaatgtcgg cagcaagaag gacaacaaac ccgtccgcat taccaatgtc      900
gccccgggcg ttaaagaggg ggatgttaca acgtcgcac aacttaaagg cgtggcgcaa       960
aacttgaaca accgcatcga caatgtggac ggcaacgcgc gtgcgggcat cgcccaagcg     1020
attgcaaccg caggtctggt tcaggcgtat ttgcccggca agagtatgat ggcgatcggc     1080
ggcggcactt atcgcggcga agccggttac gccatcggct actccagtat ttccgacggc     1140
ggaaattgga ttatcaaagg cacggcttcc ggcaattcgc gcggccattt cggtgcttcc     1200
gcatctgtcg gttatcagtg gtaa                                           1224
```

<210> SEQ ID NO 31
<211> LENGTH: 1302
<212> TYPE: DNA
<213> ORGANISM: Neisseria meningitidis

<400> SEQUENCE: 31

```
atgaacaaaa tataccgcat catttggaat agtgccctca atgcatgggt cgtcgtatcc       60
gagctcacac gcaaccacac caaacgcgcc tccgcaaccg tgaagaccgc cgtattggcg      120
actctgttgt tgcaacggt tcaggcaagt gctaaccgtg cggcaagcgt taaagacgta      180
ttaaacgctg gctggaacat taaaggcgtt aaacccggta caacagcttc cgataacgtt      240
gatttcgtcc gcacttacga cacagtcgag ttcttgagcg cagatacgaa aacaacgact      300 gttaatgtg aaagcaaaga caacggcaag aaaaccgaag ttaaaatcgg tgcgaagact      360
tctgttatta agaaaaaga cggtaagttg gttactggta agacaaagg cgagaatggt       420 tcttctacag acgaaggcga aggcttagtg actgcaaaag aagtgattga tgcagtaaac      480
aaggctggtt ggagaatgaa aacaacaacc gctaatggtc aaacaggtca agctgacaag      540
tttgaaaccg ttacatcagg cacaaatgta acctttgcta gtggtaaagg tacaactgcg      600
actgtaagta aagatgatca aggcaacatc actgttatgt atgatgtaaa tgtcggcgat      660
gccctaaacg tcaatcagct gcaaaacagc ggttggaatt tggattccaa agcggttgca     720
ggttcttcgg gcaaagtcat cagcggcaat gtttcgccga gcaagggaaa gatggatgaa      780
accgtcaaca ttaatgccgg caacaacatc gagattaccc gcaacggtaa aaatatcgac      840
atcgccactt cgatgacccc gcagttttcc agcgtttcgc tcggcgcggg ggcggatgcg      900
cccactttga gcgtggatgg ggacgcattg aatgtcggca gcaagaagga caacaaaccc      960
gtccgcatta ccaatgtcgc cccgggcgtt aaagaggggg atgttacaaa cgtcgcacaa     1020
```

```
cttaaaggcg tggcgcaaaa cttgaacaac cgcatcgaca atgtggacgg caacgcgcgt    1080
gcgggcatcg cccaagcgat tgcaaccgca ggtctggttc aggcgtattt gcccggcaag    1140
agtatgatgg cgatcggcgg cggcacttat cgcggcgaag ccggttacgc catcggctac    1200
tccagtattt ccgacggcgg aaattggatt atcaaaggca cggcttccgg caattcgcgc    1260
ggccatttcg gtgcttccgc atctgtcggt tatcagtggt aa                       1302

<210> SEQ ID NO 32
<211> LENGTH: 1509
<212> TYPE: DNA
<213> ORGANISM: Neisseria meningitidis

<400> SEQUENCE: 32
atgaacaaaa taccgcat catttggaat agtgccctca atgcatgggt cgtcgtatcc       60
gagctcacac gcaaccacac caaacgcgcc tccgcaaccg tgaagaccgc cgtattggcg    120
actctgttgt ttgcaacggt tcaggcaagt gctaacaccc tcaaagccgg cgacaacctg    180
aaaatcaaac aattcaccta ctcgctgaaa aaagacctca cagatctgac cagtgttgga    240
actgaaaaat tatcgtttag cgcaaacggg aataaagtca acatcacaag cgacaccaaa    300
ggcttgaatt ttgcgaaaga aacggctggg acgaacggcg caccacggt tcatctgaac     360 ggtattggtt cgactttgac cgatcgtgcg gcaagcgtta aagacgtatt aaacgctggc    420
tggaacatta aaggcgttaa aaacgttgat ttcgtccgca cttacgacac agtcgagttc    480
ttgagcgcag atacgaaaac aacgactgtt aatgtggaaa gcaaagacaa cggcaagaaa    540
accgaagtta aaatcggtgc gaagacttct gttattaaag aaaagacgg taagttggtt     600 actggtaaag acaaggcga gaatggttct tctacagacg aaggcgaagg cttagtgact      660
gcaaaagaag tgattgatgc agtaaacaag gctggttgga gaatgaaaac aacaaccgct    720
aatggtcaaa caggtcaagc tgacaagttt gaaaccgtta catcaggcac aaatgtaacc    780
tttgctagtg gtaaaggtac aactgcgact gtaagtaaag atgatcaagg caacatcact    840
gttatgtatg atgtaaatgt cggcgatgcc ctaaacgtca atcagctgca aaacagcggt    900
tggaatttgg attccaaagc ggttgcaggt tcttcgggca aagtcatcag cggcaatgtt    960
tcgccgagca agggaaagat ggatgaaacc gtcaacatta atgccggcaa caacatcgag   1020
attacccgca acggtaaaaa tatcgacatc gccacttcga tgaccccgca gttttccagc   1080
gtttcgctcg gcgcgggggc ggatgcgccc actttgagcg tggatgggga cgcattgaat   1140
gtcggcagca agaaggacaa caaacccgtc cgcattacca atgtcgcccc gggcgttaaa   1200
gagggggatg ttacaaacgt cgcacaactt aaaggcgtgg cgcaaaactt gaacaaccgc   1260
atcgacaatg tggacggcaa cgcgcgtgcg ggcatcgccc aagcgattgc aaccgcaggt   1320
ctggttcagg cgtatttgcc cggcaagagt atgatggcga tcggcggcgg cacttatcgc   1380
ggcgaagccg gttacgccat cggctactcc agtatttccg acggcggaaa ttggattatc   1440
aaaggcacgg cttccggcaa ttcgcgcggc catttcggtg cttccgcatc tgtcggttat   1500
cagtggtaa                                                          1509

<210> SEQ ID NO 33
<211> LENGTH: 540
<212> TYPE: PRT
<213> ORGANISM: Neisseria meningitidis

<400> SEQUENCE: 33

Asn Asn Glu Glu Gln Glu Glu Tyr Leu Tyr Leu His Pro Val Gln Arg
1               5                  10                  15
```

-continued

```
Thr Val Ala Val Leu Ile Val Asn Ser Asp Lys Glu Gly Ala Gly Glu
            20                  25                  30
Lys Glu Lys Val Glu Glu Asn Ser Asp Trp Ala Val Tyr Phe Asn Glu
        35                  40                  45
Lys Gly Val Leu Thr Ala Arg Glu Ile Thr Leu Lys Ala Gly Asp Asn
 50                  55                  60
Leu Lys Ile Lys Gln Asn Gly Thr Asn Phe Thr Tyr Ser Leu Lys Lys
 65                  70                  75                  80
Asp Leu Thr Asp Leu Thr Ser Val Gly Thr Glu Lys Leu Ser Phe Ser
                85                  90                  95
Ala His Gly Asn Lys Val Asn Ile Thr Ser Asp Thr Lys Gly Leu Asn
            100                 105                 110
Phe Ala Lys Glu Thr Ala Gly Thr Asn Gly Asp Thr Thr Val His Leu
        115                 120                 125
Asn Gly Ile Gly Ser Thr Leu Thr Asp Thr Leu Leu Asn Thr Gly Ala
130                 135                 140
Thr Thr Asn Val Thr Asn Asp Asn Val Thr Asp Asp Glu Lys Lys Arg
145                 150                 155                 160
Ala Ala Ser Val Lys Asp Val Leu Asn Ala Gly Trp Asn Ile Lys Gly
                165                 170                 175
Val Lys Pro Gly Thr Thr Ala Ser Asp Asn Val Asp Phe Val Arg Thr
            180                 185                 190
Tyr Asp Thr Val Glu Phe Leu Ser Ala Asp Thr Lys Thr Thr Thr Val
        195                 200                 205
Asn Val Glu Ser Lys Asp Asn Gly Lys Lys Thr Glu Val Lys Ile Gly
210                 215                 220
Ala Lys Thr Ser Val Ile Lys Gly Lys Asp Gly Lys Leu Val Thr Gly
225                 230                 235                 240
Lys Asp Lys Gly Glu Asn Gly Ser Ser Thr Asp Glu Gly Gly Leu
                245                 250                 255
Val Thr Ala Lys Glu Val Ile Asp Ala Val Asn Lys Ala Gly Trp Arg
            260                 265                 270
Met Lys Thr Thr Thr Ala Asn Gly Gln Thr Gly Gln Ala Asp Lys Phe
        275                 280                 285
Glu Thr Val Thr Ser Gly Thr Asn Val Thr Phe Ala Ser Gly Lys Gly
        290                 295                 300
Thr Thr Ala Thr Val Ser Lys Asp Asp Gln Gly Asn Ile Thr Val Met
305                 310                 315                 320
Tyr Asp Val Asn Val Gly Asp Ala Leu Asn Val Asn Gln Leu Gln Asn
                325                 330                 335
Ser Gly Trp Asn Leu Asp Ser Lys Ala Val Ala Gly Ser Ser Gly Lys
            340                 345                 350
Val Ile Ser Gly Asn Val Ser Pro Ser Lys Gly Lys Met Asp Glu Thr
        355                 360                 365
Val Asn Ile Asn Ala Gly Asn Asn Ile Glu Ile Thr Arg Asn Gly Lys
        370                 375                 380
Asn Ile Asp Ile Ala Thr Ser Met Thr Pro Gln Phe Ser Ser Val Ser
385                 390                 395                 400
Leu Gly Ala Gly Ala Asp Ala Pro Thr Leu Ser Val Asp Gly Asp Ala
                405                 410                 415
Leu Asn Val Gly Ser Lys Lys Asp Asn Lys Pro Val Arg Ile Thr Asn
            420                 425                 430
Val Ala Pro Gly Val Lys Glu Gly Asp Val Thr Asn Val Ala Gln Leu
```

```
                    435                 440                 445
Lys Gly Val Ala Gln Asn Leu Asn Asn Arg Ile Asp Asn Val Asp Gly
                450                 455                 460

Asn Ala Arg Ala Gly Ile Ala Gln Ala Ile Ala Thr Ala Gly Leu Val
465                 470                 475                 480

Gln Ala Tyr Leu Pro Gly Lys Ser Met Met Ala Ile Gly Gly Thr
                    485                 490                 495

Tyr Arg Gly Glu Ala Gly Tyr Ala Ile Gly Tyr Ser Ser Ile Ser Asp
                500                 505                 510

Gly Gly Asn Trp Ile Ile Lys Gly Thr Ala Ser Gly Asn Ser Arg Gly
                515                 520                 525

His Phe Gly Ala Ser Ala Ser Val Gly Tyr Gln Trp
                530                 535                 540

<210> SEQ ID NO 34
<211> LENGTH: 541
<212> TYPE: PRT
<213> ORGANISM: Neisseria meningitidis

<400> SEQUENCE: 34

Thr Asp Glu Asp Glu Glu Glu Leu Glu Ser Val Gln Arg Ser Val
1               5                   10                  15

Val Gly Ser Ile Gln Ala Ser Met Glu Gly Ser Val Glu Leu Glu Thr
                20                  25                  30

Ile Ser Leu Ser Met Thr Asn Asp Ser Lys Glu Phe Val Asp Pro Tyr
                35                  40                  45

Ile Val Val Thr Leu Lys Ala Gly Asp Asn Leu Lys Ile Lys Gln Asn
50                  55                  60

Thr Asn Glu Asn Thr Asn Ala Ser Ser Phe Thr Tyr Ser Leu Lys Lys
65                  70                  75                  80

Asp Leu Thr Gly Leu Ile Asn Val Glu Thr Glu Lys Leu Ser Phe Gly
                85                  90                  95

Ala Asn Gly Lys Lys Val Asn Ile Ile Ser Asp Thr Lys Gly Leu Asn
                100                 105                 110

Phe Ala Lys Glu Thr Ala Gly Thr Asn Gly Asp Thr Thr Val His Leu
                115                 120                 125

Asn Gly Ile Gly Ser Thr Leu Thr Asp Met Leu Leu Asn Thr Gly Ala
                130                 135                 140

Thr Thr Asn Val Thr Asn Asp Asn Val Thr Asp Asp Glu Lys Lys Arg
145                 150                 155                 160

Ala Ala Ser Val Lys Asp Val Leu Asn Ala Gly Trp Asn Ile Lys Gly
                165                 170                 175

Val Lys Pro Gly Thr Thr Ala Ser Asp Asn Val Asp Phe Val Arg Thr
                180                 185                 190

Tyr Asp Thr Val Glu Phe Leu Ser Ala Asp Thr Lys Thr Thr Thr Val
                195                 200                 205

Asn Val Glu Ser Lys Asp Asn Gly Lys Lys Thr Glu Val Lys Ile Gly
                210                 215                 220

Ala Lys Thr Ser Val Ile Lys Glu Lys Asp Gly Lys Leu Val Thr Gly
225                 230                 235                 240

Lys Gly Lys Gly Glu Asn Gly Ser Ser Thr Asp Glu Gly Glu Gly Leu
                245                 250                 255

Val Thr Ala Lys Glu Val Ile Asp Ala Val Asn Lys Ala Gly Trp Arg
                260                 265                 270

Met Lys Thr Thr Thr Ala Asn Gly Gln Thr Gly Gln Ala Asp Lys Phe
```

```
              275                 280                 285
Glu Thr Val Thr Ser Gly Thr Lys Val Thr Phe Ala Ser Gly Asn Gly
    290                 295                 300

Thr Thr Ala Thr Val Ser Lys Asp Asp Gln Gly Asn Ile Thr Val Lys
305                 310                 315                 320

Tyr Asp Val Asn Val Gly Asp Ala Leu Asn Val Asn Gln Leu Gln Asn
                325                 330                 335

Ser Gly Trp Asn Leu Asp Ser Lys Ala Val Ala Gly Ser Ser Gly Lys
            340                 345                 350

Val Ile Ser Gly Asn Val Ser Pro Ser Lys Gly Lys Met Asp Glu Thr
        355                 360                 365

Val Asn Ile Asn Ala Gly Asn Asn Ile Glu Ile Thr Arg Asn Gly Lys
    370                 375                 380

Asn Ile Asp Ile Ala Thr Ser Met Thr Pro Gln Phe Ser Ser Val Ser
385                 390                 395                 400

Leu Gly Ala Gly Ala Asp Ala Pro Thr Leu Ser Val Asp Asp Glu Gly
                405                 410                 415

Ala Leu Asn Val Gly Ser Lys Asp Ala Asn Lys Pro Val Arg Ile Thr
            420                 425                 430

Asn Val Ala Pro Gly Val Lys Glu Gly Asp Val Thr Asn Val Ala Gln
        435                 440                 445

Leu Lys Gly Val Ala Gln Asn Leu Asn Asn Arg Ile Asp Asn Val Asn
    450                 455                 460

Gly Asn Ala Arg Ala Gly Ile Ala Gln Ala Ile Ala Thr Ala Gly Leu
465                 470                 475                 480

Val Gln Ala Tyr Leu Pro Gly Lys Ser Met Met Ala Ile Gly Gly Gly
                485                 490                 495

Thr Tyr Leu Gly Glu Ala Gly Tyr Ala Ile Gly Tyr Ser Ser Ile Ser
            500                 505                 510

Ala Gly Gly Asn Trp Ile Ile Lys Gly Thr Ala Ser Gly Asn Ser Arg
        515                 520                 525

Gly His Phe Gly Ala Ser Ala Ser Val Gly Tyr Gln Trp
    530                 535                 540

<210> SEQ ID NO 35
<211> LENGTH: 461
<212> TYPE: PRT
<213> ORGANISM: Neisseria meningitidis

<400> SEQUENCE: 35

Asn Asn Glu Thr Asp Leu Thr Ser Val Gly Thr Glu Lys Leu Ser Phe
1               5                   10                  15

Ser Ala Asn Gly Asn Lys Val Asn Ile Thr Ser Asp Thr Lys Gly Leu
            20                  25                  30

Asn Phe Ala Lys Glu Thr Ala Gly Thr Asn Gly Asp Thr Thr Val His
        35                  40                  45

Leu Asn Gly Ile Gly Ser Thr Leu Thr Asp Thr Leu Leu Asn Thr Gly
    50                  55                  60

Ala Thr Thr Asn Val Thr Asn Asp Asn Val Thr Asp Asp Glu Lys Lys
65                  70                  75                  80

Arg Ala Ala Ser Val Lys Asp Val Leu Asn Ala Gly Trp Asn Ile Lys
                85                  90                  95

Gly Val Lys Pro Gly Thr Thr Ala Ser Asp Asn Val Asp Phe Val Arg
            100                 105                 110

Thr Tyr Asp Thr Val Glu Phe Leu Ser Ala Asp Thr Lys Thr Thr Thr
```

```
            115                 120                 125
Val Asn Val Glu Ser Lys Asp Asn Gly Lys Lys Thr Glu Val Lys Ile
            130                 135                 140
Gly Ala Lys Thr Ser Val Ile Lys Glu Lys Asp Gly Lys Leu Val Thr
145                 150                 155                 160
Gly Lys Asp Lys Gly Glu Asn Gly Ser Ser Thr Asp Glu Gly Glu Gly
                    165                 170                 175
Leu Val Thr Ala Lys Glu Val Ile Asp Ala Val Asn Lys Ala Gly Trp
            180                 185                 190
Arg Met Lys Thr Thr Thr Ala Asn Gly Gln Thr Gly Gln Ala Asp Lys
            195                 200                 205
Phe Glu Thr Val Thr Ser Gly Thr Asn Val Thr Phe Ala Ser Gly Lys
            210                 215                 220
Gly Thr Thr Ala Thr Val Ser Lys Asp Asp Gln Gly Asn Ile Thr Val
225                 230                 235                 240
Met Tyr Asp Val Asn Val Gly Asp Ala Leu Asn Val Asn Gln Leu Gln
                    245                 250                 255
Asn Ser Gly Trp Asn Leu Asp Ser Lys Ala Val Ala Gly Ser Ser Gly
            260                 265                 270
Lys Val Ile Ser Gly Asn Val Ser Pro Ser Lys Gly Lys Met Asp Glu
            275                 280                 285
Thr Val Asn Ile Asn Ala Gly Asn Asn Ile Glu Ile Thr Arg Asn Gly
            290                 295                 300
Lys Asn Ile Asp Ile Ala Thr Ser Met Thr Pro Gln Phe Ser Ser Val
305                 310                 315                 320
Ser Leu Gly Ala Gly Ala Asp Ala Pro Thr Leu Ser Val Asp Gly Asp
                    325                 330                 335
Ala Leu Asn Val Gly Ser Lys Lys Asp Asn Lys Pro Val Arg Ile Thr
            340                 345                 350
Asn Val Ala Pro Gly Val Lys Glu Gly Asp Val Thr Asn Val Ala Gln
            355                 360                 365
Leu Lys Gly Val Ala Gln Asn Leu Asn Asn Arg Ile Asp Asn Val Asp
            370                 375                 380
Gly Asn Ala Arg Ala Gly Ile Ala Gln Ala Ile Ala Thr Ala Gly Leu
385                 390                 395                 400
Val Gln Ala Tyr Leu Pro Gly Lys Ser Met Met Ala Ile Gly Gly Gly
                    405                 410                 415
Thr Tyr Arg Gly Glu Ala Gly Tyr Ala Ile Gly Tyr Ser Ser Ile Ser
            420                 425                 430
Asp Gly Gly Asn Trp Ile Ile Lys Gly Thr Ala Ser Gly Asn Ser Arg
            435                 440                 445
Gly His Phe Gly Ala Ser Ala Ser Val Gly Tyr Gln Trp
            450                 455                 460

<210> SEQ ID NO 36
<211> LENGTH: 462
<212> TYPE: PRT
<213> ORGANISM: Neisseria meningitidis

<400> SEQUENCE: 36

Thr Asp Glu Thr Gly Leu Ile Asn Val Glu Thr Glu Lys Leu Ser Phe
1               5                   10                  15
Gly Ala Asn Gly Lys Lys Val Asn Ile Ile Ser Asp Thr Lys Gly Leu
            20                  25                  30
Asn Phe Ala Lys Glu Thr Ala Gly Thr Asn Gly Asp Thr Thr Val His
```

-continued

```
              35                   40                    45
Leu Asn Gly Ile Gly Ser Thr Leu Thr Asp Met Leu Leu Asn Thr Gly
 50                      55                   60
Ala Thr Thr Asn Val Thr Asn Asp Asn Val Thr Asp Asp Glu Lys Lys
 65                      70                   75                  80
Arg Ala Ala Ser Val Lys Asp Val Leu Asn Ala Gly Trp Asn Ile Lys
                     85                   90                   95
Gly Val Lys Pro Gly Thr Ala Ser Asp Asn Val Asp Phe Val Arg
                    100                  105                  110
Thr Tyr Asp Thr Val Glu Phe Leu Ser Ala Asp Thr Lys Thr Thr Thr
                    115                  120                  125
Val Asn Val Glu Ser Lys Asp Asn Gly Lys Lys Thr Glu Val Lys Ile
                    130                  135                  140
Gly Ala Lys Thr Ser Val Ile Lys Glu Lys Asp Gly Lys Leu Val Thr
145                      150                  155                 160
Gly Lys Gly Lys Gly Glu Asn Gly Ser Ser Thr Asp Glu Gly Glu Gly
                    165                  170                  175
Leu Val Thr Ala Lys Glu Val Ile Asp Ala Val Asn Lys Ala Gly Trp
                    180                  185                  190
Arg Met Lys Thr Thr Thr Ala Asn Gly Gln Thr Gly Gln Ala Asp Lys
                    195                  200                  205
Phe Glu Thr Val Thr Ser Gly Thr Lys Val Thr Phe Ala Ser Gly Asn
                    210                  215                  220
Gly Thr Thr Ala Thr Val Ser Lys Asp Asp Gln Gly Asn Ile Thr Val
225                      230                  235                 240
Lys Tyr Asp Val Asn Val Gly Asp Ala Leu Asn Val Asn Gln Leu Gln
                    245                  250                  255
Asn Ser Gly Trp Asn Leu Asp Ser Lys Ala Val Ala Gly Ser Ser Gly
                    260                  265                  270
Lys Val Ile Ser Gly Asn Val Ser Pro Ser Lys Gly Lys Met Asp Glu
                    275                  280                  285
Thr Val Asn Ile Asn Ala Gly Asn Asn Ile Glu Ile Thr Arg Asn Gly
                    290                  295                  300
Lys Asn Ile Asp Ile Ala Thr Ser Met Thr Pro Gln Phe Ser Ser Val
305                      310                  315                 320
Ser Leu Gly Ala Gly Ala Asp Ala Pro Thr Leu Ser Val Asp Asp Glu
                    325                  330                  335
Gly Ala Leu Asn Val Gly Ser Lys Asp Ala Asn Lys Pro Val Arg Ile
                    340                  345                  350
Thr Asn Val Ala Pro Gly Val Lys Glu Gly Asp Val Thr Asn Val Ala
                    355                  360                  365
Gln Leu Lys Gly Val Ala Gln Asn Leu Asn Asn Arg Ile Asp Asn Val
                    370                  375                  380
Asn Gly Asn Ala Arg Ala Gly Ile Ala Gln Ala Ile Ala Thr Ala Gly
385                      390                  395                 400
Leu Val Gln Ala Tyr Leu Pro Gly Lys Ser Met Met Ala Ile Gly Gly
                    405                  410                  415
Gly Thr Tyr Leu Gly Glu Ala Gly Tyr Ala Ile Gly Tyr Ser Ser Ile
                    420                  425                  430
Ser Ala Gly Gly Asn Trp Ile Ile Lys Gly Thr Ala Ser Gly Asn Ser
                    435                  440                  445
Arg Gly His Phe Gly Ala Ser Ala Ser Val Gly Tyr Gln Trp
                    450                  455                  460
```

<210> SEQ ID NO 37
<211> LENGTH: 356
<212> TYPE: PRT
<213> ORGANISM: Neisseria meningitidis

<400> SEQUENCE: 37

```
Asn Asn Val Asp Phe Val Arg Thr Tyr Asp Thr Val Glu Phe Leu Ser
1               5                   10                  15
Ala Asp Thr Lys Thr Thr Val Asn Val Glu Ser Lys Asp Asn Gly
            20                  25                  30
Lys Lys Thr Glu Val Lys Ile Gly Ala Lys Thr Ser Val Ile Lys Glu
            35                  40                  45
Lys Asp Gly Lys Leu Val Thr Gly Lys Asp Lys Gly Glu Asn Gly Ser
        50                  55                  60
Ser Thr Asp Glu Gly Glu Gly Leu Val Thr Ala Lys Glu Val Ile Asp
65                  70                  75                  80
Ala Val Asn Lys Ala Gly Trp Arg Met Lys Thr Thr Thr Ala Asn Gly
                85                  90                  95
Gln Thr Gly Gln Ala Asp Lys Phe Glu Thr Val Thr Ser Gly Thr Asn
            100                 105                 110
Val Thr Phe Ala Ser Gly Lys Gly Thr Thr Ala Thr Val Ser Lys Asp
            115                 120                 125
Asp Gln Gly Asn Ile Thr Val Met Tyr Asp Val Asn Val Gly Asp Ala
        130                 135                 140
Leu Asn Val Asn Gln Leu Gln Asn Ser Gly Trp Asn Leu Asp Ser Lys
145                 150                 155                 160
Ala Val Ala Gly Ser Ser Gly Lys Val Ile Ser Gly Asn Val Ser Pro
                165                 170                 175
Ser Lys Gly Lys Met Asp Glu Thr Val Asn Ile Asn Ala Gly Asn Asn
            180                 185                 190
Ile Glu Ile Thr Arg Asn Gly Lys Asn Ile Asp Ile Ala Thr Ser Met
            195                 200                 205
Thr Pro Gln Phe Ser Ser Val Ser Leu Gly Ala Gly Ala Asp Ala Pro
        210                 215                 220
Thr Leu Ser Val Asp Gly Asp Ala Leu Asn Val Gly Ser Lys Lys Asp
225                 230                 235                 240
Asn Lys Pro Val Arg Ile Thr Asn Val Ala Pro Gly Val Lys Glu Gly
                245                 250                 255
Asp Val Thr Asn Val Ala Gln Leu Lys Gly Val Ala Gln Asn Leu Asn
            260                 265                 270
Asn Arg Ile Asp Asn Val Asp Gly Asn Ala Arg Ala Gly Ile Ala Gln
            275                 280                 285
Ala Ile Ala Thr Ala Gly Leu Val Gln Ala Tyr Leu Pro Gly Lys Ser
        290                 295                 300
Met Met Ala Ile Gly Gly Gly Thr Tyr Arg Gly Glu Ala Gly Tyr Ala
305                 310                 315                 320
Ile Gly Tyr Ser Ser Ile Ser Asp Gly Gly Asn Trp Ile Ile Lys Gly
                325                 330                 335
Thr Ala Ser Gly Asn Ser Arg Gly His Phe Gly Ala Ser Ala Ser Val
            340                 345                 350
Gly Tyr Gln Trp
            355
```

<210> SEQ ID NO 38
<211> LENGTH: 382

<212> TYPE: PRT
<213> ORGANISM: Neisseria meningitidis

<400> SEQUENCE: 38

```
Asn Arg Ala Ala Ser Val Lys Asp Val Leu Asn Ala Gly Trp Asn Ile
1               5                   10                  15

Lys Gly Val Lys Pro Gly Thr Thr Ala Ser Asp Asn Val Asp Phe Val
            20                  25                  30

Arg Thr Tyr Asp Thr Val Glu Phe Leu Ser Ala Asp Thr Lys Thr Thr
        35                  40                  45

Thr Val Asn Val Glu Ser Lys Asp Asn Gly Lys Lys Thr Glu Val Lys
50                  55                  60

Ile Gly Ala Lys Thr Ser Val Ile Lys Glu Lys Asp Gly Lys Leu Val
65                  70                  75                  80

Thr Gly Lys Asp Lys Gly Glu Asn Gly Ser Thr Asp Glu Gly Glu
            85                  90                  95

Gly Leu Val Thr Ala Lys Glu Val Ile Asp Ala Val Asn Lys Ala Gly
            100                 105                 110

Trp Arg Met Lys Thr Thr Thr Ala Asn Gly Gln Thr Gly Gln Ala Asp
        115                 120                 125

Lys Phe Glu Thr Val Thr Ser Gly Thr Asn Val Thr Phe Ala Ser Gly
130                 135                 140

Lys Gly Thr Thr Ala Thr Val Ser Lys Asp Asp Gln Gly Asn Ile Thr
145                 150                 155                 160

Val Met Tyr Asp Val Asn Val Gly Asp Ala Leu Asn Val Asn Gln Leu
                165                 170                 175

Gln Asn Ser Gly Trp Asn Leu Asp Ser Lys Ala Val Ala Gly Ser Ser
            180                 185                 190

Gly Lys Val Ile Ser Gly Asn Val Ser Pro Ser Lys Gly Lys Met Asp
        195                 200                 205

Glu Thr Val Asn Ile Asn Ala Gly Asn Asn Ile Glu Ile Thr Arg Asn
210                 215                 220

Gly Lys Asn Ile Asp Ile Ala Thr Ser Met Thr Pro Gln Phe Ser Ser
225                 230                 235                 240

Val Ser Leu Gly Ala Gly Ala Asp Ala Pro Thr Leu Ser Val Asp Gly
                245                 250                 255

Asp Ala Leu Asn Val Gly Ser Lys Lys Asp Asn Lys Pro Val Arg Ile
            260                 265                 270

Thr Asn Val Ala Pro Gly Val Lys Glu Gly Asp Val Thr Asn Val Ala
        275                 280                 285

Gln Leu Lys Gly Val Ala Gln Asn Leu Asn Asn Arg Ile Asp Asn Val
290                 295                 300

Asp Gly Asn Ala Arg Ala Gly Ile Ala Gln Ala Ile Ala Thr Ala Gly
305                 310                 315                 320

Leu Val Gln Ala Tyr Leu Pro Gly Lys Ser Met Met Ala Ile Gly Gly
                325                 330                 335

Gly Thr Tyr Arg Gly Glu Ala Gly Tyr Ala Ile Gly Tyr Ser Ser Ile
            340                 345                 350

Ser Asp Gly Gly Asn Trp Ile Ile Lys Gly Thr Ala Ser Gly Asn Ser
        355                 360                 365

Arg Gly His Phe Gly Ala Ser Ala Ser Val Gly Tyr Gln Trp
370                 375                 380
```

<210> SEQ ID NO 39
<211> LENGTH: 201

```
<212> TYPE: PRT
<213> ORGANISM: Neisseria meningitidis

<400> SEQUENCE: 39

Ser Ala Asn Thr Leu Lys Ala Gly Asp Asn Leu Lys Ile Lys Gln Phe
1               5                   10                  15

Thr Tyr Ser Leu Lys Lys Asp Leu Thr Asp Leu Thr Ser Val Gly Thr
            20                  25                  30

Glu Lys Leu Ser Phe Ser Ala Asn Gly Asn Lys Val Asn Ile Thr Ser
        35                  40                  45

Asp Thr Lys Gly Leu Asn Phe Ala Lys Glu Thr Ala Gly Thr Asn Gly
    50                  55                  60

Asp Thr Thr Val His Leu Asn Gly Ile Gly Ser Thr Leu Thr Asp Arg
65                  70                  75                  80

Ala Ala Ser Val Lys Asp Val Leu Asn Ala Gly Trp Asn Ile Lys Gly
                85                  90                  95

Val Lys Asn Val Asp Phe Val Arg Thr Tyr Asp Thr Val Glu Phe Leu
            100                 105                 110

Ser Ala Asp Thr Lys Thr Thr Thr Val Asn Val Glu Ser Lys Asp Asn
        115                 120                 125

Gly Lys Lys Thr Glu Val Lys Ile Gly Ala Lys Thr Ser Val Ile Lys
    130                 135                 140

Glu Lys Asp Gly Lys Leu Val Thr Gly Lys Asp Lys Gly Glu Asn Gly
145                 150                 155                 160

Ser Ser Thr Asp Glu Gly Glu Gly Leu Val Thr Ala Lys Glu Val Ile
                165                 170                 175

Asp Ala Val Asn Lys Ala Gly Trp Arg Met Lys Thr Thr Thr Ala Asn
            180                 185                 190

Gly Gln Thr Gly Gln Ala Asp Lys Phe
        195                 200

<210> SEQ ID NO 40
<211> LENGTH: 51
<212> TYPE: DNA
<213> ORGANISM: Neisseria meningitidis

<400> SEQUENCE: 40
caattaacgg ccgaataaaa ggaagccgat atgaacaaaa tataccgcat c         51

<210> SEQ ID NO 41
<211> LENGTH: 31
<212> TYPE: DNA
<213> ORGANISM: Neisseria meningitidis

<400> SEQUENCE: 41
tggaatccat ggaatcgcca cccttcccct c                                31

<210> SEQ ID NO 42
<211> LENGTH: 30
<212> TYPE: DNA
<213> ORGANISM: Neisseria meningitidis

<400> SEQUENCE: 42
ggtcagatct gtttcattgt tagcacttgc                                  30

<210> SEQ ID NO 43
<211> LENGTH: 30
<212> TYPE: DNA
<213> ORGANISM: Neisseria meningitidis
```

```
<400> SEQUENCE: 43
gatcaggcct gtatcttcat cggtagcatt                              30

<210> SEQ ID NO 44
<211> LENGTH: 39
<212> TYPE: DNA
<213> ORGANISM: Neisseria meningitidis

<400> SEQUENCE: 44
gacgaaatca acgttcttag cacttgcctg aacgttgc                     39

<210> SEQ ID NO 45
<211> LENGTH: 24
<212> TYPE: DNA
<213> ORGANISM: Neisseria meningitidis

<400> SEQUENCE: 45
aacgttgatt tcgtccgcac ttac                                    24

<210> SEQ ID NO 46
<211> LENGTH: 39
<212> TYPE: DNA
<213> ORGANISM: Neisseria meningitidis

<400> SEQUENCE: 46
aacgcttgcc gcacgcttag cacttgcctg caacgttgc                    39

<210> SEQ ID NO 47
<211> LENGTH: 24
<212> TYPE: DNA
<213> ORGANISM: Neisseria meningitidis

<400> SEQUENCE: 47
cgtgcggcaa gcgttaaaga cgta                                    24

<210> SEQ ID NO 48
<211> LENGTH: 72
<212> TYPE: DNA
<213> ORGANISM: Neisseria meningitidis

<400> SEQUENCE: 48
cagcgagtag gtgaattgtt tgattttcag gttgtcgccg gctttgaggg tgttagcact    60
tgcctgaacc gt                                                 72

<210> SEQ ID NO 49
<211> LENGTH: 24
<212> TYPE: DNA
<213> ORGANISM: Neisseria meningitidis

<400> SEQUENCE: 49
ttcacctact cgctgaaaaa agac                                    24

<210> SEQ ID NO 50
<211> LENGTH: 57
<212> TYPE: DNA
<213> ORGANISM: Neisseria meningitidis

<400> SEQUENCE: 50
gccagcgttt aatacgtctt taacgcttgc cgcacgatcg gtcaaagtcg aaccaat      57

<210> SEQ ID NO 51
<211> LENGTH: 57
<212> TYPE: DNA
```

-continued

```
<213> ORGANISM: Neisseria meningitidis

<400> SEQUENCE: 51
gtattaaacg ctggctggaa cattaaaggc gttaaaaacg ttgatttcgt ccgcact       57

<210> SEQ ID NO 52
<211> LENGTH: 11
<212> TYPE: PRT
<213> ORGANISM: Neisseria meningitidis
<220> FEATURE:
<221> NAME/KEY: misc_feature
<222> LOCATION: (1)..(2)
<223> OTHER INFORMATION: Xaa can be any naturally occurring amino acid

<400> SEQUENCE: 52

Xaa Xaa Glu Thr Asp Leu Thr Ser Val Gly Thr
1               5                   10
```